(12) United States Patent
Stuyver et al.

(10) Patent No.: US 7,718,790 B2
(45) Date of Patent: May 18, 2010

(54) KIT FOR ASSESSING MITOCHONDRIAL TOXICITY

(75) Inventors: Lieven Stuyver, Snellvile, GA (US); Michael J. Otto, Lilburn, GA (US)

(73) Assignee: Pharmasset, Inc., Princeton, NJ (US)

( * ) Notice: Subject to any disclaimer, the term of this patent is extended or adjusted under 35 U.S.C. 154(b) by 17 days.

(21) Appl. No.: 11/686,499

(22) Filed: Mar. 15, 2007

(65) Prior Publication Data
US 2007/0196824 A1 Aug. 23, 2007

Related U.S. Application Data

(60) Division of application No. 10/854,870, filed on May 27, 2004, now abandoned, which is a continuation of application No. 10/008,140, filed on Oct. 18, 2001, now abandoned.

(60) Provisional application No. 60/241,488, filed on Oct. 18, 2000, provisional application No. 60/256,067, filed on Dec. 15, 2000, provisional application No. 60/282,156, filed on Apr. 6, 2001.

(51) Int. Cl.
C07H 21/04 (2006.01)
(52) U.S. Cl. .................. 536/24.33; 536/24.31; 435/810
(58) Field of Classification Search ........................ None
See application file for complete search history.

(56) References Cited

U.S. PATENT DOCUMENTS

| | | | |
|---|---|---|---|
| 5,565,323 A | 10/1996 | Parker et al. |
| 5,756,282 A | 5/1998 | Crooke |
| 5,843,640 A | 12/1998 | Patterson |
| 6,054,265 A | 4/2000 | Barney |
| 6,210,875 B1 | 4/2001 | Patterson |
| 6,218,105 B1 | 4/2001 | Hall |
| 6,218,117 B1 | 4/2001 | Herrnstadt |
| 6,235,504 B1 | 5/2001 | Zhang |
| 6,489,095 B2 | 12/2002 | Herrnstadt |
| 2002/0164612 A1 | 11/2002 | Van Gemen |
| 2003/0124512 A1 | 7/2003 | Stuyver |
| 2007/0031824 A1 | 2/2007 | Stuyver et al. |

FOREIGN PATENT DOCUMENTS

EP 1211323 6/2002

(Continued)

OTHER PUBLICATIONS

Gerard, C.J. et al. Molecular Diagnosis 5(1):39-46 (Mar. 2000).*

(Continued)

*Primary Examiner*—Diana B Johannsen
(74) *Attorney, Agent, or Firm*—Merchant & Gould, PC

(57) ABSTRACT

Processes and methods for the simultaneous quantification of nucleic acids in diseased cells that are based on real-time PCR are provided. The real-time PCR protocol is an excellent tool for reliable quantification of in vitro drug screening and evaluation protocols to determine the efficacy of potential anti-viral agents. Quantification using these simultaneous PCR cycle threshold (Ct) detection techniques during one-step real-time RT-PCR (Applied Biosystems, CA) eliminates the variability resulting from quantification of end-point RT-PCR products. In addition, the mitochondrial toxicity assay is an added tool to assess potential side-effects for these chemotherapeutic agents.

13 Claims, 14 Drawing Sheets

Analysis of Mitochondrial Nucleic Acid Levels
in Huh7 Cells After a 7-Day Incubation Period Changes in mit.DNA Changes in mit. RNA PSI-A does not change the mitochondrial COXII nucleic acid levels
in Huh7 cells after a 7-day incubation period.

FOREIGN PATENT DOCUMENTS

| EP | 01202168.9 | 8/2002 |
|---|---|---|
| EP | 1229130 | 8/2002 |
| WO | 97/39149 | 10/1997 |
| WO | WO 9947706 A1 * | 9/1999 |
| WO | 99/51776 | 10/1999 |
| WO | 99/66075 | 12/1999 |
| WO | 00/44935 | 8/2000 |
| WO | 00/44936 | 8/2000 |
| WO | 00/68436 | 11/2000 |
| WO | 01/66799 | 9/2001 |
| WO | 02/46470 | 6/2002 |
| WO | 02/097124 | 12/2002 |

OTHER PUBLICATIONS

De Muys, J. et al, "Anti-human immunodeficiency virus type 1 activity, intracellular metabolism, and pharmacokinetic evaluation of 2-deoxy-3'-oxa-4'-thiocytidine," Antimicrobial Agents and Chemotherapy, vol. 43, No. 8, pp. 1835-1844 (Aug. 1999).

Abe, A. et al., "Quantification of hepatitis B virus genomic DNA by real-time detection PCR," J. Clin. Microbiol., 37:2899-2903 (1999).

Aberham, C. et al., "A quantitative, internally controlled real-time PCR Assay for the detection of parvovirus B19 DNA," J. Virol. Methods, 92:183-191 (2001).

Bisset, L.R., et al., "Quantification of in vitro retroviral replication using a one-tube real-time RT-PCR system incorporating direct RNA preparation," J. Virol. Methods, 91:149-155 (2001).

Bonnet, G. et al., "Thermodynamic basis of the enhanced specificity of structured DNA probes." Proceedings of the National Academy of Sciences, 96:6171-6176 (1999).

Boultwood, J., et al., "Amplification of mitochondrial DNA in acute myeloid leukaemia," British Journal of Hematology, 95(2):426-431 (Nov. 1996).

Cane, P.A., et al., "Use of real-time PCR and fluorimetry to detect lamivudine resistance-associated mutations in hepatitis B virus," Antimicrob. Agents Chemother., 43:1600-1608 (1999).

Chen, C.H., et al., "Effect of anti-human immunodeficiency virus nucleoside analogs on mitochondrial DNA and its implication for delayed toxicity," Mol. Pharmacol., 39:625-628 (1991).

Cubie, H.A., et al., "Rapid real time PCR to distinguish between high risk human papillomavirus types 16 and 18," Mol. Pathol., 54:24-29 (2001).

Dekok, J.B., et al., "Use of real-time quantitative PCR to compare DNA isolation methods," Clin. Chem., 44:2201-2204 (1998).

Desire, N., et al., "Quantification of human immunodeficiency virus type 1 proviral load by a TaqMan real-time PCR assay," J. Clin. Microbiol., 39:1303-1310 (2001).

Desjardin, L.E., et al., "Measurement of sputum mycobacterium tuberculusis messenger RNA as a surrobgate for response to chemotherapy," American Journal of Respiratory and Crotocal Care Medicine, 160(1):203-210 (Jul. 1999).

Dutschman, et al., "Metabolism of 2', 3' —dideoxy-2', 3'-didehydro-beta-L(-)-5-fluorocytidine and its activity in combination with clinically approved anti-Human Immunodeficiency Virus beta-D(+) nucleoside analogs in vitro," Antimicrob. Agents Chemother., 42:1799-1804 (1998).

Enger, L. et al., "Cloning and characterization of a complex DNA fingerprinting probe for Candida parapsilosis," J. Clin. Microbiol., 39:658-669 (Feb. 2001).

Ercolani, L., et al., "Isolation and complete sequence of a functional human glyceraldehydes-3-phosphate dehydrogenase gene," J. Biol. Chem., 263(30):15335-15341 (Oct. 1988).

Gault, E., et al., "Quantification of human cytomegalorvirus DNA by real-time PCR," J. Clin., Mirobiol., 39:772-775 (2001).

Gelmini, S., et al., Quantitative polymerase chain reaction-based homogeneous assay with fluorogenic probes to measure c-erB-2 onocogene amplification, Clin. Chem., 43:752-758 (1997).

Gerard, C.J., et al., "Improved quantitation of minimal residual disease in multiple myeloma using real-time polymerase chain reaction and plasmid-DNA complementarity determining region III standards," Cancer Res., 58:3957-3964 (1998).

Gibson, U.E.M., et al., "A novel method for real-time quantitative RT-PCR," Genome Res., 6:995-1001 (1996).

Giesendorf, B.A. et al., "Molecular beacons, a new approach for semiautomated mutation analysis," Clin. Chem., 44, 482-486 (1998).

Gruber, F., et al., "2001. Quantitation of viral DNA by realt-time PCR applying duplex amplification, internal standardization, and two-color fluorescence detection," Appl. Environ. Microbiol., 67:2837-2839 (2001).

Heid, C.A. et al., "Real-time quantitative PCR", Genome Res., 6:986-994 (1996).

Holland, P.M., et al., "Detection of specific polymerase chain reaction product by utilizing the 5'-3' exonuclease activity of Thermus aquaticus DNA polymerase," Proc. Natl., Acad. Sci. USA., 88:7276-7280 (1991).

Ishida, K., et al., "Novel approach to quantitative reverse transcriptase PCR assay of mRNA component in autopsy material using the TaqMan fluorogenic detection system: Dynamics of pulmonary surfactant apoprotein A," Forensic Science International, 113(1-3):127-131 (Sep. 11, 2000).

Jabs, W.J, et al., "Normalized quantification by real-time PCR of Epstein-Barr virus load in patients at risk for postransplant lymphoprolifierative disorders," J. Clin. Microbiol., 39:564-569 (2001).

Joseffson, A.M., et al., Viral load of human papilloma virus 16 as a determinant for development of cervical carcinoma in situ: A nested case-control study, Lancet 335(9222):2189-2193 (Jun. 24, 2000).

Josefsson, A., et al., "Detection and quantitation of human papillomavirus by using the fluorescent 5' exonuclease assay," J. Clin. Microbiol., 37:490-496 (1999).

Ju, J. et al., "Fluorescent energy transfer dye-labeled primers for DNA sequence analysis," Proceedings of the National Academy of Sciences, 92:4347-51 (1995).

Kato, T., et al., "Development of a TT virus DNA quantiafication system using real-time detection PCR," J. Clin. Microbiol., 38:94-98 (2000).

Kearns, A.M. et al., "Development and evaluatin of a real-time quantitative PCR for the detection of human cytomegalovirus," J. Virol. Methods, 95:121-131 (2001).

Kessler, H.H., et al., "Detection of Herpes simplex virus DNA by real-time PCR," J. Clin. Microbiol., 38:2628-2642 (2000).

Kimura, H. et al., "Quantitative analysis of Epstein-Barr virus load by using a real-time PCR assay," J. Clin. Microbiol., 37:132-136 (1999).

Komurian-Pradel, F., et al., "Quantitation of HCV RNA using real-time PCR and fluorimetry," J. Virol. Methods, 95:111-119 (2001).

Kostrikis, L.G., et al., "Spectral genotyping of human alleles," Science, 279:1228-1229 (1998).

Kuimelis, R.G. et al., "Structural analogues of TaqMan probes for real-time quantitative PCR," Nucleic Acids Symp. Ser., 37:255-256 (1997).

Lallemand, F., et al., "Quantitative analysis of human herpesvirus 8 viral load using a real-time PCR assay," J. Clin. Micrbial., 38:1404-1408 (2000).

Leone, G. et al., "Molecular beacon probes combined with amplification by NASBA enable homogeneous, real-time detection of RNA," Nucleic Acids Res., 26:2150-2155 (1998).

Lewin, S.R., et al., "1999. Use of real-time PCR and molecular beacons to detect virus replication in human immunodeficiency virus type 1-infected individuals on prolonged effective antiretroviral therapy," J. Virol., 73:6099-6103 (1999).

Livak, K.J., et al., "Oligonucleotides with fluorescent dyes at opposite ends provide a quenched probe system useful for detecting PCR product and nucleic acid hybridization," PCR Methods Appl., 4:357-362 (1995).

Locatelli, G., et al., "Real-time quantitative PCR for human herpesvirus 6 DNA," J. Clin. Microbiol., 37:4042-4048 (2000).

Lockey, C. et al., "Real-time fluorescence detection of a single DNA molecule," Biotechniques, 24:744-746 (1998).

Machida, U., et al., "Real-time automated PCR for early diagnosis and monitoring of cyto-megalovirus infection after bone marrow transplantation," J. Clin. Microbiol., 38:2536-2542 (2000).

Marcucci, G., et al., "Detection of minimal residual disease in patients with AML1/ETO-associated acute myeloid leukemia using a novel quantitative reverse transcription polymerase chain reaction assay," Leiukemia, 12:1482-1489 (1998).

Marras, S.A., et al., "Multiplex detection of single-nucleotide variations of using molecular beacons," Genet. Anal., 14:151-156 (1999).

Martell, M., et al., "High-throughput real-time reverse transcription-PCR quantitation of hepatis C virus RNA," J. Clin Microbiol., 37:327-332 (1999).

Matsuo, T., "In situ visualization of mRNA for basic fibroblast growth factor in living cells," Biochimica Biophysica Acta, 1379:178-184 (1998).

McGoldrick, A., et al., "A novel approach to the detection of classical swine fever virus by RT-PCR with a fluorogenic probe (TaqMan),"J. Virol. Methods, 72:125-135 (1998).

Mensink, E., et al., "Quantitation of minimal residual disease in Philadelphia chromosome positive chronic myeloid leukaemia patients using real-time quantitiative RT-PCR", British Journal of Haematology, 102(3):768-774 (Aug. 1998).

Morris, T. et al., "Rapid reverse transcription-PCR detection of hepatitis C virus RNA in serum by using the TaqMan fluorogenic detection system," J. Clin. Microbiol.., 34:2933-2936 (1996).

Najioullah, F., et al., "Development of a real-time PCR procedure including an internal control for measurement of HCMV viral load," J. Virol. Methods, 92:55-64 (2001).

Nazarenko, I.A., et al., "A closed tube format for amplification and detection of DNA based on energy transfer," Nucleic Acids Research, 25:2516-2521 (1997).

Ng, S.Y. et al., "Evolution of functional human beta-actin genene and its multi-pseudogene family: Conservation of noncoding regions and chromosomal dispersion of pseudogenes," Molec. & Cell. Biol., 5(10):2720-2732 (Oct. 1985).

Nicoll, S, et al., "Detection of herpes viruses in clinical samples using real-time PCR," J. Virol. Methods, 96:25-31 (2001).

Niesters, H.G., et al., "Development of a real-time quantitative assay for detection of Epstein-barr virus," J. Clin. Microbiol., 38:712-715 (2000).

Nitschje, A., et al., "Detection of human cytomegalovirus DNA by real-time quantitative PCR," J. Clin. Microbiol., 38:2734-2737 (20000.

Nuovo, G.J. et al., "In situ amplification using universal energy transfer-labeled primers," J. Histochem. & Cytochem., 47:273-279 (1999).

Oberst, R.D. , et al., "PCR-based DNA amplification and presumptive detection of *Excherichia coli* O157:H7 with an internal fluorogenic probe and the 5' nuclease (TaqMan) assay," Applied and Environmental Microbiology, 64:3389-96 (1998).

Ohyashiki, J.H., et al., "Use of real-time PCR to monitor human herpesvirus 6 reactivation after allogenic bone marrow transplantation," Int. J. Mol. Med., 6:427-432 (2000).

Ojala, D., et al., "tRNA punctuation model of RNA processing in human mitochondria," Nature, 290;470-474 (Apr. 1981).

Overbergh, L., et al., "Quantification of murine cytokine mRNA's using real-time quantitative reverse transcriptase PCR," Cytokine, 11(4):305-312 (Apr. 1999).

P.E. Applied Systems (Division of Perkin-Elmer Corporation), User Bulletin #2: ABI Prism 700 Sequence Detection System, pp. 1-36 (1997).

Pan-Zhou, X.R., et al., "Differential effects of antiretroviral nucleosides analogs on mitochondrial functionin HepG2 cells," Antimicrob. Agents Chemother., 44(3):496-503 (Mar. 2000).

Pevenstein, S.R., et al., "Quantitation of latent varicella-zoster virus and herpes simplex virus genomes in human trigeminal ganglia," J. Virol, 73:10514-10548 (1999).

Ratge, D., et al., "High-speed detection of blood-borne hepatitis C virus RNA by single-tube real-time fluorescence reverse transcription-PCR with the LightCycler," Clin. Chem., 46:1987-1989 (2000).

Saha, B.K., et al., "Quantitation of HIV-1 by real-time PCR with a unique fluorogenic probe," J. Virol Methods, 93:33-42 (2001).

Sauleda, S., et al., "Profiles of GBV-C/hepatitis G virus markers in patients coinfected with hepatitis C virus," J. Med. Virol., 59:45-51 (1999).

Schutten, M., et al., "Development of a real-time quantitative RT-PCR for the detection of HIV-2 RNA in plasma," J. Virol. Methods, 88:81-87 (2000).

Shikuma, C., et al., "Subcutaneous adipose tissue mitochondria DNA analysis from individuals with HAART-associated lipodystrophy", International Medical Press, Antiviral Therapy 2000; 5 (supplement 5):6.

Shikuma, C., et al., "Mitochondrial DNA decrease in subcutaneous adipose tissue of HIV infected individuals with peripheral lipoatrophy", AIDS 2001, 15: 1801-1809.

Sokol, D.L., et al., "Real time detection of DNA-RNA hybridization in living cells," Proc. Natl Acad. Sci. U.S.A., 95:11538-11543 (1998).

Stuyver, L. et al., "Using real time PCR to determine anti-HIV-1 activity and mitochondrial toxicity of nucleoside analogs" Antiviral Research, vol. 51, No. 1, Jul. 2001, 53-54.

Suryanarayana, K., et al., "Plasma SIV RNA viral load determination by real-time quantification of product generation in reverse transcriptase-polymerase chain reaction." ADIS Res. Hum Retroviruses, 14:183-189 (1998).

Swan, D.C., et al., "A sensitive, type-specific, fluorogenic probe assay for detection of human papillomavirus DNA," J. Clin. Microbiol., 35:886-891 (1997).

Takeuchi, T., et al., Real-time detection system for quantification of hepatatis C virus genome, Gastroenterology, 116:636-642 (1999).

Tanaka, N., et al., "Quantitative analysis of cytomegalovirus load using a real-time PCR assay," J. Med. Virol., 60:455-462 (2000).

Tapp, I., et al., "Homogenous scorning of single-nucleotide polymorphisms: Comparison of the 5'-nuclease TaqMan assay and Molecular Beacon probes," Biotechniques, 28:732-738 (Apr. 2000).

Tepper, et al., "Resistance of mitochondrial DNA to degradation characterizes the apoptotic but not the necrotic mode of human leukemia cell death," Journal of Cellular Biochemistry, 52(3):352-361 (Jul. 1993).

Thomas, A.W., et al., "Differential expression of mRNA in human thyroid cells depleted of mitochondrial DNA by ethidium bromide treatment," Clin. Sci., 97(2):207-213 (Aug. 1999).

Tyagi, G., et al., "Molecular beacons: probes that fluoresce upon hybridization," Nat. Biotechnol., 14:303-308 (1996).

Tyagi, S., et al., "Multicolor molecular beacons for allele discrimination," Nat. Biotechnol., 16:49-53 (1998).

Van Elden, L.J., et al., "Simultaneous detection of influenza viruses A and B using real-time quantitative PCR," J. Clin. Microbial., 39:196-200 (2001).

Vet, J.A., et al., "Multiplex detection of four pathogenic retroviruses using molecular beacons," Proc. Natl. Acad. Sci. U.S.A., 96:6394-6399 (1999).

Wagner, H.J., et al., "Real-time polymerase chain reaction (RQ-PCR) for the monitoring of Epstein-Barr virus (EBV) load in peripheral blood mononuclear cells," Klin. Padiatr., 212:206-210 (2000).

Walker, N.J., "2001. Real-time quantitiative PCR: applications to mechanism-based toxicology," J. Biochem. Mol. Toxicol., 15:121-127 (2001).

White, I.E., et al., "Quanitation of cell-free and cell-associated Kaposi's sarcoma-associated herpesvirus DNA by real-time PCR," J. Clin. Microbiol., 38:1992-1995 (2000).

Zhang, Hao "Quantitation of Mitochondrial DNA in Human Lymphoblasts by a Competitive Polymerase Chain Reaction Method: Application to the Study of Inhibitors of Mitochondrial DNA Content"; Copyright © by The American Society for Pharmacology and Experimental Therapeutics; Molecular Pharmacology, 46: 1063-1069, 1994.

Chariot, Journal of Hepatology, Zidovudine-induced mitochondrial disorder with masive liver steatosis myopathy, lactic acidosis, and mitochondrial DNA depletion, 30:156-160, 1999.

International Search Report for PCT/US01/47223, published Aug. 21, 2003.

Claudio et al., "A stop-codon mutation in the human mtDNA cytochrome c oxidase I gene disrupts the functional structure of complex IV", American Journal of Human Genetics, 65: No. 3, Sep. 1999, 611-620.

* cited by examiner

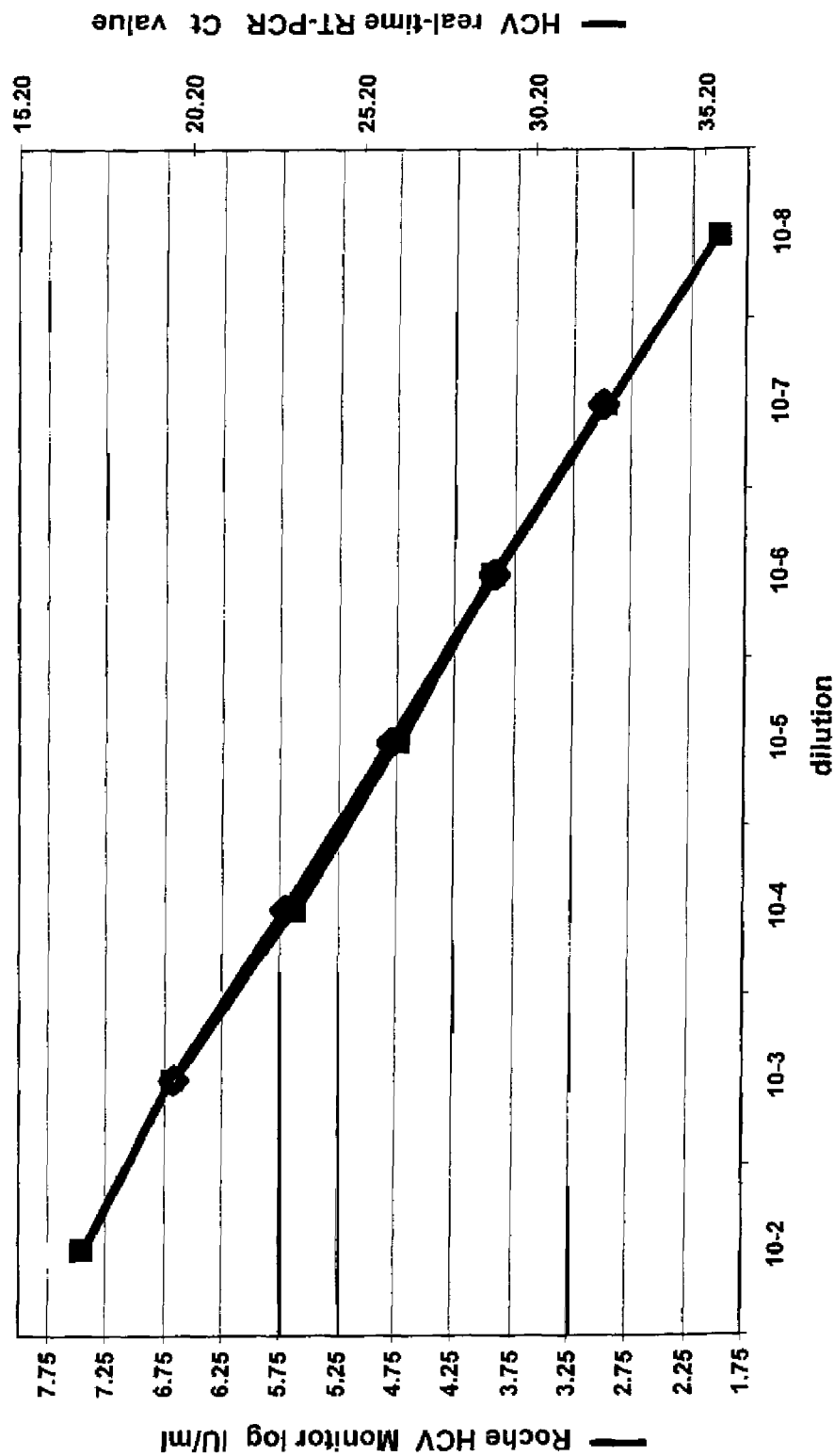
Figure 1B: Conversion Plot for HCV RNA Quantification; from Real-Time RT-PCR Ct Values to IU/ml

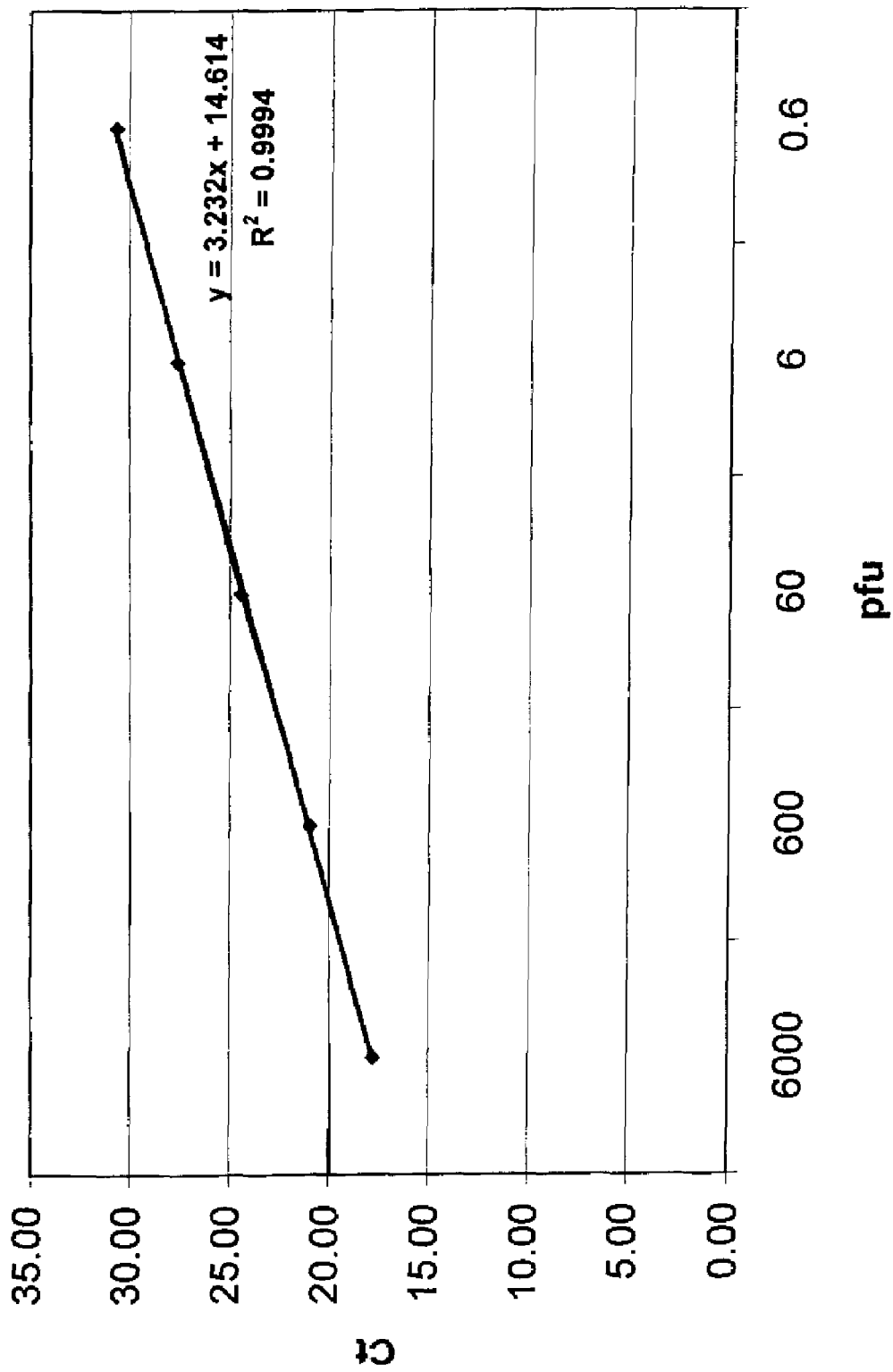

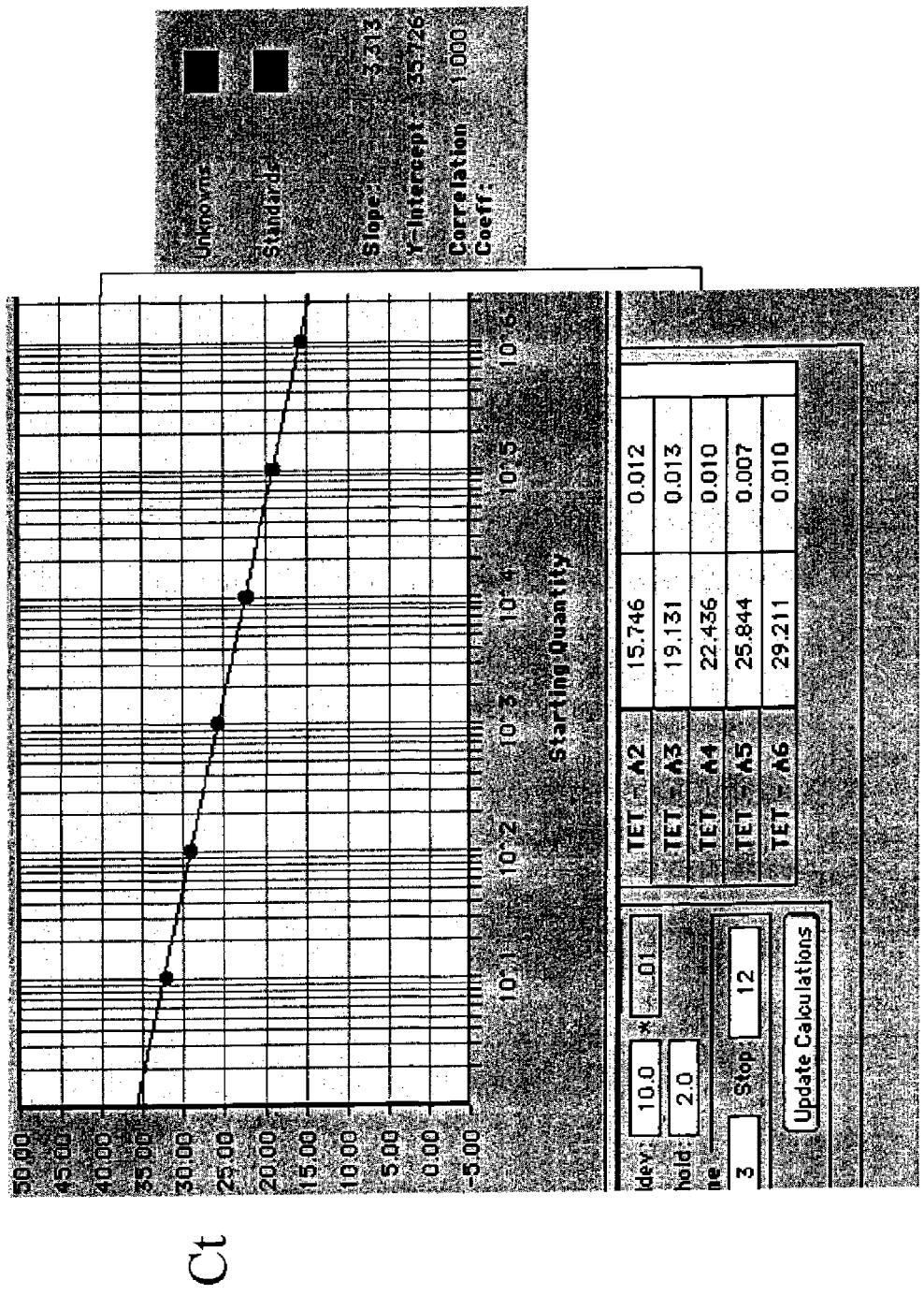
Figure 1D: Standard Curve for Mitochondrial DNA

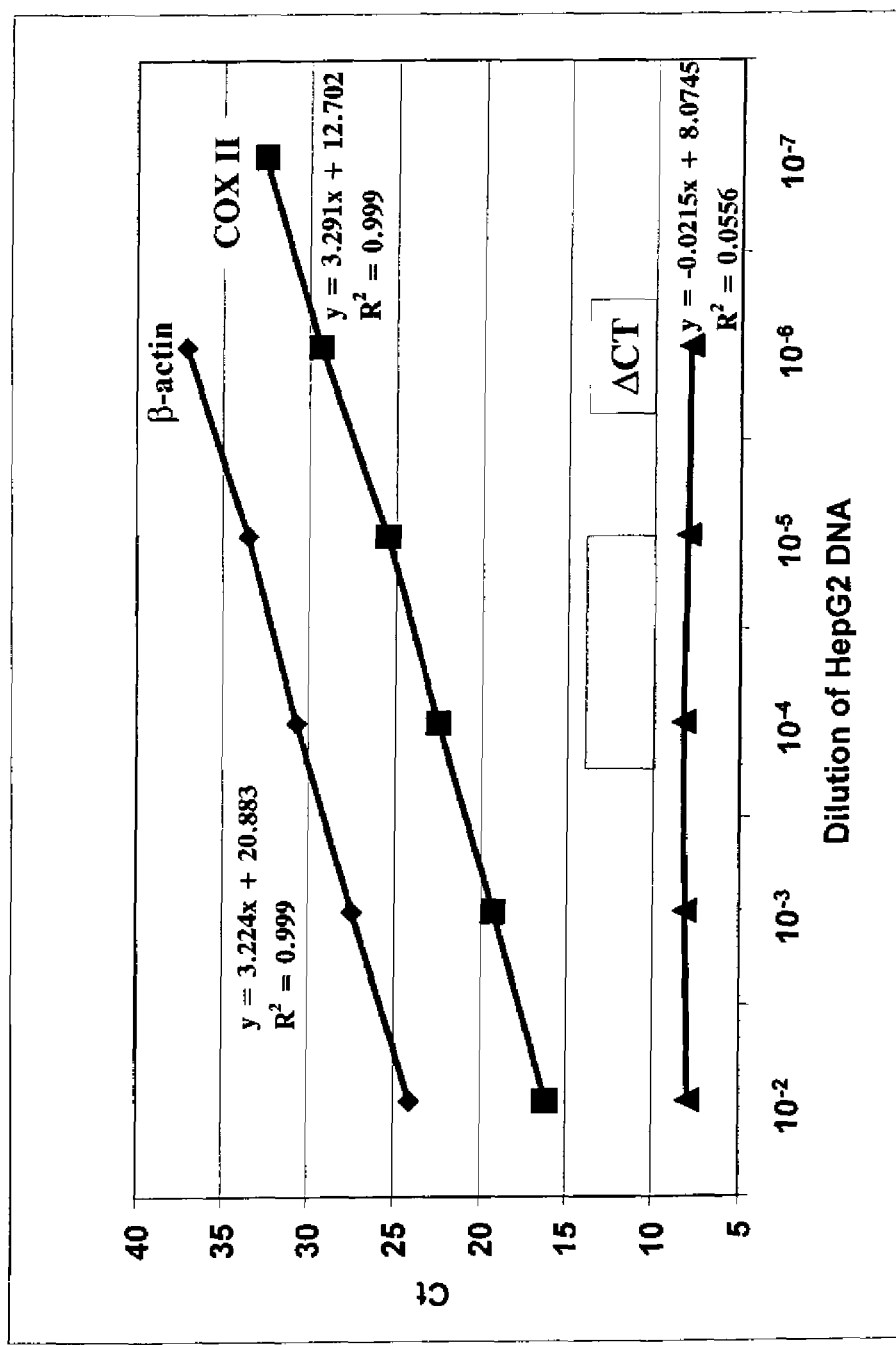
Figure 1E: Standard Curves and DCt Value for the Molecular Toxicology Approach Figure 7: Genome Organization of HCV and the HCV Replicon Figure 8: Changes in Cellular and Viral Nucleic Acids over a 7-Day Incubation Period in Huh7/HCV Replicon Cells

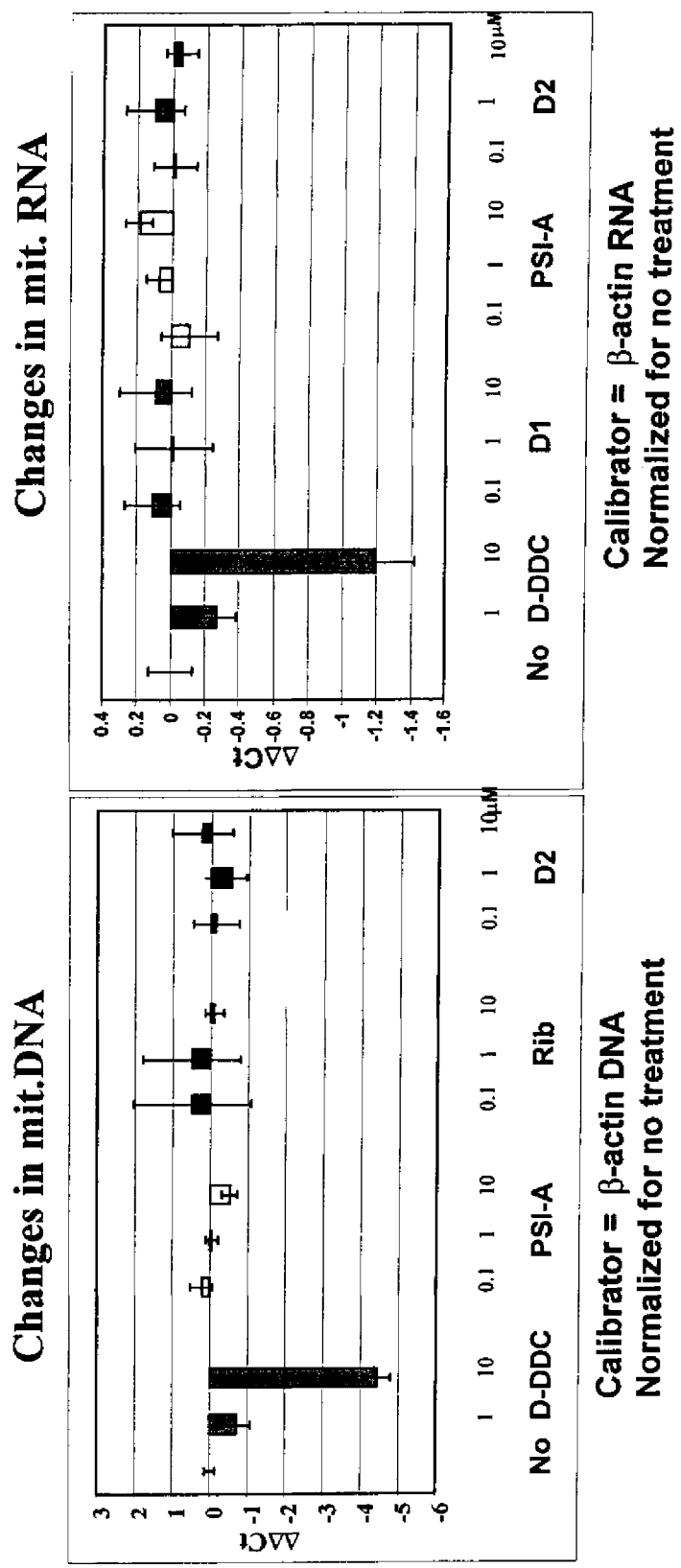
Figure 10: Analysis of Mitochondrial Nucleic Acid Levels in Huh7 Cells After a 7-Day Incubation Period
PSI-A does not change the mitochondrial COXII nucleic acid levels in Huh7 cells after a 7-day incubation period.

SEQUENCE LISTING

<160> NUMBER OF SEQ ID NOS: 29

<210> SEQ ID NO 1
<211> LENGTH: 17
<212> TYPE: DNA
<213> ORGANISM: Artificial Sequence
<220> FEATURE:
<223> OTHER INFORMATION: Oligonucleotides used to amplify b-actin
      (primers) sense

<400> SEQUENCE: 1
gcgcggctac agcttca                                                    17

<210> SEQ ID NO 2
<211> LENGTH: 22
<212> TYPE: DNA
<213> ORGANISM: Artificial Sequence
<220> FEATURE:
<223> OTHER INFORMATION: Oligonucleotides used to amplify b-actin
      (primers) antisense

<400> SEQUENCE: 2
tctccttaat gtcacgcacg at                                              22

<210> SEQ ID NO 3
<211> LENGTH: 18
<212> TYPE: DNA
<213> ORGANISM: Artificial Sequence
<220> FEATURE:
<223> OTHER INFORMATION: Labeled oligonucleotide (probe) used to detect
      host nucleic acid

<400> SEQUENCE: 3
caccacggcc gagcggga                                                   18

<210> SEQ ID NO 4
<211> LENGTH: 23
<212> TYPE: DNA
<213> ORGANISM: Artificial Sequence
<220> FEATURE:
<223> OTHER INFORMATION: HIV-1 (primers) sense

<400> SEQUENCE: 4
tgggttatga actccatcct gat                                             23

<210> SEQ ID NO 5
<211> LENGTH: 23
<212> TYPE: DNA
<213> ORGANISM: Artificial Sequence
<220> FEATURE:
<223> OTHER INFORMATION: HIV-1 (primers) antisense

<400> SEQUENCE: 5
tgtcattgac agtccagctg tct                                             23

<210> SEQ ID NO 6
<211> LENGTH: 31
<212> TYPE: DNA
<213> ORGANISM: Artificial Sequence
<220> FEATURE:
<223> OTHER INFORMATION: Oligonucleotide (probe) used to detect HIV-1
      viral load

<400> SEQUENCE: 6
tttctggcag ctctcggctg tactgtccat t                                    31

-continued

<210> SEQ ID NO 7
<211> LENGTH: 24
<212> TYPE: DNA
<213> ORGANISM: Artificial Sequence
<220> FEATURE:
<223> OTHER INFORMATION: Oligonucleotides used to amplify HCV (primers)
      sense

<400> SEQUENCE: 7
agccatggcg ttagtataga gtgt                                              24

<210> SEQ ID NO 8
<211> LENGTH: 18
<212> TYPE: DNA
<213> ORGANISM: Artificial Sequence
<220> FEATURE:
<223> OTHER INFORMATION: Oligonucleotides used to amplify HCV (primers)
      antisense

<400> SEQUENCE: 8
ttccgcagac cactatgg                                                     18

<210> SEQ ID NO 9
<211> LENGTH: 20
<212> TYPE: DNA
<213> ORGANISM: Artificial Sequence
<220> FEATURE:
<223> OTHER INFORMATION: Oligonucleotide (probe) used to detect HCV
      viral load

<400> SEQUENCE: 9
cctccaggac cccccctccc                                                   20

<210> SEQ ID NO 10
<211> LENGTH: 23
<212> TYPE: DNA
<213> ORGANISM: Artificial Sequence
<220> FEATURE:
<223> OTHER INFORMATION: Oligonucleotides used to amplify BVDV (primers)
      sense

<400> SEQUENCE: 10
agtcttcagt tcttgctga tgt                                                23

<210> SEQ ID NO 11
<211> LENGTH: 20
<212> TYPE: DNA
<213> ORGANISM: Artificial Sequence
<220> FEATURE:
<223> OTHER INFORMATION: Oligonucleotides used to amplify BVDV (primers)
      antisense

<400> SEQUENCE: 11
tgttgcgaaa ggaccaacag                                                   20

<210> SEQ ID NO 12
<211> LENGTH: 27
<212> TYPE: DNA
<213> ORGANISM: Artificial Sequence
<220> FEATURE:
<223> OTHER INFORMATION: Labeled oligonucleotide (probe) used to detect
      BVDV viral load

<400> SEQUENCE: 12
aaatcctcct aacaagcggg ttccagg                                           27

```
<210> SEQ ID NO 13
<211> LENGTH: 20
<212> TYPE: DNA
<213> ORGANISM: Artificial Sequence
<220> FEATURE:
<223> OTHER INFORMATION: Oligonucleotides used to amplify HBV (primers)
      sense

<400> SEQUENCE: 13
ggacccctgc tcgtgttaca                                                    20

<210> SEQ ID NO 14
<211> LENGTH: 24
<212> TYPE: DNA
<213> ORGANISM: Artificial Sequence
<220> FEATURE:
<223> OTHER INFORMATION: Oligonucleotides used to amplify HBV (primers)
      antisense

<400> SEQUENCE: 14
gagagaagtc caccacgagt ctag                                               24

<210> SEQ ID NO 15
<211> LENGTH: 30
<212> TYPE: DNA
<213> ORGANISM: Artificial Sequence
<220> FEATURE:
<223> OTHER INFORMATION: Oligonucleotide (probe) used to detect HBV
      viral load

<400> SEQUENCE: 15
tgttgacaaa gtcctcacaa taccagcaga                                         30

<210> SEQ ID NO 16
<211> LENGTH: 25
<212> TYPE: DNA
<213> ORGANISM: Artificial Sequence
<220> FEATURE:
<223> OTHER INFORMATION: Oligonucleotides used to amplify RSV (primers)
      sense

<400> SEQUENCE: 16
caacaaccct aatcatgtgg tatca                                              25

<210> SEQ ID NO 17
<211> LENGTH: 18
<212> TYPE: DNA
<213> ORGANISM: Artificial Sequence
<220> FEATURE:
<223> OTHER INFORMATION: Oligonucleotides used to amplify RSV (primers)
      antisense

<400> SEQUENCE: 17
ccggttgcat tgcaaaca                                                      18

<210> SEQ ID NO 18
<211> LENGTH: 35
<212> TYPE: DNA
<213> ORGANISM: Artificial Sequence
<220> FEATURE:
<223> OTHER INFORMATION: Oligonucleotide (probe) used to detect RSV
      viral load

<400> SEQUENCE: 18
tgacaggcaa agaaagagaa ctcagtgtag gtaga                                   35
```

```
<210> SEQ ID NO 19
<211> LENGTH: 17
<212> TYPE: DNA
<213> ORGANISM: Artificial Sequence
<220> FEATURE:
<223> OTHER INFORMATION: Oligonucleotides used to amplify mitochondrial
      nucleic acid (primers) sense

<400> SEQUENCE: 19
tgcccgccat catccta                                                    17

<210> SEQ ID NO 20
<211> LENGTH: 24
<212> TYPE: DNA
<213> ORGANISM: Artificial Sequence
<220> FEATURE:
<223> OTHER INFORMATION: Oligonucleotides used to amplify mitochondrial
      nucleic acids (primers) sense

<400> SEQUENCE: 20
tcgtctgtta tgtaaaggat gcgt                                            24

<210> SEQ ID NO 21
<211> LENGTH: 21
<212> TYPE: DNA
<213> ORGANISM: Artificial Sequence
<220> FEATURE:
<223> OTHER INFORMATION: Oligonucleotide (probe) used to detect host
      nucleic acid

<400> SEQUENCE: 21
tcctcatcgc cctcccatcc c                                               21

<210> SEQ ID NO 22
<211> LENGTH: 33
<212> TYPE: DNA
<213> ORGANISM: Artificial Sequence
<220> FEATURE:
<223> OTHER INFORMATION: HIV-1 RT domain probe sequence
<220> FEATURE:
<221> NAME/KEY: modified_base
<222> LOCATION: (1)..(1)
<223> OTHER INFORMATION: n is t modified by binding to a fluorescent dye
      molecule
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: modified_base
<222> LOCATION: (33)..(33)
<223> OTHER INFORMATION: n is t modified by binding to a fluorescent dye
      molecule
<220> FEATURE:
<221> NAME/KEY: misc_feature
<222> LOCATION: (33)..(33)
<223> OTHER INFORMATION: n is a, c, g, or t

<400> SEQUENCE: 22
nttctggcag cactataggc tgtactgtcc atn                                  33

<210> SEQ ID NO 23
<211> LENGTH: 18
<212> TYPE: DNA
<213> ORGANISM: Artificial Sequence
<220> FEATURE:
<223> OTHER INFORMATION: Probe for nuclear gene
<220> FEATURE:
<221> NAME/KEY: modified_base
<222> LOCATION: (1)..(1)
<223> OTHER INFORMATION: n is c modified by binding to a fluorescent dye
``` molecule
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: modified_base
<222> LOCATION: (18)..(18)
<223> OTHER INFORMATION: n is a modified by binding to a fluorescent dye
      molecule
<220> FEATURE:
<221> NAME/KEY: misc_feature
<222> LOCATION: (18)..(18)
<223> OTHER INFORMATION: n is a, c, g, or t

<400> SEQUENCE: 23
naccacggcc gagcgggn                                                       18

<210> SEQ ID NO 24
<211> LENGTH: 21
<212> TYPE: DNA
<213> ORGANISM: Artificial Sequence
<220> FEATURE:
<223> OTHER INFORMATION: Fluorescent labeled probes for mitochondrial
      genome
<220> FEATURE:
<221> NAME/KEY: modified_base
<222> LOCATION: (1)..(1)
<223> OTHER INFORMATION: n is t modified by binding to a fluorescent dye
      molecule
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: modified_base
<222> LOCATION: (21)..(21)
<223> OTHER INFORMATION: n is c modified by binding to a fluorescent dye
      molecule
<220> FEATURE:
<221> NAME/KEY: misc_feature
<222> LOCATION: (21)..(21)
<223> OTHER INFORMATION: n is a, c, g, or t

<400> SEQUENCE: 24
ncctcatcgc cctcccatcc n                                                   21

<210> SEQ ID NO 25
<211> LENGTH: 27
<212> TYPE: DNA
<213> ORGANISM: Artificial Sequence
<220> FEATURE:
<223> OTHER INFORMATION: TaqMan probe molecule
<220> FEATURE:
<221> NAME/KEY: modified_base
<222> LOCATION: (1)..(1)
<223> OTHER INFORMATION: n is a modified by binding to a 6-FAM
      fluorophore
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: modified_base
<222> LOCATION: (27)..(27)
<223> OTHER INFORMATION: n is g modified by binding to a TAMRA
      fluorophore
<220> FEATURE:
<221> NAME/KEY: misc_feature
<222> LOCATION: (27)..(27)
<223> OTHER INFORMATION: n is a, c, g, or t

<400> SEQUENCE: 25
naatcctcct aacaagcggg ttccagn                                             27

<210> SEQ ID NO 26
<211> LENGTH: 23
<212> TYPE: DNA
<213> ORGANISM: Artificial Sequence
<220> FEATURE:
<223> OTHER INFORMATION: Oligonucleotides used to amplify BVDV (primers) sense

<400> SEQUENCE: 26
agccttcagt ttcttgctga tgt                                    23

<210> SEQ ID NO 27
<211> LENGTH: 20
<212> TYPE: DNA
<213> ORGANISM: Artificial Sequence
<220> FEATURE:
<223> OTHER INFORMATION: TaqMan probe primers antisense

<400> SEQUENCE: 27
tgttgcgaaa gcaccaacag                                        20

<210> SEQ ID NO 28
<211> LENGTH: 23
<212> TYPE: DNA
<213> ORGANISM: Artificial Sequence
<220> FEATURE:
<223> OTHER INFORMATION: Combination of HCV RNA purification with real-time RT-PCR prime

<400> SEQUENCE: 28
agccatggcg ttagtatgag tgt                                    23

<210> SEQ ID NO 29
<211> LENGTH: 20
<212> TYPE: DNA
<213> ORGANISM: Artificial Sequence
<220> FEATURE:
<223> OTHER INFORMATION: Labeled oligonucleotide (probe) used to detect HCV viral load
<220> FEATURE:
<221> NAME/KEY: modified_base
<222> LOCATION: (1)..(1)
<223> OTHER INFORMATION: n is c modified by binding to a 6-FAM fluorophore
<220> FEATURE:
<221> NAME/KEY: misc_feature
<222> LOCATION: (1)..(1)
<223> OTHER INFORMATION: n is a, c, g, or t
<220> FEATURE:
<221> NAME/KEY: modified_base
<222> LOCATION: (20)..(20)
<223> OTHER INFORMATION: n is c modified by binding to a TAMRA fluorophore
<220> FEATURE:
<221> NAME/KEY: misc_feature
<222> LOCATION: (20)..(20)
<223> OTHER INFORMATION: n is a, c, g, or t

<400> SEQUENCE: 29
nctccaggac cccccctccn                                        20

KIT FOR ASSESSING MITOCHONDRIAL TOXICITY

This application is a divisional U.S. application Ser. No. 10/854,870, filed May 27, 2004, now abandoned, which is a continuation of U.S. application Ser. No. 10/008,140, filed Oct. 18, 2001, now abandoned, which claims priority to U.S. Provisional Application No. 60/241,488, filed Oct. 18, 2000, U.S. Provisional Application No. 60/256,067, filed Dec. 15, 2000, and U.S. Provisional Application No. 60/282,156, filed Apr. 6, 2001.

FIELD OF THE INVENTION

This application is in the area of processes for the detection and analysis of viral infections and mitochondrial toxicity, and for processes for the identification of active compounds for the treatment of viral infections and processes to measure mitochondrial toxicity resulting from drug therapies.

BACKGROUND OF THE INVENTION

The detection and quantification of nucleic acid sequences is of importance for a wide range of applications. The most widely used method to detect nucleic acids are based on the polymerase chain reaction (PCR). PCR is used to amplify a segment of DNA flanked by stretches of known sequences. Two oligonucleotides binding to these known flanking sequences are used as primers for a series of in vitro reactions that are catalyzed by a DNA polymerase. These oligonucleotides typically have different sequences and are complementary to sequences that lie on opposite strands of the template DNA and flank the segment of DNA that is to be amplified. The template DNA is first denatured by heat in the presence of a large molar excess of each of the two oligonucleotides and the four 2'-deoxynucleotide triphosphates. The reaction mixture is then cooled to a temperature that allows the oligonucleotide primers to anneal to their target sequences. Afterwards, the annealed primers are extended by the DNA polymerase. The cycle of denaturation, annealing, and DNA-synthesis is then repeated about 10 to 50 times. Since the products of one cycle are used as a template for the next cycle the amount of the amplified DNA fragment is theoretically doubled with each cycle resulting in a PCR-efficiency of 100%.

"Real-time PCR" refers to a polymerase chain reaction that is monitored, usually by fluorescence, over time during the amplification process, to measure a parameter related to the extent of amplification of a particular sequence, such as the extent of hybridization of a probe to amplified target sequences. The DNA generated within a PCR is detected on a cycle by cycle basis during the PCR reaction. The amount of DNA increases faster the more template sequences are present in the original sample. When enough amplification products are made a threshhold is reached at which the PCR products are detected. Thus amplification and detection are performed simultaneously in the same tube.

In biological research, PCR has accelerated the study of testing for communicable diseases. Medical applications of PCR include identifying viruses, bacteria and cancerous cells in human tissues. PCR can even be used within single cells, in a procedure called in situ (in-site) PCR, to identify specific cell types. PCR can also be applied to the amplification of RNA, a process referred to as reverse transcriptase PCR (RT-PCR). RT-PCR is similar to regular PCR, with the addition of an initial step in which DNA is synthesized from the RNA target using an enzyme called a reverse transcriptase. A wide variety of RNA molecules have been used in RT-PCR, including ribosomal RNA, messenger RNA and genomic viral RNA.

PCR itself is quite simple, but sample preparation can be laborious. The goals of sample preparation include the release of nucleic acid (DNA or RNA), concentration of the nucleic acid to a small volume for PCR, and removal of inhibitors of PCR. Inhibitors of PCR are naturally occurring substances which reduce the efficiency of PCR, and which are often present in clinical samples. When the specimen contains a large amount of target nucleic acid, sample preparation is trivial. But sample preparation is more difficult in most clinical specimens, particularly when a large volume specimen must be processed and only a few pathogens are present. Complex protocols are often required.

Since PCR detects the presence or absence of a particular nucleic acid target, it will only detect a pathogen if its nucleic acid is present in the particular specimen. PCR detects nucleic acids from living or dead microbes. This must be recognized if PCR is used to monitor response to therapy. PCR provides at most nucleic acid sequence information. PCR can be used to screen for drug resistance mutations, but it does not provide direct antibiotic susceptibility data.

Appropriate controls are necessary when PCR is used diagnostically. These include negative controls, positive controls and specificity controls. Negative controls (no target DNA) are needed to detect contamination. Contamination can occur during sample preparation or reagent mixing, so negative controls need to be processed in parallel with clinical samples. Negative controls should be interspersed among the samples to detect cross-contamination from sample to sample. Contamination is frequently intermittent; a sufficient number of negative controls must be included to detect low rates of contamination. Most published studies have not included a sufficient number of negative controls.

Positive controls include a small number of target DNA copies. Positive controls are needed to ensure efficient release of target DNA from pathogens, to guard against loss of DNA during sample processing, and to identify the presence of inhibitors (natural substances sometimes present in clinical samples that reduce PCR efficiency). Positive controls should be processed in parallel with clinical specimens. Clinical specimens vary in the presence of inhibitors of PCR, and it may be necessary to add an internal positive control for each sample. The internal positive controls have the same recognition sites as the target DNA, but are designed with some difference in the internal sequence. Amplification of the internal positive controls can be distinguished from that of the real target DNA.

Specificity controls are needed to determine the range of target DNAs that will be amplified by the PCR assay. For assays designed to detect pathogens in clinical samples, human DNA samples must be tested to ensure that the PCR primers do not recognize a human DNA target by chance. Related pathogens must be tested to determine the range of species/strains that will be amplified. Specificity controls are needed only once, when a new PCR assay is designed. Negative and positive controls must be included every time samples are processed, and should be processed simultaneously with the clinical samples.

PCR has been used in three broad categories of diagnostic procedures, namely detection, characterization and quantification.

Detection is the most difficult PCR procedure, especially when the number of pathogens in the specimen is low. The PCR must be conducted under conditions of high sensitivity. Many temperature cycles are used, or a nested protocol is used in which the products from the first reaction are reamplified with a second set of primers. This makes PCR for detection especially prone to carryover contamination. Sample preparation may be laborious, as there is an attempt to process as large a specimen volume as possible. Inhibitors of PCR occur naturally in many clinical samples, and are a major limitation. Numerous positive and negative controls must be included as described above.

In a characterization procedure, nucleic acid variants are identified based on the nucleic acid sequence between the two PCR primers. Many techniques can be used to detect variable sequences, including length polymorphism, changes in restriction sites, and direct DNA sequencing. This is often the easiest type of PCR to carry out clinically. Ample quantities of nucleic acid target can be present in the specimen, either an already grown bacterial or viral culture or a clinical sample with large numbers of microbes. Goals can include rapid detection of drug resistance mutations, assignment of strains to clinically meaningful phylogenetic groups, or epidemiological tracing.

Quantitation (indicating how many copies of the target nucleic acid are present) has primarily been applied to chronic viral infections, especially hepatitis C virus (HCV) and human immunodeficiency virus (HIV) infections. The level of viremia has prognostic implications, and has been used to demonstrate response to antiviral drugs. PCR is quite sensitive, but it is not inherently quantitative. The amount of the final PCR product is usually similar from an initial sample containing 10 or 10,000 copies. This limitation can be overcome by serial dilution of the clinical sample until no target DNA is detected, or by the addition of synthetic competitor DNA molecules. The competitor molecules have regions complementary to the two primers, but differ in some way from the natural target (e.g., a different length). By comparing the amount of the natural and competitor PCR products, a rough estimation of the number of target molecules in the sample is possible.

PCR has been applied in the research setting to hundreds of pathogens, and has yielded important insights into pathogenesis and epidemiology of many infectious diseases. For clinical purposes, PCR-based diagnostic tests are best applied when the following conditions are fulfilled: (1) The results of the test will make a clear clinical difference and a therapy will be given or withheld based on the results of PCR; (2) routine culture methods are limited because the microbe cannot be grown (e.g., *Mycobacterium leprae*, HCV), grows slowly (e.g., *M. tuberculosis*), or is difficult to culture (e.g., *Brucella* species, HIV); and (3) there is an accessible clinical specimen which contains large numbers of microbes (e.g., blood for HCV or HIV).

PCR has been useful in a variety of chronic virus infections (HIV, HCV, hepatitis B virus, human papillomavirus and cytomegalovirus). PCR has been crucial for the detection of HIV infection in neonates, since maternal antibodies complicate serologic diagnosis. Quantitation of HIV and HCV viremia by PCR has important prognostic implications, and has been used to monitor response to drug therapy. PCR is useful for the rapid diagnosis of pulmonary infections in immunocompromised hosts, particularly for *cytomegalovirus* and *Pneumocystis carinii*.

HIV

The human immunodeficiency virus type-1 (HIV-1) is a retrovirus belonging to the family of the Lentiviridae. One of the characteristic features of this virus group is that the members replicate over a DNA intermediate through the viral encoded reverse transcriptase (RT) enzyme activity. The high replication rate combined with the low fidelity of that reverse transcriptase enzyme provides the virus with an extremely high genomic flexibility. As a consequence, different levels of genetic variability are observed for HIV-1. The epidemic is characterized by the presence of clades within the M-group virus, but there is also an O-group and an N-group virus described, each of them again harboring a variety of clades. Quasispecies populations within the infected individual are also seen. Clinically, there are some important consequences to this quasispecies concept, for example, in vaccine development and immune escape. This concept contributes to the emergence of drug resistant variants that surface under antiviral treatments.

In order to control the course of the disease in infected individuals, potent highly active anti-retroviral therapies (HAART) have been designed. Due to the ongoing replication of the virus, anti-retroviral drug resistance eventually develops, leading to therapy failure. Therefore, there is an ongoing need for more and more potent anti-HIV-1 drugs.

To assess the efficacy of drugs in the treatment of patients in vivo, clinical markers of virus replication needed to be defined. In the past, some surrogate markers, like CD-cell count, have been used. More recently, some commercial assays like Quantiplex (Chiron), NucliSense (Organon-Teknika) and Amplicor HIV-1 Monitor (Roche) were developed to directly measure viral load. These viral load determinations proved to be an excellent tool in monitoring therapeutic efficiency for HAART and for clinical trials with new experimental drugs.

The design of an HIV-1 viral load test is a real challenge. Ideally, a viral load test should fulfill to the following criteria:
  i) be able to detect the huge variability of clades within one group with the same efficiency;
  ii) have a dynamic range of at least five logs or higher; and
  iii) the lower limit of detection should be as low as a few viral copies/mL. Although variability at the PCR-primer binding sites is a real concern in assay development, RT-PCR based assays are considered as the most sensitive technologies.

Mitochondrial Toxicity

Mitochondrial toxicity is clearly recognized as an adverse effect of long-term use of antiviral agents, in particular reverse transcriptase inhibitors. Clinical features of this mitochondrial toxicity vary depending on the tissues that are affected. It is largely dependent on the aerobic metabolism needed for energy supply required for that particular tissue. Most toxic events are reversible at an early stage, however lactic acidosis is often irreversible and can result in death.

The common pathway of antiviral agent induced toxicity is mitochondrial dysfunction. The antiviral agent (most likely the triphosphate form of a nucleoside analogue) inhibits the mitochondrial DNA polymerase γ leading to the loss of mitochondria. This enzyme is essential for the replication of the mitochondrial genome. Tissues with high ATP demand are most susceptible to mitochondrial toxicity.

The mechanism underlying this mitochondrial dysfunction includes failure of energy dependent ionic balance. Subsequently, there is an increase in intracellular calcium, initiating lipolysis and proteolysis, and leading to the accumulation of lactic acid and partial reduction of the respiratory activities.

Since the mitochondrial dysfunction develops over months and symptoms are initially mild, it is important to develop sensitive diagnostic tests that allow determination of the enzyme activity and inhibition by the selected antiviral agent.

Evenly important, new candidate antiviral agents need to be evaluated for their unfavorable DNA polymerase γ inhibiting capacities.

Hepatitis C

Hepatitis C virus (HCV) infection is a pandemic infection, and is a major cause of liver disease. Reports of successful treatment of HCV infection with interferon have increased interest in applications of RT-PCR.

Available tests for HCV infection are limited. Initial serologic tests for HCV had poor sensitivity. Second and third-generation serologic tests have improved sensitivity, but are still not completely dependable. HCV RNA is readily detected in serum using RT-PCR. Viremic patients typically have very high viral titers.

PCR has been applied to the diagnosis of HCV infection in a variety of clinical settings. HCV can be detected as early as one week after infection, and PCR can be used to detect HCV infection during the "window" period between infection and seroconversion. HCV PCR is useful for detecting HCV in seronegative individuals with liver disease. It can be used to confirm maternal to fetal spread of HCV. HCV PCR may be useful in the evaluation of seropositive individuals as candidates for interferon or other therapies. Portions of HCV-seropositive patients are negative by HCV PCR, and may have resolved their infections. PCR-negative individuals have lower serum transaminase concentrations and less histologic activity on liver biopsies. Long-term follow-up studies are needed, but it may be reasonable to withhold therapy from patients with negative HCV PCR results.

The amount of HCV viremia can be determined by either quantitative PCR. PCR is sensitive and is quantitative over a wide range of viral titers. High-titer viremia is correlated with an advanced disease stage. The prognostic value of HCV quantitation awaits prospective studies, but the level of viremia may be useful in selecting candidates for therapy. Quantitative HCV PCR also appears to be useful in monitoring the response to therapy.

WO 00/44936 filed by Bavarian Nordic Research Institute A/S describes a real-time PCR method for the detection and quantification of variants of nucleic acid sequences which differ in the probe-binding site. The method is based in the complete or partial amplification of the same region of the variants and the addition of two or more oligonucleoitde probes to the same PCR mixture, each probe being specific for the probe-binding site of at least one variant.

WO 01/66799 filed by E.I. DuPont Nemours and Company discloses a PCR-based dsDNA quantification method that monitors the fluorescence of a target, whose melting characteristics is predetermined, during each amplification cycle at selected time points. By selecting targets with distinguishing melting curve characteristics, multiple targets can be simultaneously detected.

WO 00/68436 filed by Nationales Zentrum fur Retroviren discloses sequences allowing the detection and quantification of human immunodeficiency virus.

U.S. Pat. No. 6,235,504 assigned to the Rockefeller University describes methods for identifying genetic sequences useful as genomic equivalent markers for organisms.

U.S. Pat. No. 6,210,875 discloses a process for determining the efficacy of antiviral therapy in an HIV-infected host that includes detecting the level of transcriptionally active HIV in the monocytes of the subject at a plurality of times by simultaneously exposing the monocytes to an oligonucleotide probe that specifically binds to at least a portion of HIV mRNA and exposing the monocytes to an antibody, wherein the oligonucleotide probe is labeled with a fluorescent label, comparing the detected HIV levels, and correlating the HIV levels over time with the therapy regimen.

U.S. Pat. No. 5,843,640 discloses an in situ process of simultaneously detecting a specific predetermined nucleic acid sequence and a specific predetermined cellular antigen in the same cell.

Articles describing PCR, including real-time PCR procedures include: Gibson UEM, Heid C A, Williams P M. A novel method for real-time quantitative RT-PCR. Genome Res 1996; 6:995-1001; Heid C A, Stevens J, Livak K J, Williams P M. Real-time quantitative PCR. Genome Res 1996; 6:986-994; Livak K J, Flood S J A, Marmaro J, Giusti W, Deetz K. Oligonucleotides with fluorescent dyes at opposite ends provide a quenched probe system useful for detecting PCR product and nucleic acid hybridization. PCR Methods Appl 1995; 4:357-362; Holland P M, Abramson R D, Watson R, Gelfand D H. Detection of specific polymerase chain reaction product by utilizing the 5'-3' exonuclease activity of *Thermus aquaticus* DNA polymerase. Proc Natl Acad Sci USA 1991; 88:7276-7280; Gerard C J, Olsson K, Ramanathan R, Reading C, Hanania E G. Improved quantitation of minimal residual disease in multiple myeloma using real-time polymerase chain reaction and plasmid-DNA complementarity determining region III standards. Cancer Res 1998; 58:3957-3964; Gelmini S, Orlando C, Sestini R, et al. Quantitative polymerase chain reaction-based homogeneous assay with fluorogenic probes to measure c-erB-2 oncogene amplification. Clin Chem 1997; 43:752-758; deKok J B, Hendriks J C M, van Solinge W W, Willems H L, Mensink E J, Swinkels D W. Use of real-time quantitative PCR to compare DNA isolation methods. Clin Chem 1998; 44:2201-2204; Lockey C, Otto E, Long Z. Real-time fluorescence detection of a single DNA molecule. Biotechniques 1998; 24:744-746; Marcucci G, Livak K J, Bi W, Strout M P, Bloomfield C D, Caligiuri M A. Detection of minimal residual disease in patients with AML1/ETO-associated acute myeloid leukemia using a novel quantitative reverse transcription polymerase chain reaction assay. Leukemia 1998; 12:1482-1489; Suryanarayana K, Wiltrout T A, Vasquez G M, Hirsch V M, Lifson J D. Plasma SIV RNA viral load determination by real-time quantification of product generation in reverse transcriptase-polymerase chain reaction. AIDS Res Hum Retroviruses 1998; 14:183-189; Morris T, Robertson B, Gallagher M. Rapid reverse transcription-PCR detection of hepatitis C virus RNA in serum by using the TaqMan fluorogenic detection system. J Clin Microbiol 1996; 34:2933-2936; Swan D C, Tucker R A, Holloway B P, Icenogle J P. A sensitive, type-specific, fluorogenic probe assay for detection of human papillomavirus DNA. J Clin Microbiol 1997; 35:886-891; McGoldrick A, Lowings J P, Ibata G, Sands J J, Belak S, Paton D J. A novel approach to the detection of classical swine fever virus by RT-PCR with a fluorogenic probe (TaqMan). J Virol Methods 1998; 72:125-135; Abe, A., K. Inoue, T. Tanaka, J. Kato, N. Kajiyama, R. Kawaguchi, S. Tanaka, M. Yoshiba, and M. Kohara 1999. Quantitation of hepatitis B virus genomic DNA by real-time detection PCR. J Clin Microbiol. 37:2899-2903; Aberham, C., C. Pendl, P. Gross, G. Zerlauth, and M. Gessner 2001. A quantitative, internally controlled real-time PCR Assay for the detection of parvovirus B19 DNA. J Virol Methods. 92:183-191; Bisset, L. R., S. Bosbach, Z. Tomasik, H. Lutz, J. Schupbach, and J. Boni 2001. Quantification of in vitro retroviral replication using a one-tube real-time RT-PCR system incorporating direct RNA preparation. J Virol Methods. 91:149-155; Cane, P. A., P. Cook, D. Ratcliffe, D. Mutimer, and D. Pillay 1999. Use of real-time PCR and fluorimetry to detect lamivudine resistance-associated mutations in hepatitis B virus. Antimicrob Agents Chemother. 43:1600-1608; Cubic, H. A., A. L. Seagar, E. McGoogan, J. Whitehead, A. Brass, M. L. Arends, and M. W. Whitley 2001. Rapid real time PCR to distinguish between high risk human papillomavirus types 16 and 18. Mol. Pathol. 54:24-29; Desire, N., A. Dehee, V. Schneider, C. Jacomet, C. Goujon, P. M. Girard, W. Rozenbaum, and J. C. Nicolas 2001. Quantification of human immunodeficiency virus type 1 proviral load by a TaqMan real-time PCR assay. J Clin Microbiol. 39:1303-1310; Gault, E., Y. Michel, A. Dehee, C. Belabani, J. C. Nicolas, and A. Garbarg-Chenon 2001. Quantification of human cytomegalovirus DNA by real-time PCR. J Clin Microbiol. 39:772-775; Gniber, F., F. G. Falkner, F. Dorner, and T. Harmnerle 2001. Quantitation of viral DNA by real-time PCR applying duplex amplification, internal standardization, and two-color fluorescence detection. Appl Environ Microbiol. 67:2837-2839; Jabs, W. J., H. Hennig, M. Kittel, K. Pethig, F. Smets, P. Bucsky, H. Kirchner, and H. J. Wagner 2001. Normalized quantification by real-time PCR of Epstein-Barr virus load in patients at risk for posttransplant lymphoproliferative disorders. J Clin Microbiol. 39:564-569; Josefsson, A., K. Livak, and U. Gyllensten 1999. Detection and quantitation of human papillomavirus by using the fluorescent 5' exonuclease assay. J Clin Microbiol. 37:490496; Kato, T., M. Mizokami, M. Mukaide, E. Orito, T. Ohno, T. Nakano, Y. Tanaka, H. Kato, F. Sugauchi, R. Ueda, N. Hirashima, K. Shimamatsu, M. Kage, and M. Kojiro 2000. Development of a TT virus DNA quantification system using real-time detection PCR. J Clin Microbiol. 38:94-98; Kearns, A. M., M. Guiver, V. James, and J. King 2001. Development and evaluation of a real-time quantitative PCR for the detection of human cytomegalovirus. J Virol Methods. 95:121-131; Kessler, H. H., G. Muhlbauer, B. Rinner, E. Stelzl, A. Berger, H. W. Dorr, B. Santner, E. Marth, and H. Rabenau 2000. Detection of Herpes simplex virus DNA by real-time PCR. J Clin Microbiol. 38:2638-2642; Kimura, H., M. Morita, Y. Yabuta, K. Kuzushima, K. Kato, S. Kojima, T. Matsuyama, and T. Morishima 1999. Quantitative analysis of Epstein-Barr virus load by using a real-time PCR assay. J Clin Microbiol. 37:132-136; Komurian-Pradel, F., G. Paranhos-Baccala, M. Sodoyer, P. Chevallier, B. Mandrand, V. Lotteau, and P. Andre 2001. Quantitation of HCV RNA using real-time PCR and fluorimetry. J Virol Methods. 95:111-119; Kuimelis, R. G., K. J. Livak, B. Mullah, and A. Andrus 1997. Structural analogues of TaqMan probes for real-time quantitative PCR. Nucleic Acids Symp Ser. 37:255-256; Lallemand, F., N. Desire, W. Rozenbaum, J. C. Nicolas, and V. Marechal 2000. Quantitative analysis of human herpesvirus 8 viral load using a real-time PCR assay. J Clin Microbiol. 38:1404-1408; Lewin, S. R., M. Vesanen, L. Kostrikis, A. Hurley, M. Duran, L. Zhang, D. D. Ho, and M. Markowitz 1999. Use of real-time PCR and molecular beacons to detect virus replication in human immunodeficiency virus type 1-infected individuals on prolonged effective antiretroviral therapy. J. Virol. 73:6099-6103. Locatelli, G., F. Santoro, F. Veglia, A. Gobbi, P. Lusso, and M. S. Malnati 2000. Real-time quantitative PCR for human herpesvirus 6 DNA. J Clin Microbiol. 37:4042-4048; Machida, U., M. Kami, T. Fukui, Y. Kazuyama, M. Kinoshita, Y. Tanaka, Y. Kanda, S. Ogawa, H. Honda, S. Chiba, K. Mitani, Y. Muto, K. Osumi, S. Kimura, and H. Hirai 2000. Real-time automated PCR for early diagnosis and monitoring of *cytomegalovirus* infection after bone marrow transplantation. J Clin Microbiol. 38:2536-2542; Martell, M., J. Gomez, J. I. Esteban, S. Sauleda, J. Quer, B. Cabot, R. Esteban, and J. Guardia 1999. High-throughput real-time reverse transcription-PCR quantitation of hepatitis C virus RNA. J Clin Microbiol. 37:327-332; Najioullah, F., D. Thouvenot, and B. Lina 2001. Development of a real-time PCR procedure including an internal control for the measurement of HCMV viral load. J Virol Methods. 92:55-64; Nicoll, S., A. Brass, and H. A. Cubie 2001. Detection of herpes viruses in clinical samples using real-time PCR. J Virol Methods. 96:25-31; Niesters, H. G., J. van Esser, E. Fries, K. C. Wolthers, J. Comelissen, and A. D. Osterhaus 2000. Development of a real-time quantitative assay for detection of epstein-barr virus. J Clin Microbiol. 38:712-715; Nitsche, A., N. Steuer, C. A. Schmidt, O. Landt, H. Ellerbrok, G. Pauli, and W. Siegert 2000. Detection of human cytomegalovirus DNA by real-time quantitative PCR. J Clin Microbiol. 38:2734-2737; Ohyashiki, J. H., A. Suzuki, K. Aritaki, A. Nagate, N. Shoji, K. Ohyashiki, T. Ojima, K. Abe, and K. Yamamoto 2000. Use of real-time PCR to monitor human herpesvirus 6 reactivation after allogeneic bone marrow transplantation. Int J Mol. Med. 6:427-432; Pevenstein, S. R., R. K. Williams, D. McChesney, E. K. Mont, J. E. Smialek, and S. E. Straus 1999. Quantitation of latent varicella-zoster virus and herpes simplex virus genomes in human trigeminal ganglia. J. Virol. 73:10514-10548; Ratge, D., B. Scheiblhuber, M. Nitsche, and C. Knabbe 2000. High-speed detection of blood-borne hepatitis C virus RNA by single-tube real-time fluorescence reverse transcription-PCR with the LightCycler. Clin Chem. 46:1987-1989; Saha, B. K., B. Tian, and R. P. Bucy 2001. Quantitation of HIV-1 by real-time PCR with a unique fluorogenic probe J Virol Methods. 93:33-42; Sauleda, S., H. J. Reesink, J. I. Esteban, G. Hess, R. Esteban, and J. Guardia 1999. Profiles of GBV-C/hepatitis G virus markers in patients coinfected with hepatitis C virus. J Med Virol. 59:45-51; Schutten, M., B. van den Hoogen, M. E. van der Ende, R. A. Gruters, A. D. Osterhaus, and H. G. Niesters 2000. Development of a real-time quantitative RT-PCR for the detection of HIV-2 RNA in plasma. J Virol Methods. 88:81-87; Takeuchi, T., A. Katsume, T. Tanaka, A. Abe, K. Inoue, K. Tsukiyama-Kohara, R. Kawaguchi, S. Tanaka, and M. Kohara 1999. Real-time detection system for quantification of hepatitis C virus genome. Gastroenterology. 116:636-642; Tanaka, N., H. Kimura, K. Iida, Y. Saito, I. Tsuge, A. Yoshimi, T. Matsuyama, and T. Morishima 2000. Quantitative analysis of cytomegalovirus load using a real-time PCR assay. J Med Virol. 60:455-462; Tucker, R. A., E. R. Unger, B. P. Holloway, and D. C. Swan 2001. Real-time PCR-based fluorescent assay for quantitation of human papillomavirus types 6, 11, 16, and 18. Mol Diagn. 6:39-47; Tyagi, S., and F. R. Kramer 1996. Molecular beacons: probes that fluoresce upon hybridization. Nat. Biotechnol. 14:303-308; van Elden, L. J., M. Nijhuis, P. Schipper, R. Schuurman, and A. M. van Loon 2001. Simultaneous detection of influenza viruses A and B using real-time quantitative PCR. J Clin Microbiol. 39:196-200; Vet, J. A., A. R. Majithia, S. A. Marras, S. Tyagi, S. Dube, B. J. Poiesz, and F. R. Kramer 1999. Multiplex detection of four pathogenic retroviruses using molecular beacons. Proc Natl Acad Sci USA. 96:6394-6399; Wagner, H. J., W. Jabs, F. Smets, M. Wessel, L. Fischer, G. Offner, H. Kirchner, and P. Bucsky 2000. Real-time polymerase chain reaction (RQ-PCR) for the monitoring of Epstein-Barr virus (EBV) load in peripheral blood mononuclear cells. Klin Padiatr. 212:206-210; Walker, N. J. 2001. Real-time and quantitative PCR: applications to mechanism-based toxicology. J Biochem Mol. Toxicol. 15:121-127; and White, I. E., and T. B. Campbell 2000. Quantitation of cell-free and cell-associated Kaposi's sarcoma-associated herpesvirus DNA by real-time PCR. J Clin Microbiol. 38:1992-1995.

Although assays exist for the diagnosis and evaluation of viral infections, additional assays and kits are needed that provide a more sensitive or precise analysis of the condition of a diseased cell. More sensitive and precise methods are also needed to assess the activity of a compound or substance against a target virus and to assess host toxicity induced by the compound or substance.

It is therefore an object of the present invention to provide a process for the identification of active compounds for the treatment of viral infections.

It is another object of the present invention to provide a process to measure mitochondrial toxicity.

It is another object of the present invention to provide a process for the detection and analysis of viral infections.

It is a further object of the invention to provide a process for the detection and analysis of mitochondrial toxicity.

SUMMARY OF THE INVENTION

Processes and methods for the simultaneous quantification of nucleic acids in diseased cells that are based on real-time PCR are provided. The real-time-PCR protocol is an excellent tool for reliable quantification of in vitro drug screening and evaluation protocols to determine the efficacy of potential anti-viral agents. Quantification using these simulateous PCR cycle threshold (Ct) detection techniques during one-step real-time RT-PCR (Applied Biosystems, CA) eliminates the variability resulting from quantification of end-point RT-PCR products. In addition, the mitochondrial toxicity assay is an added tool to assess potential side-effects for these chemotherapeutic agents.

This real time multiplex PCR system includes the simultaneous measurements of cellular DNA (for example rDNA) or cellular RNA (for example rRNA or β-actin m-RNA), and viral RNA or DNA. In one embodiment, the simultaneous real time analysis of host and viral nucleic acid allows the calculation of a sensitivity assay that indicates the comparative condition of the host cell and the virus. In a separate aspect of the invention, multiplex PCR is used to simultaneously measure the nuclear and the mitochondrial nucleic acid of a cell to provide information on drug toxicity, or to evaluate a cell (in vivo or in vitro) that may exhibit a disease that involves mitochondrial toxicity, such as peripheral neuropathy, peripheral lipodystrophy, or a genetic disease that causes a disruption in mitochondrial DNA or RNA synthesis.

The methods and processes are economic, non-radioactive, rapid, accurate, reproducible, and amenable to large throughput. It can provide a dynamic range of quantification with linearity of over 5-7 logs. One way to express the antiviral effectiveness of a compound is to subtract the threshold RT-PCR cycle of the test compound with the average threshold RT-PCR cycle of the negative control. This value is called DeltaCt ($\Delta$Ct). A $\Delta$Ct of 3.3 equals a 1-log reduction (equals $EC_{90}$) in viral nucleic acid production. Compounds that result in a reduction of viral nucleic acid greater than 1.5, or more preferred, 2 Ct values (75% reduction of viral nucleic acid) are typically useful compounds for the inhibition of viral growth.

With the availability of both the viral $\Delta$Ct data and the host $\Delta$Ct, a specificity parameter can be introduced. This parameter is obtained by subtracting the host $\Delta$Ct value from the viral $\Delta$Ct value. This results in $\Delta\Delta$Ct values; a value above 0 means that there is more inhibitory effect on the viral nucleic acid, a $\Delta\Delta$Ct value below 0 means that the host nucleic acid is more affected. As a general rule, $\Delta\Delta$Ct values above 2 are considered as significantly different from the no-drug treatment control, and hence, exhibits useful antiviral activity. However, compounds with a $\Delta\Delta$Ct value of less than 2, but showing limited molecular cytotoxicty data (rRNA $\Delta$CT between 0 and 2) may also be desired for certain applications requiring compounds with low toxicity.

As an example, a compound might reduce the host RNA polymerase activity, but not the host DNA polymerase activity. Therefore, quantification of rDNA or β-actin DNA (or any other host DNA fragment) and comparison with DNA levels of the no-drug control is a relative measurement of the inhibitory effect of the test compound on cellular DNA polymerases. With the availability of both the HCV $\Delta$Ct data and the rDNA $\Delta$Ct, a specificity parameter can be introduced. This parameter is obtained by subtracting both $\Delta$Ct values from each other. This results in $\Delta\Delta$Ct values; a value above 0 means that there is more inhibitory effect on the viral encoded polymerase, a $\Delta\Delta$Ct value below 0 means that the host rDNA levels are more affected than the viral nucleic acid levels. As a general rule, $\Delta\Delta$Ct values above 2 are considered as significantly different from the no-drug treatment control, and hence, is an interested compound for further evaluation. However, compounds with a $\Delta\Delta$Ct value of less than 2, but with limited molecular cytotoxicty (rDNA $\Delta$CT between 0 and 2) are also possible active candidate compounds for further evaluation In a first embodiment, a process for assessing a viral disease is provided that includes contacting nucleic acid from a viral infected host cell with an amplification reaction mixture that contains at least two primers and/or probes that provide detectable signals during a polymerase chain reaction, wherein the first primer and/or probe provides a detectable signal on the occurrence on the transcription of host nucleic acid; and the second primer and/or probe provides a second detectable signal on the occurrence on the transcription of viral nucleic acid.

In a particular embodiment, the level of transcription of the viral and host nucleic acid is compared to that of a standard, including but not limited to, a known viral infected host cell, or alternatively, an internal standard can be established by comparing the extent of transcription of the host and viral nucleic acid over a number of samples from the host to monitor and measure the change in infection. In another embodiment, the data can be assessed as described above through the use of $\Delta$CT and $\Delta\Delta$Ct values.

In a preferred embodiment, the nucleic acid is a consensus or non-coding sequence, which can be either 5' or 3' to the target expressed sequence. In one embodiment, the non-coding sequence is an intron or a part thereof. Non-limiting examples are non-coding sequences from β-actin or GAPDH.

The host nucleic acid can be nuclear or cytoplasmic, and in particular, mitochondrial nucleic acid, and the viral nucleic acid can be either DNA or RNA.

This process can be used to evaluate the ability of the compound or substance to inhibit the replication of any virus, including but not limited to a virus from the Retroviridae, Flaviviridae, Orthomyxoviridae, Paramyxoviridae, Herpesviridae, Hepadnaviridae, Picornaviridae, Reoviridae, Poxyiridae, Adenoviridae, Papoviridae, Parvoviridae, Bunyaviridae, Filoviridae, Arenaviridae or Togaviridae family. In particular, the virus is HIV, hepatitis (including but not limited to A, B, C, D and G), BVDV (bovine diarrhea virus), herpes simplex, Adenovirus type 1, influenza, including influenza A (HINI), influenza A (H3N2), influenza B, influenza C and influenza D, measles, mumps, parainfluenza type 3, RSV (respiratory syncytial virus), HSV (herpes simplex virus), EBV (Epstein Barr virus), CMV (cytomegalovirus) or West Nile Virus.

In a second embodiment, a process for assessing a disease state that includes a disruption in mitochondrial DNA or RNA synthesis is provided that includes contacting nucleic acid from a host with an amplification reaction mixture that contains at least two primers and/or probes that provide detectable signals during a polymerase chain reaction, wherein
the first primer and/or probe provides a detectable signal on the occurrence on the transcription of host mitochondrial nucleic acid; and
the second primer and/or probe provides a second detectable signal on the occurrence on the transcription of host nuclear nucleic acid.

In a third embodiment, a process for identifying a compound or substance that inhibits viral replication is provided that includes (i) contacting nucleic acid from a virus infected host that has been treated with the compound with (ii) an amplification reaction mixture that contains at least two primers and/or probes that provide detectable signals during a polymerase chain reaction, wherein
the first primer and/or probe provides a detectable signal on the occurrence of the transcription of viral nucleic acid; and
the second primer and/or probe provides a second detectable signal on the occurrence of the transcription of host nucleic acid.

In a fourth embodiment, a process for assessing the mitochondrial toxicity of a compound is provided that includes contacting nucleic acid from a host that has been treated with the compound with an amplification reaction mixture that contains at least two primers and/or probes that provide detectable signals during a polymerase chain reaction, wherein
the first primer and/or probe provides a detectable signal on the occurrence on the transcription of host mitochondrial nucleic acid; and
the second primer and/or probe provides a second detectable signal on the occurrence on the transcription of host nuclear nucleic acid.

In a fifth embodiment, a process for assessing the tendency of a compound to induce peripheral neuropathy or peripheral lipodystrophy is provided that includes contacting nucleic acid from a host cell that has been treated with the compound with an amplification reaction mixture that contains at least two primers and/or probes that provide detectable signals during a polymerase chain reaction, wherein
the first primer and/or probe provides a detectable signal on the occurrence on the transcription of host mitochondrial nucleic acid; and
the second primer and/or probe provides a second detectable signal on the occurrence on the transcription of host nuclear nucleic acid.

These processes and methods optimally utilize the conserved regions in the genome of the virus and host to design unique combinations of a PCR primer/probe-sets. In one embodiment, this probe contains a detectable signal, so that upon exonucleic degradation, the signal, indicating target nucleic acid, can be detected in real-time. This technique has been found to be sensitive and accurate; in addition, quantification using PCR cycle threshold (Ct) detection during one-step real-time RT-PCR (Applied Biosystems, CA) has eliminated the variability resulting from quantification of end-point RT-PCR products.

In a particular embodiment of the present invention, process of simultaneous real-time PCR includes the following steps:
a) contacting at least a portion of a target nucleic acid sequence in a sample with
   i) a suitable amplification reaction mixture; and
   ii) two or more independently labeled oligonucleotides or probes that hybridizes to the target nucleic acid sequence, such that the when the target nucleic acid sequence is amplified, each independently labeled probe releases an unique detectable signal;
   iii) wherein at least one independently labeled oligonucleotide or probe that hydrbiridizes to a target viral nucleic acid sequence; and
   iv) at least one independently labeled oligonucleotide or probe that hydrbiridizes to a target host nucleic acid sequence;
b) carrying out an amplification procedure on the amplification mixture; and
c) detecting in real time the release of the unique signals.

The presence of the amplicon, of course, indicates that the target nucleic acid is present in the sample; the target RNA or DNA in the sample can be quantitated based on signal intensity.

The current invention can also be applied to a new method for sensitive and accurate determination of mitochondrial toxicity of candidate chemotherapeutic compounds using real-time-PCR by determining the ratio of nuclear (or endogenous control) DNA or RNA to mitochondrial DNA or RNA. In a preferred embodiment, this toxicity screening assay is used to determine toxicity of potential anti-viral agents, and in particular anti-HIV, especially anti-HIV-1, and anti-hepatitis viruses, especially HBV and HCV.

In order to quantify the total amount of mitochondrial DNA or RNA, amplification of an endogenous control needs to be performed to standardize the amount of such mitochondrial DNA or RNA. This endogenous control is an RNA or DNA that is present in each experimental sample and is representative of the total amount of nuclear DNA or RNA. By using this endogenous control as an active reference, quantities of mitochondrial DNA or RNA can be normalized for differences in the amount of total DNA or RNA added to each reaction. Some non-limiting examples of endogenous controls are any human gene, but especially β-actin, glyceraldehyde-3-phosphate dehydrogenase or ribosomal RNA.

This method includes the following steps:
a) contacting at least a portion of a nuclear nucleic acid sequence in a sample with
   i) an amplification reaction mixture; and
   i) two or more independently labeled oligonucleotides or probes that hybridizes to the target nucleic acid sequence, such that the when the target nucleic acid sequence is amplified, each independently labeled probe releases an unique detectable signal;
   ii) wherein at least one independently labeled oligonucleotide or probe hybridizes to a target nuclear nucleic acid sequence; and
   iii) at least one independently labeled oligonucleotide or probe that hybridizes to a target mitochondrial nucleic acid sequence;
b) carrying out an amplification procedure on the amplification mixture;
c) detecting in real time the release of the signal.

The quantity of the nuclear amplicon can be compared to the quantity of mitochondrial amplicon based on differences in signal intensity, thereby indicating the level of mitochondrial toxicity.

BRIEF DESCRIPTION OF THE FIGURES

FIG. 10 contains two bar graphs showing the changes in nucleic acid levels in Huh7 cells in terms of the amount of mitochondrial RNA and, in the other, the changes in mitochondrial DNA, after a seven day incubation period with various drugs.

DETAILED DESCRIPTION OF THE INVENTION

Figure 1A:
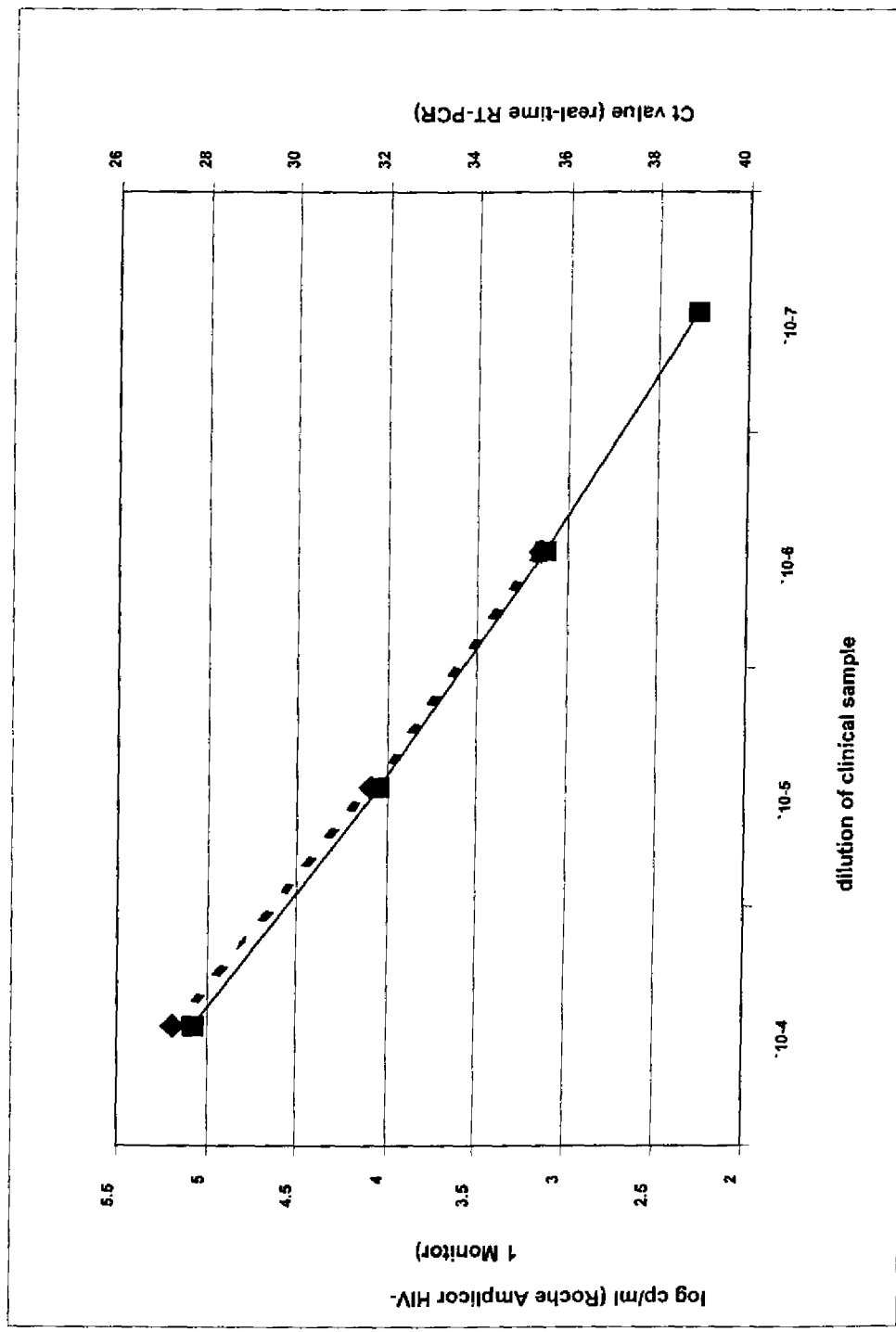
FIG. 1 is an illustration of a calibration of standard curve for HIV-1 (1a), HCV (1b), BVDV (1c), mitochondrial DNA (1d) and molecular toxicology (1e) RT-PCR. The attenuated clinical samples were diluted in DMEM-F12/10% FBS. The Ct value indicates the threshold cycle where the one-step RT-PCR detection of the target becomes positive. The Log cp/mL value is the logarithm of the amount of target copies per mL sample. The ◆ line indicates the Roche Amplicor HIV-1 Monitor, while the ■ line indicates real-time HIV-1 RT-PCR.

Processes and methods for the simultaneous quantification of nucleic acids in diseased cells that are based on real-time PCR are provided. The real-time-PCR protocol is an excellent tool for reliable quantification of in vitro drug screening and evaluation protocols to determine the efficacy of potential anti-viral agents. Quantification using these simulateous PCR cycle threshold (Ct) detection techniques during one-step real-time RT-PCR (Applied Biosysterns, CA) eliminated the variability resulting from quantification of end-point RT-PCR products. In addition, the mitochondrial toxicity assay is an added tool to assess potential side-effects for these chemotherapeutic agents.

This real time multiplex PCR system includes the simultaneous measurements of cellular DNA (for example rDNA) or cellular RNA (for example rRNA or β-actin m-RNA), and viral RNA or DNA. In one embodiment, the simultaneous real time analysis of host and viral nucleic acid allows the calculation of a sensitivity assay that indicates the comparative condition of the host cell and the virus. In a separate aspect of the invention, multiplex PCR is used to simultaneously measure the nuclear and the mitochondrial nucleic acid of a cell to provide information on drug toxicity, or to evaluate a cell (in vivo or in vitro) that may exhibit a disease that involves mitochondrial toxicity, such as peripheral neuropathy, peripheral lipodystrophy, or a genetic disease that causes a disruption in mitochondrial DNA or RNA synthesis.

The methods and processes are economic, non-radioactive, rapid, accurate, reproducible, and amenable to large throughput. It can provide a dynamic range of quantification with linearity of over 5-7 logs. One way to express the antiviral effectiveness of a compound is to subtract the threshold RT-PCR cycle of the test compound with the average threshold RT-PCR cycle of the negative control. This value is called DeltaCt (ΔCt). A ΔCt of 3.3 equals a 1-log reduction (equals $EC_{90}$) in viral nucleic acid production. Compounds that result in a reduction of viral nucleic acid greater than 1.5, or more preferred, 2 Ct values (75% reduction of viral nucleic acid) are typically useful compounds for the inhibition of viral growth.

With the availability of both the viral ΔCt data and the host ΔCt, a specificity parameter can be introduced. This parameter is obtained by subtracting the host ΔCt value from the viral ΔCt value. This results in ΔΔCt values; a value above 0 means that there is more inhibitory effect on the viral nucleic acid, a ΔΔCt value below 0 means that the host nucleic acid is more affected. As a general rule, ΔΔCt values above 2 are considered as significantly different from the no-drug treatment control, and hence, exhibits useful antiviral activity. However, compounds with a ΔΔCt value of less than 2, but showing limited molecular cytotoxicty data (rRNA ΔCT between 0 and 2) may also be desired for certain applications requiring compounds with low toxicity.

As an example, a compound might reduce the host RNA polymerase activity, but not the host DNA polymerase activity. Therefore, quantification of rDNA or β-actin DNA (or any other host DNA fragment) and comparison with DNA levels of the no-drug control is a relative measurement of the inhibitory effect of the test compound on cellular DNA polymerases. With the availability of both the HCV ΔCt data and the rDNA ΔCt, a specificity parameter can be introduced. This parameter is obtained by subtracting both ΔCt values from each other. This results in ΔΔCt values; a value above 0 means that there is more inhibitory effect on the viral encoded polymerase, a ΔΔCt value below 0 means that the host rDNA levels are more affected than the viral nucleic acid levels. As a general rule, ΔΔCt values above 2 are considered as significantly different from the no-drug treatment control, and hence, is an interested compound for further evaluation. However, compounds with a ΔΔCt value of less than 2, but with limited molecular cytotoxicty (rDNA ΔCT between 0 and 2) are also possible active candidate compounds for further evaluation In a first embodiment, a process for assessing a viral disease is provided that includes contacting nucleic acid from a viral infected host cell with an amplification reaction mixture that contains at least two primers and/or probes that provide detectable signals during a polymerase chain reaction, wherein the first primer and/or probe provides a detectable signal on the occurrence on the transcription of host nucleic acid; and the second primer and/or probe provides a second detectable signal on the occurrence on the transcription of viral nucleic acid.

In a particular embodiment, the level of transcription of the viral and host nucleic acid is compared to that of a standard, including but not limited to, a known viral infected host cell, or alternatively, an internal standard can be established by comparing the extent of transcription of the host and viral nucleic acid over a number of samples from the host to monitor and measure the change in infection. In another embodiment, the data can be assessed as described above through the use of ΔCT and ΔΔCt values.

In a preferred embodiment, the nucleic acid is a consensus or non-coding sequence, which can be either 5' or 3' to the target expressed sequence. In one embodiment, the non-coding sequence is an intron or a part thereof. Non-limiting examples are non-coding sequences from β-actin or GAPDH.

The host nucleic acid can be nuclear or cytoplasmic, and in particular, mitochondrial nucleic acid, and the viral nucleic acid can be either DNA or RNA.

This process can be used to evaluate the ability of the compound or substance to inhibit the replication of any virus, including but not limited to a virus from the Retroviridae, Flaviviridae, Orthomyxoviridae, Paramyxoviridae, Herpesviridae, Hepadnaviridae, Picornaviridae, Reoviridae, Poxyiridae, Adenoviridae, Papoviridae, Parvoviridae, Bunyaviridae, Filoviridae, Arenaviridae or Togaviridae family. In particular, the virus is HIV, hepatitis (including but not limited to A, B, C, D and G), BVDV (bovine diarrhea virus), herpes simplex, Adenovirus type 1, influenza, including influenza A (HINI), influenza A (H3N2), influenza B, influenza C and influenza D, measles, mumps, parainfluenza type 3, RSV (respiratory syncytial virus), HSV (herpes simplex virus), EBV (Epstein Barr virus), CMV (cytomegalovirus) or West Nile Virus.

In a second embodiment, a process for assessing a disease state that includes a disruption in mitochondrial DNA or RNA synthesis is provided that includes contacting nucleic acid from a host with an amplification reaction mixture that contains at least two primers and/or probes that provide detectable signals during a polymerase chain reaction, wherein the first primer and/or probe provides a detectable signal on the occurrence on the transcription of host mitochondrial nucleic acid; and the second primer and/or probe provides a second detectable signal on the occurrence on the transcription of host nuclear nucleic acid.

In a third embodiment, a process for identifying a compound or substance that inhibits viral replication is provided that includes (i) contacting nucleic acid from a virus infected host that has been treated with the compound with (ii) an amplification reaction mixture that contains at least two primers and/or probes that provide detectable signals during a polymerase chain reaction, wherein the first primer and/or probe provides a detectable signal on the occurrence of the transcription of viral nucleic acid; and the second primer and/or probe provides a second detectable signal on the occurrence of the transcription of host nucleic acid.

In a fourth embodiment, a process for assessing the mitochondrial toxicity of a compound is provided that includes contacting nucleic acid from a host that has been treated with the compound with an amplification reaction mixture that contains at least two primers and/or probes that provide detectable signals during a polymerase chain reaction, wherein the first primer and/or probe provides a detectable signal on the occurrence on the transcription of host mitochondrial nucleic acid; and the second primer and/or probe provides a second detectable signal on the occurrence on the transcription of host nuclear nucleic acid.

In a fifth embodiment, a process for assessing the tendency of a compound to induce peripheral neuropathy or peripheral lipodystrophy is provided that includes contacting nucleic acid from a host cell that has been treated with the compound with an amplification reaction mixture that contains at least two primers and/or probes that provide detectable signals during a polymerase chain reaction, wherein the first primer and/or probe provides a detectable signal on the occurrence on the transcription of host mitochondrial nucleic acid; and the second primer and/or probe provides a second detectable signal on the occurrence on the transcription of host nuclear nucleic acid.

These processes and methods optimally utilize the conserved regions in the genome of the virus and host to design unique combinations of a PCR primer/probe-sets. In one embodiment, this probe contains a detectable signal, so that upon exonucleic degradation, the signal, indicating target nucleic acid, can be detected in real-time. This technique has been found to be sensitive and accurate; in addition, quantification using PCR cycle threshold (Ct) detection during one-step real-time RT-PCR (Applied Biosystems, CA) has eliminated the variability resulting from quantification of end-point RT-PCR products.

In a particular embodiment of the present invention, a method of simultaneous real-time PCR includes the following steps:

a) contacting at least a portion of a target nucleic acid sequence in a sample comprising:
  i) a suitable amplification reaction mixture; and
  ii) two or more independently labeled oligonucleotides or probes that hybridizes to the target nucleic acid sequence, such that the when the target nucleic acid sequence is amplified, each independently labeled probe releases an unique detectable signal;
  iii) wherein at least one independently labeled oligonucleotide or probe that hydrbiridizes to a target viral nucleic acid sequence; and
  iv) at least one independently labeled oligonucleotide or probe that hydrbiridizes to a target host nucleic acid sequence;
b) carrying out an amplification procedure on the amplification mixture; and
c) detecting in real time the release of the unique signals.

The presence of the amplicon, of course, indicates that the target nucleic acid is present in the sample; the target RNA or DNA in the sample can be quantitated based on signal intensity.

The current invention can also be applied to a new method for sensitive and accurate determination of mitochondrial toxicity of candidate chemotherapeutic compounds using real-time-PCR by determining the ratio of nuclear (or endogenous control) DNA or RNA to mitochondrial DNA or RNA. In a preferred embodiment, this toxicity screening assay is used to determine toxicity of potential anti-viral agents, and in particular anti-HIV, especially anti-HIV-1, and anti-hepatitis viruses, especially HBV and HCV.

This method includes the following steps:
a) contacting at least a portion of a nuclear nucleic acid sequence in a sample comprising:
   i) an amplification reaction mixture; and
   i) two or more independently labeled oligonucleotides or probes that hybridizes to the target nucleic acid sequence, such that the when the target nucleic acid sequence is amplified, each independently labeled probe releases an unique detectable signal;
   ii) wherein at least one independently labeled oligonucleotide or probe hybridizes to a target nuclear nucleic acid sequence; and
   iii) at least one independently labeled oligonucleotide or probe that hybridizes to a target mitochondrial nucleic acid sequence;
d) carrying out an amplification procedure on the amplification mixture;
e) detecting in real time the release of the signal.

The quantity of the nuclear amplicon can be compared to the quantity of mitochondrial amplicon based on differences in signal intensity, thereby indicating the level of mitochondrial toxicity.

I. Screening

These processes and methods can be used to evaluate the ability of the compound or substance to inhibit the replication of any virus, including but not limited to a virus from the Retroviridae, Flaviviridae, Orthomyxoviridae, Paramyxoviridae, Herpesviridae, Hepadnaviridae, Picornaviridae, Reoviridae, Poxyiridae, Adenoviridae, Papoviridae, Parvoviridae, Bunyaviridae, Filoviridae, Arenaviridae or Togaviridae family. In particular, the virus is HIV, hepatitis (including but not limited to A, B, C, D and G), BVDV (bovine diarrhea virus), herpes simplex, Adenovirus type 1, influenza, including influenza A (HINI), influenza A (H3N2), influenza B, influenza C and influenza D, measles, mumps, parainfluenza type 3, RSV (respiratory syncytial virus), HSV (herpes simplex virus), EBV (Epstein Barr virus), CMV (cytomegalovirus) or West Nile Virus.

In particular, quantitative real-time PCR antiviral screening can be combined with calibration for a host RNA targets (in RT-PCR) in the following non-limiting examples:
a) anti-HCV compound screening can be combined with rRNA calibration, mRNA calibration, and in particular -actin mRNA calibration, mitochondrial RNA calibration and/or any other nuclear or mitochondrial nucleic acid calibration;
b) anti-HIV compound screening can be combined with rRNA calibration, mRNA calibration, and in particular -actin mRNA calibration, mitochondrial RNA calibration and/or any other nuclear or mitochondrial nucleic acid calibration;
c) anti-HBV compound screening can be combined with rRNA calibration, mRNA calibration, and in particular -actin mRNA calibration, mitochondrial RNA calibration and/or any other nuclear or mitochondrial nucleic acid calibration;
d) anti-RSV compound screening can be combined with rRNA calibration, mRNA calibration, and in particular -actin mRNA calibration, mitochondrial RNA calibration and/or any other nuclear or mitochondrial nucleic acid calibration;
e) anti-BVDV compound screening can be combined with rRNA calibration, mRNA calibration, and in particular -actin mRNA calibration, mitochondrial RNA calibration and/or any other nuclear or mitochondrial nucleic acid calibration;
f) anti-lentivirus compound screening can be combined with rRNA calibration, mRNA calibration, and in particular -actin mRNA calibration, mitochondrial RNA calibration and/or any other nuclear or mitochondrial nucleic acid calibration;
g) anti-flaviviridae (Flavivirus, Hepacivirus, Pestivirus) compound screening can be combined with rRNA calibration, mRNA calibration, and in particular -actin mRNA calibration, mitochondrial RNA calibration and/or any other nuclear or mitochondrial nucleic acid calibration;
h) anti-hepadnavirus compound screening can be combined with rRNA calibration, mRNA calibration, and in particular -actin mRNA calibration, mitochondrial RNA calibration and/or any other nuclear or mitochondrial nucleic acid calibration;
i) anti-picornavirus compound screening can be combined with rRNA calibration, mRNA calibration, and in particular -actin mRNA calibration, mitochondrial RNA calibration and/or any other nuclear or mitochondrial nucleic acid calibration;
j) anti-herpetoviridae (HSV, HCMV, EBV) compound screening can be combined with rRNA calibration, mRNA calibration, and in particular -actin mRNA calibration, mitochondrial RNA calibration and/or any other nuclear or mitochondrial nucleic acid calibration.

Quantitative real-time PCR antiviral screening can be combined with calibration for a host DNA target (in PCR) in the following non-limiting examples:
a) anti-HCV compound screening can be combined with rDNA calibration, DNA calibration, and in particular -actin DNA calibration, mitochondrial DNA calibration and/or any other nuclear or mitochondrial nucleic acid calibration;
b) anti-HIV compound screening can be combined with rDNA calibration, DNA calibration, and in particular -actin DNA calibration, mitochondrial DNA calibration and/or any other nuclear or mitochondrial nucleic acid calibration;
c) anti-HBV compound screening can be combined with rDNA calibration, DNA calibration, and in particular -actin DNA calibration, mitochondrial DNA calibration and/or any other nuclear or mitochondrial nucleic acid calibration;
d) anti-RSV compound screening can be combined with rDNA calibration, DNA calibration, and in particular -actin DNA calibration, mitochondrial DNA calibration and/or any other nuclear or mitochondrial nucleic acid calibration;
e) anti-BVDV compound screening can be combined with rDNA calibration, DNA calibration, and in particular -actin DNA calibration, mitochondrial DNA calibration and/or any other nuclear or mitochondrial nucleic acid calibration;
f) anti-lentivirus compound screening can be combined with rDNA calibration, DNA calibration, and in particular -actin DNA calibration, mitochondrial DNA calibration and/or any other nuclear or mitochondrial nucleic acid calibration;

g) anti-flaviviridae (Flavivirus, Hepacivirus, Pestivirus) compound screening can be combined with rDNA calibration, DNA calibration, and in particular -actin DNA calibration, mitochondrial DNA calibration and/or any other nuclear or mitochondrial nucleic acid calibration;

h) anti-hepadnavirus compound screening can be combined with rDNA calibration, DNA calibration, and in particular -actin DNA calibration, mitochondrial DNA calibration and/or any other nuclear or mitochondrial nucleic acid calibration;

i) anti-picornavirus compound screening can be combined with rDNA calibration, DNA calibration, and in particular -actin DNA calibration, mitochondrial DNA calibration and/or any other nuclear or mitochondrial nucleic acid calibration;

j) anti-herpetoviridae (HSV, HCMV, EBV) compound screening can be combined with rDNA calibration, DNA calibration, and in particular -actin DNA calibration, mitochondrial DNA calibration and/or any other nuclear or mitochondrial nucleic acid calibration.

The current invention also provides a new process and method for sensitive and accurate determination of mitochondrial toxicity of chemotherapeutic or other pharmaceutical agents by determining the ratio of mitochondrial DNA or RNA to nuclear DNA or RNA. The rationale behind this methodology is driven by the fact that DNA polymerase γ inhibition eventual leads to lower amounts of mitochondrial DNA or RNA, while the amounts of nuclear DNA or RNA (for which replication is dependent on DNA polymerase α and/or β) remains constant.

In order to quantify the total amount of mitochondrial DNA or RNA, amplification of an endogenous control needs to be performed to standardize the amount of such mitochondrial DNA or RNA. This endogenous control is an RNA or DNA that is present in each experimental sample and is representative of the total amount of nuclear DNA or RNA. By using this endogenous control as an active reference, quantities of mitochondrial DNA or RNA can be normalized for differences in the amount of total DNA or RNA added to each reaction. Endogenous controls can be any human gene, but often β-actin, glyceraldehyde-3-phosphate dehydrogenase, or ribosomal RNA have been used. An effective process to quantify the total amount of endogenous control in a reaction by real-time PCR is provided II. Definitions As used herein, "sample" or "clinical sample" relates to any sample obtained from a host for use in carrying out the procedures of the present invention. In one aspect, the host is suffering from a disease or syndrome that is at least partially caused by a virus. The host may also be an asymptomatic considered to be at risk of viral infection. The sample may be a cellular sample such as a tissue sample, for example of lung tissue obtained as a biopsy or post-mortem, a fluid sample, such as blood, saliva, sputum, urine, cerebrospinal fluid, or a swabbed sample obtained by swabbing a mucus membrane surface such as nasal surface, a pharyngeal surface, a buccal surface, and the like, or it may be obtained from an excretion such as feces, or it may be obtained from other bodily tissues or body fluids commonly used in diagnostic testing.

The term "purified" in reference to RNA or DNA, as used herein, relates to released RNA or DNA from latent or inaccessible form in a virion or a cell and allowing the RNA or DNA to become freely available. In such a state, it is suitable for effective amplification by use of the polymerase chain reaction. Releasing RNA or DNA may include steps that achieve the disruption of virions containing viral RNA or DNA, as well as disruption of cells that may harbor such virions. Purification of RNA or DNA is generally carried out under conditions that rigorously and effectively exclude or inhibit any nuclease activity that may be present. Additionally, purification may include steps that achieve at least a partial separation of the RNA or DNA dissolved in an aqueous medium from other cellular or viral components, wherein such components may be either particulate or dissolved.

As used herein, "reverse transcription" or "RT" relates to a procedure catalyzed by an enzyme, reverse transcriptase, that synthesizes a cDNA from a single stranded RNA molecule, with the use of oligonucleotide primers having free 3'-hydroxyl groups. As used herein, the term "polymerase chain reaction" or "PCR" relates to a procedure whereby a limited segment of a nucleic acid molecule, which frequently is a desired or targeted segment, is amplified repetitively to produce a large amount of DNA molecules which consist only of that segment. The procedure depends on repetition of a large number of priming and transcription cycles. In each cycle, two oligonucleotide primers bind to the segment, and define the limits of the segment. A primer-dependant DNA polymerase then transcribes, or replicates, the strands to which the primers have bound. Thus, in each cycle, the number of DNA duplexes is doubled.

The term "primer" or "oligonucleotide primer," as used herein, relates to an oligonucleotide having a specific or desired nucleotide sequence that is complementary to a particular sequence on one of the strands of a DNA duplex. When the primer is caused to hybridize to the specific sequence in a DNA duplex to which it is complimentary, it may serve as the priming position, or the initiation position, for the action of a primer-dependent DNA polymerase activity. The primer, once hybridized, acts to define the 5'-end of the operation of the transcription activity of the polymerase on the duplex. Commonly in PCR, a specific pair of primers is employed, wherein one of the primers hybridizes to one of the strands and the second primer hybridizes to the complementary strand. The primers hybridize in such an orientation that transcription, which proceeds in the direction from 5' to 3', is in the direction leading from each primer toward the site of hybridization of the other primer. After several rounds of hybridization and transcription the amplified DNA produced is a segment having a defined length whose ends are defined by the sites to which the primers hybridize.

The term "probe" or "labeled oligonucleotide," as used herein, relates to an oligonucleotide having a specific or desired nucleotide sequence that is complementary to a particular sequence on one of the strands of a DNA duplex, as well as a detectable signal, such as a fluorescent dye. When the primer is caused to hybridize to the specific sequence in a DNA duplex to which it is complimentary, the signal is inactive, for example due to a covalently linked quenching dye. However, upon amplification and subsequent analysis, the signal is activated by exonucleic degradation and thus can be detected in real time. In particular, the probe can contain a fluorescent dye and a quenching dye, such that at the time of hybridization, the fluorescent dye in quenched by the quenching dye. After amplification and exonucleic degradation, the fluorescent dye is released from the quenching dye and a fluorescent signal can be detected in real time.

The term "amplification reaction mixture," as used herein refers to any reaction substance, or combination of substances that promotes the amplification of a target nucleic acid sequence, including enzymes such as polymerase, or polymerases with exonuclease activity, substrates such as nucleic acids and oligonucleotide primers, as defined herein.

As used herein, the term "specific to" or "specific for" a target sequence, in relation to a nucleic acid sequence such as an oligonucleotide sequence, relate to a nucleotide sequence that hybridizes, under conditions used in given experimental circumstances, to the target but does not hybridize under those circumstances to sequences that are not target sequences. Nucleotide sequences that are specific for a particular target, such as the HIV target sequences that are included in the subject matter of the present invention, are those that include bases all of which are complementary to the corresponding base on the target.

Further, the term "specificity," as used herein, of a nucleic acid sequence for a target sequence also encompasses nucleic acids and oligonucleotides having a small number of nucleotides that may not be complementary to the corresponding nucleotides of the target sequence. Such sequences are still "specific" for the target sequence, as long as the extent of the deviation from complementarity remains functionally of no consequence. In particular, such a sequence is "specific" for the target sequence as long as it hybridized effectively to the target sequence but does not hybridize to any sequence that is not a target sequence in the sample, under the conditions used in given experimental circumstances.

The term "amplicon" as used herein refers to a double stranded nucleic acid segment having a defined size and sequence that results from an amplification procedure, such as a PCR procedure. The size of the amplicon is limited by the sites on the two strands of a nucleic acid duplex to which the primers bind. That segment of the product nucleic acid becomes the prevalent product of the amplification procedure after a small number of cycles of amplification.

The term "host," as used herein, refers to a unicellular or multicellular organism in which the virus can replicate, including cell lines and animals, and preferably a human. Alternatively, the host can be carrying a part of the viral genome, whose replication or function can be altered by the compounds of the present invention. The term host specifically refers to infected cells, cells transfected with all or part of the viral genome and animals, in particular, primates (including chimpanzees) and humans. In most animal applications of the present invention, the host is a human patient. Veterinary applications, in certain indications, however, are clearly anticipated by the present invention (such as bovine viral diarrhea virus in cattle, hog cholera virus in pigs, and border disease virus in sheep).

III. Host Primers and Probes

For the detection of host nucleic acids, any suitable primer and/or probe known in the art may be used. These primers and/or probes may be purchase or made by any means known in the art. There are several primers and/or probe combinations commercially available, for example the primer probe set for rRNA gene (Perkin Elmer/Applied Biosysterns). The latter set is often used as calibrator PCR in this invention. Alternatively, suitable probes and primers can be designed by using the Primer Express software (Applied Biosysterns, CA), and in particular new primers and probes for the β-actin gene, and for the mitochondrial cytochrome oxidase subunit II (COXII) gene.

β-Actin

In one embodiment, the nuclear DNA or RNA used to derive a set of oligonucleotides for the endogenous control is the DNA for β-actin. Any suitable primers and/or probes can be used. In a specific embodiment of the present invention, the primers and/or probes are complementary to sequences from the third exon of the human -actin gene (GenBandk accession number E01094). The probe comprises a reporter and quencher that provides a detectable signal upon amplification. Any reporter/quencher probe set can be used, including, but not limited to TaqMan, molecular beacons, single dye probe, SYBR green, Amplifluor probes and dual labeled probe sets.

In a preferred embodiment of the invention, the oligonucleotides used to amplify β-actin (primers) are sense 5'-GCGCGGCTACAGCTTCA-3' (SEQ ID NO: 1) and antisense 5'-TCTCCTTAATGTCACGCACGAT-3' (SEQ ID NO: 2). The labeled oligonulceotide (probe) used to detect host nucleic acid has a sequence of 5'-CACCACGGC-CGAGCGGGA-3' (SEQ ID NO: 3). In one embodiment, the probe is labeled with a reporter at the 5'-end and a quencher molecule at the 3'-end, and in particular, the reporter, FAM, at the 5' end, and the quencher molecule, TAMRA, at the 3' end.

Mitochondiral Nucleic Acid

In one embodiment, the mitochondrial nucleic acids can be specifically derived from mitochondrial DNA. In an alternate embodiment, the mitochondiral nucleic acids can be specifically derived from mitochondrial RNA. In an alternate embodiment, the mitochondiral nucleic acids are complementary to sequences from themitochondrial COXII gene. Any suitable primers and/or probes can be used. The probe comprises a reporter and quencher that provides a detectable signal upon amplification. Any reporter/quencher probe set can be used, including, but not limited to TaqMan, molecular beacons, single dye probe, SYBR green, Amplifluor probes and dual labeled probe sets.

In a preferred embodiment of the invention, the oligonucleotides used to amplify mitochondrial nucleic acids (primers) are sense 5'-TGCCCGCCATCATCCTA-3' (SEQ ID NO: 19) and 5'-TCGTCTGTTATGTAAAGGATGCGT-3' (SEQ ID NO: 20). The labeled oligonulceotide (probe) used to detect host nucleic acid has a sequence of 5'-TCCTCATCGCCCTC-CCATCCC-3' (SEQ ID NO: 21). In one embodiment, the probe is labeled with a reporter at the 5'-end and a quencher molecule at the 3'-end, and in particular, the reporter, TET, at the 5' end, and the quencher molecule, TAMRA, at the 3' end.

IV. Viral Primers and Probes

For viral targets, any suitable primer and/or probe known in the art may be used. These primers and/or probes may be purchase or made by any means known in the art. Alternatively, suitable probes and primers can be designed by using the Primer Express software (Applied Biosystems, CA), and in particular, primers and probes designed to be complementary to highly conserved areas. This is particularly important for viruses with a high genetic variability, like for example HCV, HBV, and HIV, BVDV and RSV.

Ideally, the viral primer/probe set should fulfill to the following criteria: (i) be able to detect the huge variability of clades or genotypes with the same efficiency; ii) have a dynamic range of at least five logs or higher; and iii) the lower limit of detection should be as low as a few viral copies/mL. Although variability at the PCR-primer binding sites is often problematic, RT-PCR based assays are some of the most sensitive technologies.

In one embodiment of the present invention, complementary viral sequences were designed based on conserved regions of the viral genome to obtain a unique combination of PCR primers and/or probe-set. In an alternative embodiment of the present invention, the primers/probes are designed based on predicted sequence conservation over the different genotypes. In a preferred embodiment, the primers/probes are designed based on both the conserved region of the viral genome and predicted sequence conservation over the different genotypes.

HIV

In one embodiment of the invention, the target viral nucleic acid is from HIV, and in particular, HIV-1. Any suitable primers and/or probes can be used. In a specific embodiment of the present invention, the primers and/or probes are complementary to the reverse transcriptase domain between codons 200 and 280. The probe comprises a reporter and quencher that provides a detectable signal upon amplification. Any reporter/quencher probe set can be used, including, but not limited to TaqMan, molecular beacons, single dye probe, SYBR green, Amplifluor probes and dual labeled probe sets.

In a preferred embodiment of the invention, the oligonucleotides used to amplify HIV-1 (primers) are sense 5'-TGGGT-TATGAACTCCATCCTGAT-3' (SEQ ID NO: 4) and antisense 5'-TGTCATTGACAGTCCAGCTGTCT-3' (SEQ ID NO: 5). The labeled oligonulceotide (probe) used to detect HIV-1 viral load has a sequence of 5'-TTTCTG-GCAGCTCTCGGCTGTACTGTCCATT-3' (SEQ ID NO: 6). In one embodiment, the probe is labeled with a reporter at the 5'-end and a quencher molecule at the 3'-end, and in particular, the reporter, FAM, at the 5' end, and the quencher molecule, TAMRA, at the 3' end.

HCV

In another embodiment of the invention, the target viral nucleic acid is from HCV. Any suitable primers and/or probes can be used. In a specific embodiment of the present invention, the primers and/or probes are derived from thighly conserved sequences complementary to the RNA sequences present in HCV, such as the HCV 5' non-coding region. The probe comprises a reporter and quencher that provides a detectable signal upon amplification. Any reporter/quencher probe set can be used, including, but not limited to TaqMan, molecular beacons, single dye probe, SYBR green, Amplifluor probes and dual labeled probe sets.

In a preferred embodiment of the invention, the oligonucleotides used to amplify HCV (primers) are sense 5'-AGC-CATGGCGTTAGTA(T/A)GAGTGT-3' (SEQ ID NO: 7) and antisense 5'-TTCCGCAGACCACTATGG-3' (SEQ ID NO: 8). The labeled oligonulceotide (probe) used to detect HCV viral load has a sequence of 5'-CCTCCAGGAC-CCCCCCTCCC-3' (SEQ ID NO: 9). In one embodiment, the probe is labeled with a reporter at the 5'-end and a quencher molecule at the 3'-end, and in particular, the reporter, FAM, at the 5' end, and the quencher molecule, TAMRA, at the 3' end.

BVDV

In another embodiment of the invention, the target viral nucleic acid is from BVDV. Any suitable primers and/or probes can be used. In a specific embodiment of the present invention, the primers and/or probes are derived from thighly conserved sequences complementary, such as sequences complementary to nucleotides 1611 to 1751 of the NS5B gene. The probe comprises a reporter and quencher that provides a detectable signal upon amplification. Any reporter/quencher probe set can be used, including, but not limited to TaqMan, molecular beacons, single dye probe, SYBR green, Amplifluor probes and dual labeled probe sets.

In a preferred embodiment of the invention, the oligonucleotides used to amplify BVDV (primers) are sense 5'-AGTCT-TCAGTTTCTTGCTGATGT-3' (SEQ ID NO: 10) and antisense 5'-TGTTGCGAAAGGACCAACAG-3' (SEQ ID NO: 11). The labeled oligonulceotide (probe) used to detect BVDV viral load has a sequence of 5'-AAATCCTCCTAA-CAAGCGGGTTCCAGG-3' (SEQ ID NO: 12). In one embodiment, the probe is labeled with a reporter at the 5'-end and a quencher molecule at the 3'-end, and in particular, the reporter, FAM, at the 5' end, and the quencher molecule, TAMRA, at the 3' end.

HBV

In another embodiment of the invention, the target viral nucleic acid is from HBV. Any suitable primers and/or probes can be used. In a specific embodiment of the present invention, the primers and/or probes are derived from thighly conserved sequences complementary to the DNA sequences present in HBV, such as the amino-terminal region of the HBV surface antigen gene. The probe comprises a reporter and quencher that provides a detectable signal upon amplification. Any reporter/quencher probe set can be used, including, but not limited to TaqMan, molecular beacons, single dye probe, SYBR green, Amplifluor probes and dual labeled probe sets.

In a preferred embodiment of the invention, the oligonucleotides used to amplify HBV (primers) are sense 5'-GGAC-CCCTGCTCGTGTTACA-3' (SEQ ID NO: 13) and antisense 5'-GAGAGAAGTCCACCACGAGTCTAG-3' (SEQ ID NO: 14). The labeled oligonulceotide (probe) used to detect HBV viral load has a sequence of 5'-TGTTGACAA(A/G)TCCT-CACAATACC(A/G)CAGA-3' (SEQ ID NO: 15). In one embodiment, the probe is labeled with a reporter at the 5'-end and a quencher molecule at the 3'-end, and in particular, the reporter, FAM, at the 5' end, and the quencher molecule, TAMRA, at the 3' end.

RSV

In another embodiment of the invention, the target viral nucleic acid is from RSV. Any suitable primers and/or probes can be used. In a specific embodiment of the present invention, the primers and/or probes are derived from thighly conserved sequences complementary, such as sequences complementary to nucleotides that encode for the RNA polymerase large subunit (L). The probe comprises a reporter and quencher that provides a detectable signal upon amplification. Any reporter/quencher probe set can be used, including, but not limited to TaqMan, molecular beacons, single dye probe, SYBR green, Amplifluor probes and dual labeled probe sets.

In a preferred embodiment of the invention, the oligonucleotides used to amplify RSV (primers) are sense 5'-CAA-CAACCCTAATCATGTGGTATCA-3' (SEQ ID NO: 16) and antisense 57-CCGGTTGCATTGCAAACA-3' (SEQ ID NO: 17). The labeled oligonulceotide (probe) used to detect RSV viral load has a sequence of 5'-TGACAGGCAAAGAAA-GAGAACTCAGTGTAGGTAGA-3' (SEQ ID NO: 18). In one embodiment, the probe is labeled with a reporter at the 5'-end and a quencher molecule at the 3'-end, and in particular, the reporter, FAM, at the 5' end, and the quencher molecule, TAMRA, at the 3' end.

V. Methods

Amplification Procedure

The process for amplification of a desired nucleic acid sequence can be achieve by any means necessary to achieve amplification of the desired amplicon. The amplification can be achieved using any known means in the art, including polymerase chain reaction techniques. The primers and probes can be purchased or prepared by any means known in the art, including automated processes. In a preferred embodiment, the primers and probes are designed for specificity for the target nucleic acid sequence, as disclosed herein.

The enzymes used to promote amplification can be purchased or can be prepared by any means known in the art, including cellular extraction. Substrates to aid in the amplification can also be purchased or can be prepared by any means known in the art, including any synthetic methodology to synthesis natural and unnatural nucleic acids. The enzyme and substrates can be added to the amplification mixture at any time and order that allows for the amplification of the desired amplicon. In a preferred embodiment, the polymerase and substrates follow TaqMan 7700 chemistry provided by Applied Biosystems in California.

Additionally, amplification conditions vary depending on the choice of primers and probes, due to differences in their melting temperatures™. Preferred temperatures are from 50° C. to 95° C. for incubation and 60° C. to 95° C. for amplification. The temperature for amplification can be done at any temperature that allows for replication of the desired amplicon at a suitable rate. As an exemplary embodiment, reverse-transcriptase polymerase chain reaction ("RT-PCT") can be used to amplify the desired amplicon. After reverse transcription incubation, an amplification cycle can be performed. The incubation cycle can be performed at one temperature or on a multi-temperature basis; for example, the incubation cycle can be performed on a two-step temperature gradient, preferably, first a moderate time at moderate temperature followed by an extended period at higher temperatures. The amplification cycle can be performed at one temperature or on a multi-temperature basis; for example, the amplification cycle can be performed on a two-step gradient, preferably, first a short phase of higher temperatures followed by a longer period of moderate temperatures. The amplification procedure can be repeated as many times as necessary, but preferably repeated around 40 times.

As a non-limiting example, HIV-1, β-actin and mitochondrial nucleic acid sequences can be amplified using the following procedure. First the amplification reaction mixture is incubated for two minutes at 50° C., then ten minutes at 95° C. This is then followed by forty cycles of a two-step amplification reaction at 95° C. for fifteen seconds then sixty seconds at 60° C.

Detection Systems

The presence of the amplicon can be detected in real time based on the labeled oligonucleotide, which is labeled with a variety of substances, termed reporting dyes, and quenching dye, which upon amplification, are capable of emitting a detectable signal. Any combination of reporting dyes and quenching dyes can be used. Some non-limiting examples of reporting dyes are FAM, VIC, PAT and JOE. A non-limiting example of quenching dyes is TAMRA. These reporting dyes and quenching dyes can be purchased or can be prepared by any means known in the art, including radical and organometallic chemistry.

In one embodiment, the detectable signal is a fluorescent dye that can be detected in a spectrometer that is covalently bound to a quenching dye through the oligonucleotide. This renders the fluorescent dye inactive while bound to the oligonucleotide. However, upon exonuclease degradation of the oligonucleotide, the fluorescent dye can be released from the quenching dye, thus emitting a detectable signal.

Many of the new DNA tags and labels depend on two phenomena that are extensions of fluorescence: quenching and energy transfer. In general, anything that reduces the lifetime of the excited state decreases the quantum yield of the fluorophore; anything that decreases the quantum yield is called quenching. There are three main mechanisms for determining these phenomena: collisional, in which the excited state of the fluorophore loses its energy by bumping into a nonfluorescent molecule; static, in which the excited state reacts with the quencher, forming a nonfluorescent complex; and energy transfer, which involves the nonradiative transfer of energy from a donor to an acceptor.

The brightness of a fluorescent dye depends on many parameters. The parameters can be divided between the physical and chemical properties of the dyes and the excitation system. The important physical properties of the dyes are quantum yield and extinction coefficient. The quantum yield is an expression of the number of photons emitted divided by the number of photons absorbed. A quantum yield of 0 indicates a nonfluorescent molecule, and a quantum yield of 1 indicates that 100 percent of the excitation photons result in lower-wavelength emitted photons. The extinction coefficient is an expression of the probability that a photon of a given wavelength will be absorbed by the fluorophore. A high extinction coefficient combined with a high quantum yield generally leads to a "bright" fluorophore; fluorescein, for example, is a relatively "bright" dye, having an extinction coefficient of about 80,000 at its absorption maximum and a quantum yield of ~0.9.

For fluorescence resonant energy transfer (FRET) to occur, there must be a precise overlap in quantum energy levels between the donor and the acceptor, the energy being transferred by dipolar coupling rather than emission and reabsorption of a photon. FRET has been used very productively to create dyes for DNA sequencing, where a common donor eliminates the need for multiple excitation wavelengths but instead transfers its energy to four separate dyes that have easily discernable emission spectra. FRET and fluorescence quenching are very distance dependant, allowing their exploitation in several novel assays that alter donor-acceptor geometries.

Many of the methods described depend on a variety of modified oligonucleotides. Many fluorescent dyes are available as dye-phosphoramidites (or as dye-CPG derivatives), which are compatible with automated oligonucleotide synthesis methods. Using this approach, dyes can be incorporated at the 5' or 3' end or at any internal position during routine synthesis. Similarly, amino-modified bases can be incorporated into an oligo at any position, enabling a wider variety of labeling, because many additional dyes are available in an NHS-ester form that can be conjugated to an amino-modified oligonucleotide after synthesis. Different applications call for different modifications, including such esoterica as variable-length spacers, universal bases and branched backbones.

Reagent kits that support quantitative amplification and detection in multiplex are commercially available. The QPCR kits are used with DNA templates, either to detect DNA mutations or to measure gene or viral copy number. The QRT-PCR kits are used with RNA templates, typically for measuring RNA levels. Mutations can also be detected in expressed RNA with these kits. These kits have the capability of high performance with various fluorescent detection systems, including, the AmpliFluor system, molecular beacons, TaqMan® probes, dual fluorophore approach, single-dye primers and DNA bynding dyes.

(i) Amplifluor Universal Amplification and Detection System, Intergen Co., Purchase, N.Y.

In this system, PCR amplification and detection steps take place in the same reaction vessel. Resultant PCR products fluoresce and can be monitored with real-time or endpoint fluorescence detection instruments. The Amplifluor system is based on an innovative adaptation of the molecular beacon technology. Molecular beacons are hairpin-shaped oligonucleotides that contain fluorophore and quencher moieties. Molecular beacons act like switches that are normally closed to bring the fluorophore/quencher pair together to turn fluorescence "off." When prompted to undergo conformational changes that open the hairpin structure, the fluorophore and quencher are separated, and fluorescence is turned "on." Similarly, the Amplifluor system uses a primer that contains a hairpin-shaped end in which fluorescein is paired up with the quencher 4-(dimethylamine)azo benzene sulfonic acid (DABSYL). However, Intergen points out that there is an important difference between the Amplifluor system and other currently available energy transfer-based PCR methods (e.g., molecular beacons or Perkin-Elmer's Taqman™. In Amplifluor, the fluorescent oligonucleotides are actually incorporated into the reaction products. This enables the direct detection of PCR products, reducing the number of false positive reactions, which can be caused by even the most minimal carry-over contamination. Three primers are used to amplify products with Intergen's Amplifluor system. Forward and reverse primers specific for the gene of interest are generated by the user. Additionally, reactions contain the UniPrimer™ Energy-Transfer-labeled Primer—the key component of the Amplifluor system. The 5' end of UniPrimer consists of a hairpin structure labeled with fluorescein and DABSYL. A tail sequence (Z) is at the primer's 3' end. The Z sequence acts as a universal PCR primer; it is specifically designed to reduce PCR background due to heterodimer formation. Any PCR reaction can be adapted to the Amplifluor system by synthesizing a modified version of one of the target-specific primers (the Z sequence is simply added to the 5' end of the modified primer). Conventional post-PCR detection methods such as gel electrophoresis or dot blot techniques are not required.

(ii) Molecular Beacon

The molecular beacon is a hairpin-shaped oligo with a loop sequence complementary to part of the target sequence and flanked by two arms that anneal to form a short (5-7 base pair) stem. At the end of one arm is a fluorophore and at the other a quencher that prevents fluorescence when the stem is intact. However, with careful consideration given to the relative stability of the stem versus that of the beacon-target hybrid, the oligo is designed to remain folded in free solution but to readily hybridize to any available target; once hybridized, the quencher is moved away from the fluorophore, which then fluoresces to signal that target is present. Molecular beacons thus can be used to monitor real-time PCR by using a target sequence in the middle of the amplicon and measuring fluorescence during the annealing step of PCR.

In order to detect multiple targets in the same solution, molecular beacons can be made in many different colors utilizing a broad range of fluorophores. Dabcyl, a non-fluorescent chromophore, serves as the universal quencher for any fluorophore in molecular beacons. Owing to their stem, the recognition of targets by molecular beacons is so specific that single-nucleotide differences can be readily detected. Because of these properties, molecular beacons have been used for the detection of RNAs within living cells, for monitoring the synthesis of specific nucleic acids in sealed reaction vessels, for homogenous one-tube assays for genotyping single-nucleotide variations in DNA and for multiplex PCRs for the detection of four different pathogenic retroviruses (Vet et al., 1999).

When fully optimized, molecular beacons make for efficient detection systems, but occasionally some pitfalls are encountered. False positives or low signal-to-background can result from impure preparations that contain free fluorophores or from oligos with a fluorophore but no quencher, or from design problems such as a stem that is too strong at low temperatures. Care must be taken with design as well as with the necessary control experiments to ensure that molecular beacons operate as intended.

(iii) TaqMan probe.

A cousin of the molecular beacon is the TaqMan probe from Applied Biosystems of Foster City, Calif. This system exploits the 5' exonuclease activity of Taq DNA polymerase. During the PCR extension an annealed oligonucleotide that has a reporter fluorophore at the 5' exonuclease and a quencher at the 3' exonuclease is chewed up by a polymerase 5'-3' exonuclease activity, releasing the fluorophore from its quencher (the presence of the TaqMan probe doesn't significantly inhibit PCR product synthesis). The resulting fluorescence is proportional to the amount of PCR product.

(iv) The Dual Fluorophore

An alternative to the fluorophore-quencher system is a dual fluorophore approach that exploits FRET. This is the principle behind the LightCycler hybridization probes from Roche Molecular Biosystems of Indianapolis. Two oligo probes, rather than TaqMan's one, anneal to the amplicon; one carries a fluorescein label (the FRET donor) at its 3' end and the second is labeled with LC red 640 (the FRET acceptor) at its 5' end. The oligos are designed to hybridize in a head-to-tail orientation with the fluorophores separated at a distance that is compatible with efficient energy transfer.

(v) Fluorescent Oligonucleotides for Homogeneous Detection, Life Technologies, Inc.

A novel fluorescent detection system that does not require a quenching moiety for homogeneous detection was developed. The technology is based on oligonucleotides labeled with a single fluorophore with significant increase in fluorescence intensity upon hybridization or incorporation into double stranded DNA. This detection technology is a platform for fluorescent detection of nucleic acids in real time as well as in closed tube endpoint formats. This detection methodology has been used as hybridization probes and as amplification primers in homogenous PCR amplification assays.

(vi) SYBR Green I Dye

The fluorescent dye SYBR Green I binds to the minor groove of the DNA double helix. In solution, the unbound dye exhibits very little fluorescence, however, fluorescence is greatly enhanced upon DNA-binding. SYBR Green I dye is very stable (only 6% of the activity is lost during 30 amplification cycles).

At the beginning of amplification, the reaction mixture contains the denatured DNA, the primers and the dye. The unbound dye molecules weakly fluoresce, producing a minimal background fluorescence signal which is subtracted during computer analysis.

After annealing of the primers, a few dye molecules can bind to the double strand. DNA binding results in a dramatic increase of the SYBR Green I molecules to emit light upon excitation.

During elongation, more and more dye molecules bind to the newly synthesized DNA. If the reaction is monitored continuously, an increase in fluorescence is viewed in real-time. Upon denaturation of the DNA for the next heating cycle, the dye molecules are released and the fluorescence signal falls.

Fluorescence measurement at the end of the elongation step of every PCR cycle is performed to monitor the increasing amount of amplified DNA. To separate specific from unspecific signals fluorescence can be measured at high temperature. The unspecific products usually melt at a much lower temperature than the specific product. Therefore, the specificity of the signal can be significantly enhanced if the temperature is raised near to the melting point of the specific fragment (vii) Other DNA Binding Dyes/Intercalators:

DNA binding dyes, some of which are intercalators, bind double-stranded DNA and to a lesser extent single-stranded DNA and RNA. With some of these dyes, binding to DNA substantially increases the intensity of their fluorescence. Dimeric dyes are noteworthy for their higher affinity. RNA and single-stranded DNA stains can be used to detect RNA and single stranded DNA.

Other methods of detection are described in J. Ju et al., "Fluorescent energy transfer dye-labeled primers for DNA sequence analysis," *Proceedings of the National Academy of Sciences*, 92:4347-51, 1995; S. Tyagi, F. R. Kramer, "Molecular beacons: probes that fluoresce upon hybridization," *Nature Biotechnology*, 14:303-8, 1996; A. J.-C. Eun, S.-M. Wong, "Molecular beacons: A new approach to plant virus detection," *Phytopathology*, 90:269-75, March 2000; L. G. Kostrikis et al., "Spectral genotyping of human alleles," *Science*, 279:1228-19, 1998; G. Bonnet et al., "Thermodynamic basis of the enhanced specificity of structured DNA probes," *Proceedings of the National Academy of Sciences*, 96:6171-6, 1999; R. D. Oberst et al., "PCR-based DNA amplification and presumptive detection of *Escherichia coli* O157:H7 with an internal fluorogenic probe and the 5' nuclease (TaqMan) assay," *Applied and Environmental Microbiology*, 64:3389-96, 1998; I. Tapp et al., "Homogenous scoring of single-nucleotide polymorphisms: comparison of the 5'-nuclease TaqMan assay and Molecular Beacon probes," *Biotechniques*, 28:732-8, April 2000; I. A. Nazarenko et al., "A closed tube format for amplification and detection of DNA based on energy transfer," *Nucleic Acids Research*, 25:2516-21, 1997; G. J. Nuovo et al., "In situ amplification using universal energy transfer-labeled primers," *The Journal of Histochemistry and Cytochemistry*, 47:273-9, 1999; D. Schuster, "Novel fluorescent oligonucleotides for homogenous detection and quantitation of nucleic acids," Abstracts from the Cambridge Healthcare Institute's fifth annual conference on Gene Quantification; Tyagi S and Kramer FR (1996) Molecular beacons: probes that fluoresce upon hybridization. Nat Biotechnol 14, 303-308; Tyagi S, Bratu D P, and Kramer F R (1998) Multicolor molecular beacons for allele discrimination. Nat Biotechnol 16, 49-53; Matsuo T (1998) In situ visualization of mRNA for basic fibroblast growth factor in living cells. Biochimica Biophysica Acta 1379, 178-184; Sokol D L, Zhang X, Lu P, and Gewirtz A M (1998) Real time detection of DNA-RNA hybridization in living cells. Proc Natl Acad Sci USA 95, 11538-11543; Leone C, van Schijndel H, van Gemen B, Kramer F R, and Schoen C D (1998) Molecular beacon probes combined with amplification by NASBA enable homogeneous, real-time detection of RNA. Nucleic Acids Res 26, 2150-2155; Piatek A S, Tyagi S, Pol A C, Telenti A, Miller L P, Kramer F R, and Alland D (1998) Molecular beacon sequence analysis for detecting drug resistance in *Mycobacterium tuberculosis*. Nat Biotechnol 16, 359-363; Kostrikis L G, Tyagi S, Mhlanga M M, Ho D D, and Kramer F R (1998) Spectral genotyping of human alleles. Science 279, 1228-1229; Giesendorf B A, Vet J A, Tyagi S, Mensink E J, Trijbels F J, and Blom H J (1998) Molecular beacons: a new approach for semiautomated mutation analysis. Clin Chem 44, 482-486; Marras S A, Kramer F R, and Tyagi S (1999) Multiplex detection of single-nucleotide variations using molecular beacons. Genet Anal 14, 151-156; and Vet J A, Majithia A R, Marras S A, Tyagi S, Dube S, Poiesz B J, and Kramer F R (1999) Multiplex detection of four pathogenic retroviruses using molecular beacons. Proc Natl Acad Sci USA 96, 6394-6399.

VI. Quantitative Real-Time Polymerase Chain Reaction Using TaqMan

Quantitative real-time polymerase chain reaction using TaqMan and the Perkin-Elmer/Applied Biosystems division 7700 sequence detector (PE/ABD 7700) provides an accurate method for determination of levels of specific DNA and RNA sequences in samples. It is based on detection of a fluorescent signal produced proportionally during amplification of a PCR product.

Quantitative real-time PCR using the PE/ABD 7700 is based on detection of a fluorescent signal produced proportionally during the amplification of a PCR product. The chemistry is the key to the detection system. A probe is designed to anneal to the target sequence between the traditional forward and reverse primers. The probe is labeled at the 5' end with a reporter fluorochrome (usually 6-carboxyfluorescein [6-FAM]) and a quencher fluorochrome (6-carboxy-tetramethyl-rhodamine [TAMRA]) added at any T position or at the 3' end. The probe is designed to have a higher Tm than the primers, and during the extension phase, the probe must be 100% hybridized for success of the assay. As long as both fluorochromes are on the probe, the quencher molecule stops all fluorescence by the reporter. However, as Taq polymerase extends the primer, the intrinsic 5' to 3' nuclease activity of Taq degrades the probe, releasing the reporter fluorochrome. The amount of fluorescence released during the amplification cycle is proportional to the amount of product generated in each cycle.

The 7700 detection system consists of a 96-well thermal cycler connected to a laser and charge-coupled device (CCD) optics system. An optical fiber inserted through a lens is positioned over each well, and laser light is directed through the fiber to excite the fluorochrome in the PCR solution. Emissions are sent through the fiber to the CCD camera, where they are analyzed by the software's algorithms. Collected data are subsequently sent to the computer.

The sensitivity of detection allows acquisition of data when PCR amplification is still in the exponential phase. This is determined by identifying the cycle number at which the reporter dye emission intensities rises above background noise; this cycle number is called the threshold cycle (Ct). The Ct is determined at the most exponential phase of the reaction and is more reliable than end-point measurements of accumulated PCR products used by traditional PCR, methods. The Ct is inversely proportional to the copy number of the target template; the higher the template concentration, the lower the threshold cycle measured.

There are many advantages to quantifying gene sequences using this technology, foremost being sensitivity and precision. This precision exists because quantification of the gene sequence is determined by the Ct, which is calculated during the exponential phase of the reaction. High specificity is conferred by the requirement of three oligos to anneal to the DNA before any data are collected.

Competitive PCR is another technique often used to quantify DNA or RNA. Optimization of competitive PCR is laborious and time consuming. Several dilutions of target sequences must be tested to achieve a suitable ratio of target to competitor, and efficiencies of target and competitor must be similar. This assay is linear only over a very short range compared with quantification with the 7700. The number of samples that can be processed is also a limiting factor.

The applications for quantitative real-time PCR are innumerable. Detection of genomic or viral DNA in tissues can be a valuable diagnostic tool. Gene expression can be measured after extraction of total RNA and preparation of cDNA by a reverse transcription (RT) step. Setup and analysis are simple and can more easily be extended to the clinical environment than traditional PCR techniques.

Optimization of the PCR reaction is required for each primer and probe set. The optimal Mg2+ concentration is usually between 4 and 6 mM but sometimes can be as low as 2 mM. Optimal primer concentrations are usually between 100 and 800 nM. Optimization requires varying the concentration of one primer relative to the other, because the optimal concentration may not be the same for both. The optimal probe concentration may be as low as 50 nM or as high as 200 nM. The optimal Mg2+ concentration and reverse primer concentration must also be validated for the RT step.

The detection system is so sensitive that fewer than 10 copies of DNA can be detected. Aerosol contamination of primers and probes is a potential problem if samples are prepared in the laboratory where DNA is being extracted.

For determination of pathogens, total nucleic acids are isolated. A specific cDNA can be produced by using the same reverse primer used in the PCR reaction or by using random hexamer primers to produce a range of cDNA products. RNA can easily be prepared using kits such as RNAEasy from Qiagen (Valencia, Calif., USA) and Triazol from Life Technologies (Gaithersburg, Md., USA).

Multiplexing quantitative PCR reactions by using more than one fluorescent dye per tube became available for internal tube controls. Kits are available for 18S ribosomal RNA or for glyceraldehyde-3-phosphate dehydrogenase (GAPDH) as a control. These two fluorochromes are preferred for use with FAM, the reporter used on the probe.

If copy number is required, standard curves of plasmid DNA can be constructed and assayed each time with samples containing the target gene sequence. If the starting molecule is RNA, cRNA can be prepared and used as a standard. Kits are available to prepare RNA from plasmids containing the gene sequence. T7, T3, or SP6 primers typically are used to prepare the cRNA. The cRNA produced must be validated in the RT and PCR reactions to determine if it is transcribed and amplified at the same efficiency as the sample RNA present in a mixture of extracted RNAs.

Other important controls are no-amplification controls (NACs) and no-template controls (NTCs). NACs test for contamination of RNA by genomic DNA. NTCs test for the contamination of assay reagents.

Several types of reaction mixes are available. The TaqMan Universal PCR Master Mix, contains the core reagents in an easy to use 2× solution. The TaqMan Gold RT-PCR kit allows one-step or two-step RT-PCR. The one-step option allows an investigator to set up the RT and PCR steps without opening the tube, whereas the two-step option separates the RT step from the PCR. Master mixes can also be assembled by purchasing the various components, such as NTPs, buffer, Mg2+, and Taq polymerase, from many other companies offering molecular biology reagents.

Primers and probes must be carefully designed. The Primer Express software, which is specifically designed to select the primers and probes takes into account the required parameters for well-designed primers and probe. These parameters include a Tm for the probe that is 10° C. higher than the primers, primer Tms between 58° C. and 60° C., amplicon size between 50 and 150 bases, absence of 5' Gs, and primer length.

The best design for primers and probes to use for the quantification of RNA expression requires positioning of a primer or the probe in a conserved region of the virus, or in case of genetic testing, over an intron.

VII. Kits

In addition, the present invention also provides for a kit for use in conducting viral assays for efficacy that includes a mixture of oligonucleotides, the mixture containing at least one the first primer and/or probe set that provides a detectable signal on the occurrence on the transcription of viral nucleic acid; and at least one primer and/or probe set provides a second detectable signal on the occurrence on the transcription of host nucleic acid.

The present invention also provides for a kit for use in conducting toxicity assays for efficacy that includes a mixture of oligonucleotides, the mixture containing at least one the first primer and/or probe that provides a detectable signal on the occurrence on the transcription of host mitochondrial nucleic acid; and at least one primer and/or probe provides a second detectable signal on the occurrence on the transcription of host nuclear nucleic acid.

In particular, the kit comprises a primer/probe set for host nucleic acid wherein the primers are given by SEQ ID NO: 1 and 2, and the probe is a sequence given by SEQ ID NO: 3 along with a fluorescent dye and quenching dye.

In particular, the kit comprises a primer/probe set for viral nucleic acid for HIV-1 wherein the primers are given by SEQ ID NO: 4 and 5, and the probe is a sequence given by SEQ ID NO: 6 along with a fluorescent dye and quenching dye.

In particular, the kit comprises a primer/probe set for viral nucleic acid for HCV wherein the primers are given by SEQ ID NO: 7 and 8, and the probe is a sequence given by SEQ ID NO: 9 along with a fluorescent dye and quenching dye.

In particular, the kit comprises a primer/probe set for viral nucleic acid for BVDV wherein the primers are given by SEQ ID NO: 10 and 11, and the probe is a sequence given by SEQ ID NO: 12 along with a fluorescent dye and quenching dye.

In particular, the kit comprises a primer/probe set for viral nucleic acid for HBV wherein the primers are given by SEQ ID NO: 13 and 14, and the probe is a sequence given by SEQ ID NO: 5 along with a fluorescent dye and quenching dye.

In particular, the kit comprises a primer/probe set for viral nucleic acid for RSV wherein the primers are given by SEQ ID NO: 16 and 17, and the probe is a sequence given by SEQ ID NO: 18 along with a fluorescent dye and quenching dye.

In particular, the kit comprises a primer/probe set for host mitochondiral nucleic acid wherein the primers are given by SEQ ID NO: 19 and 20, and the probe is a sequence given by SEQ ID NO: 21 along with a fluorescent dye and quenching dye.

This invention is further illustrated in the following sections. The examples contained therein are set forth to aid in an understanding of the invention. The following examples are illustrative of the processes and products of the present invention; but this section is not intended to, and should not be interpreted to, limit in any way the invention set forth in the claims that follow thereafter. Equivalent, similar, or suitable solvents, reagents or reaction conditions may be substituted

EXAMPLES

Example 1

HIV-1 Cell culture

Human PBMC ($1\times10^6$ cells/T25 flask) were PHA stimulated for 2 days, and infected with either a sensitive (xxBRU) or a 3TC-resistant (184V) HIV-1 strain at 100 $TCID_{50}$. The culture was kept for 5 days in presence of test antiviral compounds at serial 1-log dilutions. Subsequently, human PBMC were removed from the culture supernatant by centrifugation (10 min, 400×g, 4° C.). This clarified supernatant was tested either in the RT-assay, or in the real-time RT-PCR assay.

Example 2

Reverse Transcriptase (RT) Assay

Virus particles present in a 1 mL aliquot of culture supernatant were concentrated by centrifugation (2 hr, 20,000×g, 4° C.). After the 2 hour spin, supernatant fluid was removed completely and the virus pellet was dispensed into a 100 µL Virus Solubilization Buffer (VSB: 0.5% Triton X-100; 0.8 M NaCl, 0.5 mM phenylmethylsulfonyl, 20% glycerol, 50 mM Tris.HCl pH 7.8). A 10 µL aliquot of RT-VSB was mixed with 75 µL RT cocktail (60 mM Tris.HCl pH 7.8, 12 mM $MgCl_2$, 6 mM DTT, 6 µg/mL Poly (rA)-Poly (dT), 1.2 mM dATP, and 80 µCi/mL $H^3$-TTP) and incubated for 2 hr at 37° C. Subsequently 100 µL of 10% TCA was added, and the total amount of incorporated $H^3$-TTP was counted.

Example 3

RT-PCR Primer and Probe Assessment

The TaqMan probe and primers were designed by using the Primer Express software (Applied Biosystems, CA) and are covering highly conserved sequences complementary to the DNA sequences present in HIV-1 RNA. By scanning the different genotypes of group M for regions containing only minor variability, the conserved domain was discovered. As a result, the region in the HIV-1 RT domain between codon 200 and 280 fulfilled the required criteria; thus this region was used to design an appropriate set of primers and probe that could work in real time PCR ("RT-PCR"). Primer sequences are as follows: sense 5'-TGGGTTATGAACTCCATCCT-GAT-3' (SEQ ID NO: 4) and 5,-TGTCATTGACAGTC-CAGCTGTCT-3' (SEQ ID NO: 5); the probe sequence is 5'-fluoresent dye-TTTCTGGCAGCACTATAGGCTG-TACTGTCCATT-quenching dye-3'(SEQ ID NO: 22). In this particular case, the probe was labeled with FAM at the 5' end, and the quencher molecule is TAMARA, provided at the 3' end. Any other combination of reporter and quencher dyes can be used as well.

The primer and probe set gave a linear range over 6 logs when tested on serial 1-log dilutions of cultured virus. In order to evaluate this primer/probe set with an FDA approved methodology for viral load measurement, a 1-log dilution series of a clinical HIV-1 genotype B isolate (attenuated in vitro to obtain a high viral load) was tested by real time RT-PCR and by Roche Amplicor HIV-1 Monitor (FIG. 1). In this experiment, the $10^{-6}$ diluted sample became positive at threshold cycle (Ct=35.52), which corresponded with a 1410 copies/mL in the Roche monitor HIV-1 version II assay. When validated over a dynamic range of 3 logs of virus, there was perfect correlation between the two methodologies (FIG. 1) with a lower limit of detection for the real-time RT-PCR assay of 141 copies/mL (Ct=38.85).

Example 4

Real-time RT-PCR Assay

The real-time RT-PCR technology was evaluated against the NASBA HIV-1 viral load assay. HIV-1 nucleic acid sequences was amplified using the designed probes and primers as described above. Viral RNA present in the culture supernatant was prepared using commercially available columns (QIAamp Viral RNA mini Kit, Qiagen, CA). The amplification reaction mixture was incubated for two minutes at 50° C., then ten minutes at 95° C. Then, the mixture was amplified using forty cycles of a two-step amplification reaction at 95° C. for fifteen seconds then sixty seconds at 60° C. Real-time RT-PCR-amplified RNA was detected in real-time by monitoring increases in fluorescence signal that resulted from degradation of a quenched fluorescent probe molecule following to the hybridization of the probe to the amplified viral DNA (TaqMan 7700 chemistry, Applied Biosystems, CA).

A total of 5 µL RNA was RT-amplified using reagents and conditions as described by the manufacturer (Applied Biosystems, CA). The standard curve ranged from $1.41\times10^2$ copies/mL to over $1.41\times10^8$ copies/mL. Copy numbers were calibrated using the Roche Amplicor HIV-1 Monitor test™ (Roche Diagnostics, Branchburg, N.J.), or the NASBA HIV-1 viral load assay (Organon Technika).

Figure 2:
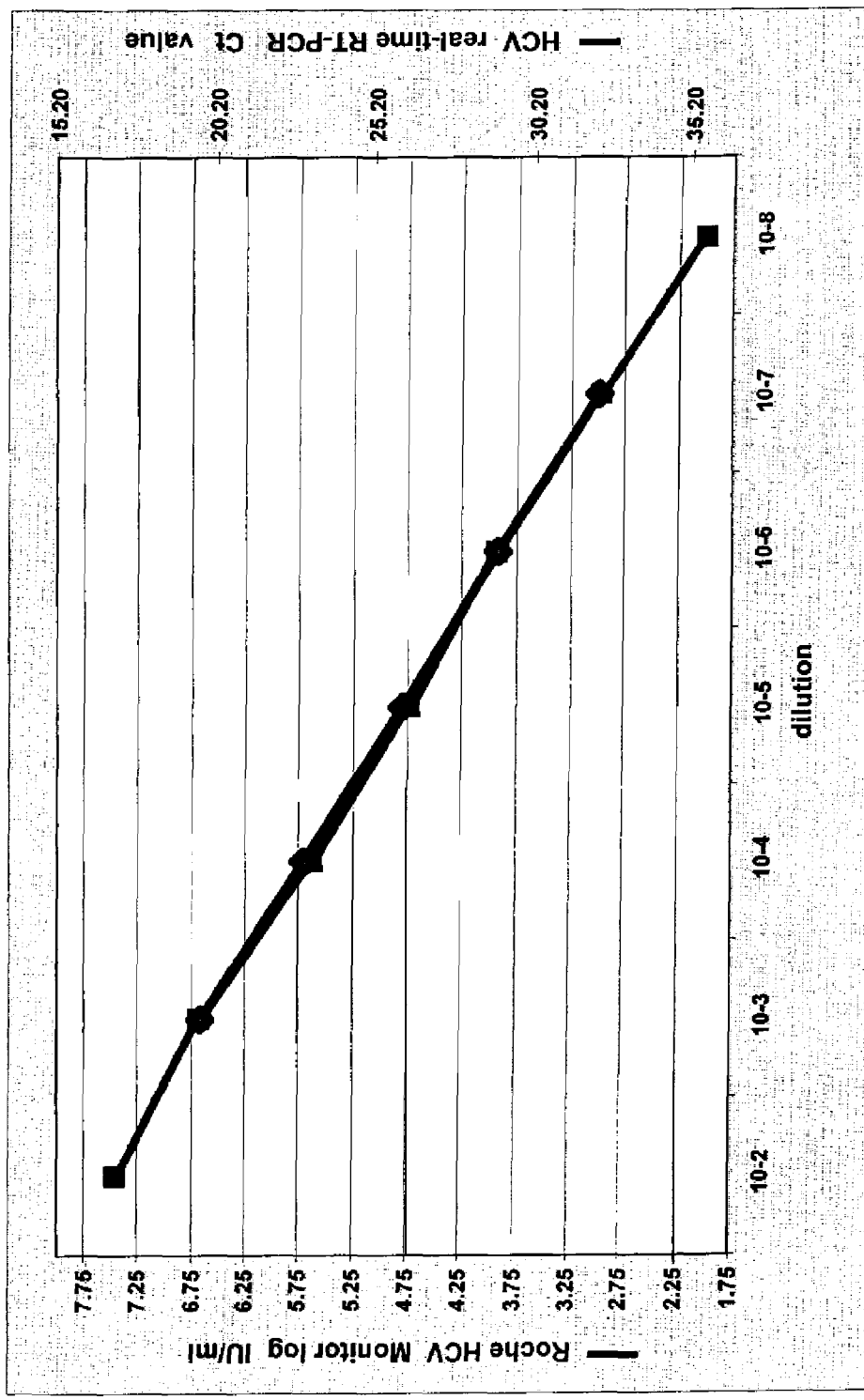
FIG. 2 is a graph that depicts the correlation of real-time RT-PCR for HIV-1 with NASBA HIV-1 technology. HIV-1 infected samples were taken from SCID-mice experiments. The 99% confidence intervals are indicated with dashed lines.

Samples containing HIV-1 (genotype B) over a range of 3 logs ($5\times10^3$ to $5\times10^6$ copies/mL) were tested in both methodologies. The correlation between the two methodologies is shown in FIG. 2. All samples tested felt within the 95% confidence interval, and only 2 samples were outside the 99% confidence interval. It can be concluded that the currently designed primer and probe set allowed reliable quantification of the both clinical samples and HIV-1 in vitro virus preparations. The real-time-RT-PCR has a lower limit of detection of 141 copies/mL and showed linearity over 6-logs of virus dilution.

Example 5

Optimization

Optimization of the PCR reaction is required for each primer and probe set. The optimal Mg2+ concentration is usually between 4 and 6 mM but sometimes can be as low as 2 mM. Optimal primer concentrations are usually between 100 and 800 nM. Optimization requires varying the concentration of one primer relative to the other, because the optimal concentration may not be the same for both. The optimal probe concentration may be as low as 50 nM or as high as 200 nM. The optimal Mg2+ concentration and reverse primer concentration must also be validated for the RT step.

Potential Contamination

The detection system is so sensitive that fewer than 10 copies of DNA can be detected. Aerosol contamination of primers and probes is a potential problem if samples are prepared in the laboratory where DNA is being extracted.

Sample Preparation

For determination of pathogens, total nucleic acids are isolated. A specific cDNA can be produced by using the same reverse primer used in the PCR reaction or by using random hexamer primers to produce a range of cDNA products. RNA can easily be prepared using kits such as RNAEasy from Qiagen (Valencia, Calif., USA) and Triazol from Life Technologies (Gaithersburg, Md., USA).

Controls

Multiplexing quantitative PCR reactions by using more than one fluorescent dye per tube became available for internal tube controls. Kits are available for 18S ribosomal RNA or for glyceraldehyde-3-phosphate dehydrogenase (GAPDH) as a control. These two fluorochromes are preferred for use with FAM, the reporter used on the probe.

If copy number is required, standard curves of plasmid DNA can be constructed and assayed each time with samples containing the target gene sequence. If the starting molecule is RNA, CRNA can be prepared and used as a standard. Kits are available to prepare RNA from plasmids containing the gene sequence. T7, T3, or SP6 primers typically are used to prepare the cRNA. The cRNA produced must be validated in the RT and PCR reactions to determine if it is transcribed and amplified at the same efficiency as the sample RNA present in a mixture of extracted RNAs.

Other important controls are no-amplification controls (NACs) and no-template controls (NTCs). NACs test for contamination of RNA by genomic DNA. NTCs test for the contamination of assay reagents.

Reaction Mix

Several types of reaction mixes are available. The TaqMan Universal PCR Master Mix, contains the core reagents in an easy to use 2× solution. The TaqMan Gold RT-PCR kit allows one-step or two-step RT-PCR. The one-step option allows an investigator to set up the RT and PCR steps without opening the tube, whereas the two-step option separates the RT step from the PCR. Master mixes can also be assembled by purchasing the various components, such as NTPs, buffer, Mg2+, and Taq polymerase, from many other companies offering molecular biology reagents.

Primer and Probe Design

Primers and probes must be carefully designed. The Primer Express software, which is specifically designed to select the primers and probes takes into account the required parameters for well-designed primers and probe. These parameters include a Tm for the probe that is 10° C. higher than the primers, primer Tms between 58° C. and 60° C., amplicon size between 50 and 150 bases, absence of 5' Gs, and primer length.

The best design for primers and probes to use for the quantification of RNA expression requires positioning of a primer or the probe in a conserved region of the virus, or in case of genetic testing, over an intron.

The protocol for Real-Time PCR can be achieved by any means known in the art. See, for example; Gibson U E M, Heid C A, Williams P M. A novel method for real-time quantitative RT-PCR. Genome Res 1996; 6:995-1001; Heid C A, Stevens J, Livak K J, Williams P M. Real-time quantitative PCR. Genome Res 1996; 6:986-994; Livak K J, Flood S J A, Marmaro J, Giusti W, Deetz K. Oligonucleotides with fluorescent dyes at opposite ends provide a quenched probe system useful for detecting PCR product and nucleic acid hybridization. PCR Methods Appl 1995; 4:357-362; Holland P M, Abramson R D, Watson R, Gelfand D H. Detection of specific polymerase chain reaction product by utilizing the 5'-3' exonuclease activity of *Thermus aquaticus* DNA polymerase. Proc Natl Acad Sci USA 1991; 88:7276-7280; Gerard C J, Olsson K, Ramanathan R, Reading C, Hanania E G. Improved quantitation of minimal residual disease in multiple myeloma using real-time polymerase chain reaction and plasmid-DNA complementarity determining region III standards. Cancer Res 1998; 58:3957-3964; Gelmini S, Orlando C, Sestini R, et al. Quantitative polymerase chain reaction-based homogeneous assay with fluorogenic probes to measure c-erB-2 oncogene amplification. Clin Chem 1997; 43:752-758; deKok J B, Hendriks J C M, van Solinge WW, Willems H L, Mensink E J, Swinkels D W. Use of real-time quantitative PCR to compare DNA isolation methods. Clin Chem 1998; 44:2201-2204; Lockey C, Otto E, Long Z. Real-time fluorescence detection of a single DNA molecule. Biotechniques 1998; 24:744-746; Marcucci G, Livak K J, Bi W, Strout M P, Bloomfield C D, Caligiuri M A. Detection of minimal residual disease in patients with AML1/ETO-associated acute myeloid leukemia using a novel quantitative reverse transcription polymerase chain reaction assay. Leukemia 1998; 12:1482-1489; Suryanarayana K, Wiltrout T A, Vasquez G M, Hirsch V M, Lifson J D. Plasma SIV RNA viral load determination by real-time quantification of product generation in reverse transcriptase-polymerase chain reaction. AIDS Res Hum Retroviruses 1998; 14:183-189; Morris T, Robertson B, Gallagher M. Rapid reverse transcription-PCR detection of hepatitis C virus RNA in serum by using the TaqMan fluorogenic detection system. J Clin Microbiol 1996; 34:2933-2936; Swan D C, Tucker R A, Holloway B P, Icenogle J P. A sensitive, type-specific, fluorogenic probe assay for detection of human papillomavirus DNA. J Clin Microbiol 1997; 35:886-891; McGoldrick A, Lowings J P, Ibata G, Sands J J, Belak S, Paton D J. A novel approach to the detection of classical swine fever virus by RT-PCR with a fluorogenic probe (TaqMan). J Virol Methods 1998; 72:125-135; Abe, A., K. Inoue, T. Tanaka, J. Kato, N. Kajiyama, R. Kawaguchi, S. Tanaka, M. Yoshiba, and M. Kohara 1999. Quantitation of hepatitis B virus genomic DNA by real-time detection PCR. J Clin Microbiol. 37:2899-2903; Aberham, C., C. Pendl, P. Gross, G. Zerlauth, and M. Gessner 2001. A quantitative, internally controlled real-time PCR Assay for the detection of parvovirus B19 DNA. J Virol Methods. 92:183-191; Bisset, L. R., S. Bosbach, Z. Tomasik, H. Lutz, J. Schupbach, and J. Boni 2001. Quantification of in vitro retroviral replication using a one-tube real-time RT-PCR system incorporating direct RNA preparation. J Virol Methods. 91:149-155; Cane, P. A., P. Cook, D. Ratcliffe, D. Mutimer, and D. Pillay 1999. Use of real-time PCR and fluorimetry to detect lamivudine resistance-associated mutations in hepatitis B virus. Antimicrob Agents Chemother. 43:1600-1608; Cubie, H. A., A. L. Seagar, E. McGoogan, J. Whitehead, A. Brass, M. J. Arends, and M. W. Whitley 2001. Rapid real time PCR to distinguish between high risk human papillomavirus types 16 and 18. Mol. Pathol. 54:24-29; Desire, N., A. Dehee, V. Schneider, C. Jacomet, C. Goujon, P. M. Girard, W. Rozenbaum, and J. C. Nicolas 2001. Quantification of human immunodeficiency virus type 1 proviral load by a TaqMan real-time PCR assay. J Clin Microbiol. 39:1303-1310; Gault, E., Y. Michel, A. Dehee, C. Belabani, J. C. Nicolas, and A. Garbarg-Chenon 2001. Quantification of human cytomegalovirus DNA by real-time PCR. J Clin Microbiol. 39:772-775; Gruber, F., F. G. Falkner, F. Dorner, and T. Hammerle 2001. Quantitation of viral DNA by real-time PCR applying duplex amplification, internal standardization, and two-color fluorescence detection. Appl Environ Microbiol. 67:2837-2839; Jabs, W. J., H. Hennig, M. Kittel, K. Pethig, F. Smets, P. Bucsky, H. Kirchner, and H. J. Wagner 2001. Normalized quantification by real-time PCR of Epstein-Barr virus load in patients at risk for posttransplant lymphoproliferative disorders. J Clin Microbiol. 39:564-569; Josefsson, A., K. Livak, and U. Gyllensten 1999. Detection and quantitation of human papillomavirus by using the fluorescent 5' exonuclease assay. J Clin Microbiol. 37:490-496; Kato, T., M. Mizokami, M.

Mukaide, E. Orito, T. Ohno, T. Nakano, Y. Tanaka, H. Kato, F. Sugauchi, R. Ueda, N. Hirashima, K. Shimamatsu, M. Kage, and M. Kojiro 2000. Development of a TT virus DNA quantification system using real-time detection PCR J Clin Microbiol. 38:94-98; Kearns, A. M., M. Guiver, V. James, and J. King 2001. Development and evaluation of a real-time quantitative PCR for the detection of human cytomegalovirus. J Virol Methods. 95:121-131; Kessler, H. H., G. Muhlbauer, B. Rinner, E. Stelzl, A. Berger, H. W. Dorr, B. Santner, E. Marth, and H. Rabenau 2000. Detection of Herpes simplex virus DNA by real-time PCR. J Clin Microbiol. 38:2638-2642; Kimura, H., M. Morita, Y. Yabuta, K. Kuzushima, K. Kato, S. Kojima, T. Matsuyama, and T. Morishima 1999. Quantitative analysis of Epstein-Barr virus load by using a real-time PCR assay. J Clin Microbiol. 37:132-136; Komurian-Pradel, F., G. Paranhos-Baccala, M. Sodoyer, P. Chevallier, B. Mandrand, V. Lotteau, and P. Andre 2001. Quantitation of HCV RNA using real-time PCR and fluorimetry. J Virol Methods. 95:111-119.; Kuimelis, R. G., K. J. Livak, B. Mullah, and A. Andrus 1997. Structural analogues of TaqMan probes for real-time quantitative PCR. Nucleic Acids Symp Ser. 37:255-256; Lallemand, F., N. Desire, W. Rozenbaum, J. C. Nicolas, and V. Marechal 2000. Quantitative analysis of human herpesvirus 8 viral load using a real-time PCR assay. J Clin Microbiol. 38:1404-1408; Lewin, S. R., M. Vesanen, L. Kostrikis, A. Hurley, M. Duran, L. Zhang, D. D. Ho, and M. Markowitz 1999. Use of real-time PCR and molecular beacons to detect virus replication in human immunodeficiency virus type 1-infected individuals on prolonged effective antiretroviral therapy. J Virol. 73:6099-6103; Locatelli, G., F. Santoro, F. Veglia, A. Gobbi, P. Lusso, and M. S. Malnati 2000. Real-time quantitative PCR for human herpesvirus 6 DNA. J Clin Microbiol. 37:4042-4048; Machida, U., M. Kami, T. Fukui, Y. Kazuyama, M. Kinoshita, Y. Tanaka, Y. Kanda, S. Ogawa, H. Honda, S. Chiba, K. Mitani, Y. Muto, K. Osumi, S. Kimura, and H. Hirai 2000. Real-time automated PCR for early diagnosis and monitoring of cytomegalovirus infection after bone marrow transplantation. J Clin Microbiol. 38:2536-2542; Martell, M., J. Gomez, J. I. Esteban, S. Sauleda, J. Quer, B. Cabot, R. Esteban, and J. Guardia 1999. High-throughput real-time reverse transcription-PCR quantitation of hepatitis C virus RNA. J Clin Microbiol. 37:327-332; Najioullah, F., D. Thouvenot, and B. Lina 2001. Development of a real-time PCR procedure including an internal control for the measurement of HCMV viral load. J Virol Methods. 92:55-64.; Nicoll, S., A. Brass, and H. A. Cubie 2001. Detection of herpes viruses in clinical samples using real-time PCR. J Virol Methods. 96:25-31; Niesters, H. G., J. van Esser, E. Fries, K. C. Wolthers, J. Cornelissen, and A. D. Osterhaus 2000. Development of a real-time quantitative assay for detection of epstein-barr virus. J Clin Microbiol. 38:712-715; Nitsche, A., N. Steuer, C. A. Schmidt, O. Landt, H. Ellerbrok, G. Pauli, and W. Siegert 2000. Detection of human cytomegalovirus DNA by real-time quantitative PCR. J Clin Microbiol. 38:2734-2737; Ohyashiki, J. H., A. Suzuki, K. Aritaki, A. Nagate, N. Shoji, K. Ohyashiki, T. Ojima, K. Abe, and K. Yamamoto 2000. Use of real-time PCR to monitor human herpesvirus 6 reactivation after allogeneic bone marrow transplantation. Int J Mol Med. 6:427-432.; Pevenstein, S. R., R. K. Williams, D. McChesney, E. K. Mont, J. E. Smialek, and S. E. Straus 1999. Quantitation of latent varicella-zoster virus and herpes simplex virus genomes in human trigeminal ganglia. J Virol. 73:10514-10548; Ratge, D., B. Scheiblhuber, M. Nitsche, and C. Knabbe 2000. High-speed detection of blood-borne hepatitis C virus RNA by single-tube real-time fluorescence reverse transcription-PCR with the LightCycler. Clin Chem. 46:1987-1989; Saha, B. K., B. Tian, and R. P. Bucy 2001. Quantitation of HIV-1 by real-time PCR with a unique fluorogenic probe J Virol Methods. 93:33-42; Sauleda, S., H. J. Reesink, J. I. Esteban, G. Hess, R. Esteban, and J. Guardia 1999. Profiles of GBV-C/hepatitis G virus markers in patients coinfected with hepatitis C virus. J Med Virol. 59:45-51; Schutten, M., B. van den Hoogen, M. E. van der Ende, R. A. Gruters, A. D. Osterhaus, and H. G. Niesters 2000. Development of a real-time quantitative RT-PCR for the detection of HIV-2 RNA in plasma. J Virol Methods. 88:81-87; Takeuchi, T., A. Katsume, T. Tanaka, A. Abe, K. Inoue, K. Tsukiyama-Kohara, R. Kawaguchi, S. Tanaka, and M. Kohara 1999. Real-time detection system for quantification of hepatitis C virus genome. Gastroenterology. 116:636-642; Tanaka, N., H. Kimura, K. Iida, Y. Saito, I. Tsuge, A. Yoshimi, T. Matsuyama, and T. Morishima 2000. Quantitative analysis of cytomegalovirus load using a real-time PCR assay. J Med Virol. 60:455-462; Tucker, R. A., E. R. Unger, B. P. Holloway, and D. C. Swan 2001. Real-time PCR-based fluorescent assay for quantitation of human papillomavirus types 6, 11, 16, and 18. Mol Diagn. 6:39-47; Tyagi, S., and F. R. Kramer 1996. Molecular beacons: probes that fluoresce upon hybridization. Nat Biotechnol. 14:303-308; van Elden, L. J., M. Nijhuis, P. Schipper, R. Schuurman, and A. M. van Loon 2001. Simultaneous detection of influenza viruses A and B using real-time quantitative PCR. J Clin Microbiol. 39:196-200; Vet, J. A., A. R. Majithia, S. A. Majithia, S. Tyagi, S. Dube, B. J. Poiesz, and F. R. Kramer 1999. Multiplex detection of four pathogenic retroviruses using molecular beacons. Proc Natl Acad Sci USA. 96:6394-6399.; Wagner, H. J., W. Jabs, F. Smets, M. Wessel, L. Fischer, G. Offner, H. Kirchner, and P. Bucsky 2000. Real-time polymerase chain reaction (RQ-PCR) for the monitoring of Epstein-Barr virus (EBV) load in peripheral blood mononuclear cells. Klin Padiatr. 212:206-210; Walker, N. J. 2001. Real-time and quantitative PCR: applications to mechanism-based toxicology. J Biochem Mol Toxicol. 15:121-127; White, I. E., and T. B. Campbell 2000. Quantitation of cell-free and cell-associated Kaposi's sarcoma-associated herpesvirus DNA by real-time PCR. J Clin Microbiol. 38:1992-1995;

Example 6

Real-Time RT-PCR Assay for HIV-1.

HIV-1 particles were brought into culture using human PBM cells. Viral RNA present in the culture supernatant was prepared using commercially available columns (QIAamp Viral RNA mini Kit, Qiagen, CA). RT-PCR-amplified RNA was detected in real-time by monitoring increases in fluorescence signal. A total of 5 L RNA was RT-amplified using reagents and conditions as described by the manufacturer (Applied Biosystems, CA). The standard curve ranged from $1.41 \times 10^2$ copies/mL to over $1.41 \times 10^8$ copies/mL. Copy numbers were calibrated using the Roche Amplicor HIV-1 Monitor test™ (Roche Diagnostics, Branchburg, N.J.), or the NASBA HIV-1 viral load assay (Organon Technika). Correlation coefficient is in all experiments greater than 0.99. (FIG. 1).

Example 7

Real-Time RT-PCR assay for HCV.

As of today, the only reliable and available system for HCV RNA replication is the replicon system in Huh7 cells. The cells were brought into culture for several days and total RNA present in the culture was prepared using commercially available columns (QIAamp Viral RNA mini Kit, Qiagen, CA). RT-PCR-amplified RNA was detected in real-time by monitoring increases in fluorescence signal. A total of 5 L RNA was RT-amplified using reagents and conditions as described by the manufacturer (Applied Biosystems, CA). The standard curve ranged from 45 IU/mL to over $4.7\times10^7$ IU/mL. Copy numbers were calibrated using the Roche Amplicor HCV Monitor test™ (Roche Diagnostics, Branchburg, N.J.). Correlation coefficient is in all experiments greater than 0.99. (FIG. 2).

Example 8

Real-Time RT-PCR Assay for HBV.

HBV viral particles are released from at leasts three different cell lines: HepG2.2.1.5, HEPAD38 and HepAD79 cell lines. The cells were brought into culture for several days and total nucleic acids present in the culture supernatant, or in the cells, was prepared using commercially available columns (QIAamp Viral RNA mini Kit, Qiagen, CA). PCR-amplified DNA was detected in real-time by monitoring increases in fluorescence signal. A total of 5 L DNA was RT-amplified using reagents and conditions as described by the manufacturer (Applied Biosystems, CA). The standard curve ranged from 2 copies to over $2\times10^7$ copies per reaction mix. Copy numbers were calculated form OD260 values obtained from an HBV standard. Correlation coefficient is in all experiments greater than 0.99.

Example 9

Real-Time RT-PCR Assay for BVDV

BVDV viral particles are released from infection experiments using the strain NADL on MDBK cells (both available form ATTC). After infection, the cell were brought into culture for several days and total nucleic acids present in the culture supernatant, or in the cells, was prepared using commercially available columns (QIAamp Viral RNA mini Kit, Qiagen, CA). RT-PCR-amplified RNA was detected in real-time by monitoring increases in fluorescence signal. A total of 5 L DNA was RT-amplified using reagents and conditions as described by the manufacturer (Applied Biosystems, CA). The standard curve ranged from 0.6 plaque forming units to over $6\times10^3$ plaque forming units per reaction mix. Plaque forming units were calculated form traditional plaque assays. Correlation coefficient is in all experiments greater than 0.99.

Example 10

Real-Time RT-PCR Assay for RSV

RSV viral particles are released from infection experiments using the available virus strain derived from a clinical sample on A549 or Hep2 cells. After infection, the cell were brought into culture for several days and total nucleic acids present in the culture supernatant, or in the cells, was prepared using commercially available columns (QIAamp Viral RNA mini Kit, Qiagen, CA). RT-PCR-amplified RNA was detected in real-time by monitoring increases in fluorescence signal. A total of 5 L DNA was RT-amplified using reagents and conditions as described by the manufacturer (Applied Biosystems, CA). The standard curve ranged from 70 plaque forming units to over $7\times110$ plaque forming units/mL. Plaque forming units were calculated form traditional plaque assays. Correlation coefficient is in all experiments greater than 0.99. Hep2 cells gave the highest virus titer after 72 hours of incubation, the amount of cells used varied between 10,000 and 50,000 cells per well, but there were no differences observed in total amount of virus production at 72 hours.

Example 11

Real-Time PCR Assay for Human Mitochondrial DNA and β-actin DNA

The current inventions involve the amplification of these two genetic targets for mitochondrial toxicity testing. Therefore, a set of primers and fluorescent probes for both mitochondrial and nuclear DNA or RNA was designed.

As one illustration of this method, in a first step, HepG2 cells are kept in culture in presence of 10 microMolar of a set of candidate antiviral agents. Subsequently, total DNA is isolated from cultured HepG2 cells by means of a commercially available columns (QIAamp DNA Blood Mini Kit, Qiagen, CA). Total DNA was eluted from columns in 200 L water. The mitochondrial gene and nuclear gene are then amplified with a quantitative real-time PCR protocol using the suitable primers and probes. Reagents and conditions used in quantitative PCR were purchased from PE-Applied Biosystems.

In a separate experiment, the amplification efficiencies of both targets were evaluated. The standard curve that was created using the diluted total cell DNA showed linearity over 4 logs [FIG. 3]. Furthermore, FIG. 3 demonstrates that efficiencies of target and reference amplification are approximately equal, because the value of the slope of input amount versus DeltaCt (Ct β-actin-Ct mitochondrial; Ct=PCR cycle threshold where a sample becomes detectable) is less than 0.1.

There are at least two methods to obtain accurate quantity measurements, one method is using standard curves, the other method is known as the comparative cycle threshold method. The basics of the two methods are explained in the User Bulletin # 2 of PE Applied Biosystems. Since both target mitochondrial and the nuclear endogenous control gene are amplified with almost identical efficiencies using the described primer-probe sets, either method can be used to measure the mitochondrial toxicities induced by antiviral agents. Preferably, the comparative Ct method is used. This method uses arithmetic formulas to achieve the same result for relative quantification as obtained by standard curve methods (see User Bulletin #2; PE Applied Biosystems). In this arithmetic formula, the amount of target (mitochondrial DNA) is normalized to a calibrator (nuclear gene) and is relative to an endogenous reference (no drug control at day 7 or 14, depending on the setup of the experiment). This arithmetic formula is given by $2^{-Ct}$.

Figure 4:
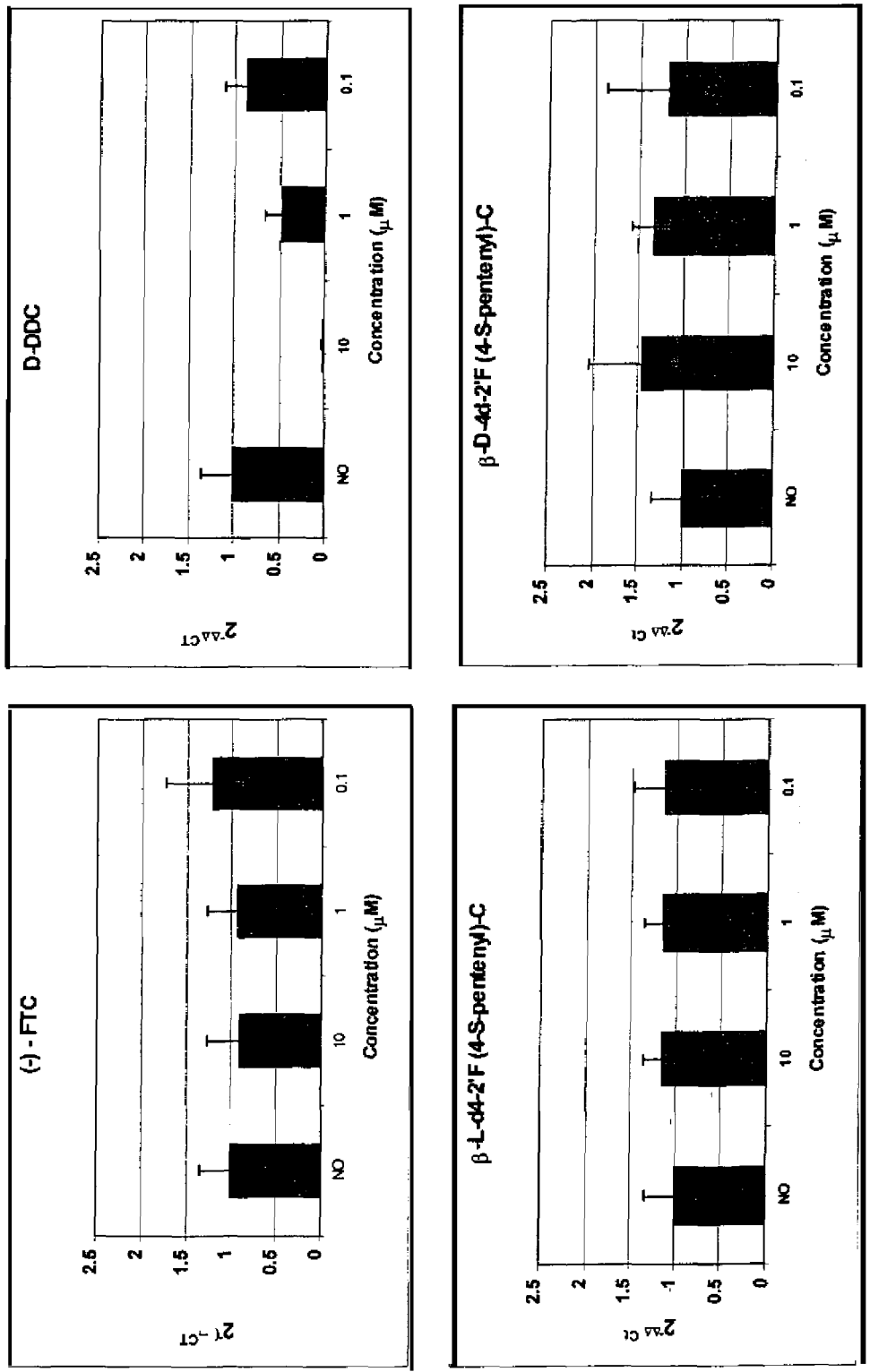
FIG. 4 is a non-limiting illustration of RT-PCR standard curves and relative efficiency plot. In this particular example, quantities of β-actin DNA and mitochondrial DNA were measured in real-time to generate the following plots: 1) the ◆ line is the β-actin standard curve; 2) the ■ line is the mitochondrial DNA standard curve; and 3) the ▲ line is a ΔCt plot (Ct β-actin-Ct mitochondrial).

In order to find out whether antiviral compounds should have any inhibitory effect on the mitochondrial DNA polymerase γ the mitochondrial COXII gene and the nuclear -actin gene were amplified simultaneously. The relative mitochondrial DNA polymerase γ toxicity of two antiviral compounds (−)-FTC and D-DDC were compared with some candidate new antiviral compounds. FIG. 4 demonstrates the results obtained for these antiviral agents. It is clear from this figure that (−)-FTC does not induce any significant mitochondrial DNA reduction as compared to the no-drug control. Instead, important differences were observed for D-DDC at 1 and 10 microM concentration. The observed reduction in mitochondrial DNA in the DDC settings illustrates the usefulness of the simultaneous amplification of two or more different targets in molecular toxicology.

Similar results were also obtained if this technology was carried out in a quantitative reverse-transcriptase-PCR protocol. This approach measures the potential inhibition of antiviral compounds for the mitochondrial RNA polymerase, in comparison with the nuclear RNA polymerases I (generating mainly rRNA transcripts), RNA polymerase II (generating mainly mRNA transcripts), or of lesser importance, RNA polymerase III (generating mainly tRNA transcripts). To obtain such results, amplification of either rRNA, or -actin mRNA as calibrator is required. In these experiments and after calibration against the relevant nuclear RNA polymerase transcripts and normalization for no treatment, DDC also showed a significant reduction in mitochondrial RNA levels, while (−) FTC did not affect the COXII RNA levels.

This approach can be used to evaluate the molecular toxicity levels of any candidate antiviral compounds tested in any cell type.

Total DNA is isolated from cultured HepG2 cells by commercially available columns (QIAamp DNA Blood Mini Kit, Qiagen, CA). Total DNA was eluted from columns in 200 μL of water. The mitochondrial gene and nuclear gene are then amplified with a quantitative real-time PCR protocol using suitable primers and probes. A set of primers and fluorescent probes for both nuclear and mitochondrial DNA or RNA was designed; the endogenous control DNA primer set is given by 5'-GCG CGG CTA CAG CTT CA-3' (SEQ ID NO: 1) and 5'-TCT CCT TAA TGT CAC GCA CGA T-3' (SEQ ID NO: 2); the mitochondrial DNA primer set is given by 5'-TGC CCG CCA TCA TCC TA-3' (SEQ ID NO: 19) and 5'-TCG TCT GTT ATG TAA AGG ATG CGT-3' (SEQ ID NO: 20). The probe for nuclear gene is given by 5'-fluorescent Dye-CAC CAC GGC CGA GCG GGA-fluorescent quencher-3' (SEQ ID NO: 23); fluorescent labeled probes for mitochondrial genome is given by 5'-fluorescent Dye-TCC TCA TCG CCC TCC CAT CCC-fluorescent quencher-3' (SEQ ID NO: 24). Reagents and conditions used in quantitative PCR were purchased from PE-Applied Biosystems.

The standard curve created using the diluted total cell DNA showed linearity over 4 logs [FIG. 4]. Furthermore, FIG. 4 demonstrates that efficiencies of target and reference amplification are approximately equal, because the value of the slope of input amount versus ΔCt (Ct β-actin-Ct mitochondrial; Ct=PCR cycle threshold where a sample becomes detectable) is less than 0.1.

There are at least two methods to obtain accurate quantity measurements, one method is using standard curves, and the other method is known as the comparative cycle threshold method. The basics of the two methods are explained in the User Bulletin # 2 of PE Applied Biosystems. Since both target mitochondrial and the nuclear endogenous control gene are amplified with almost identical efficiencies using the described primer-probe sets, either method can be used to measure the mitochondrial toxicities induced by antiviral agents. Preferably, the comparative Ct method is used. This method uses arithmetic formulas to achieve the same result for relative quantification as obtained by standard curve methods (see User Bulletin #2; PE Applied Biosystems). In this arithmetic formula, the amount of target (mitochondrial DNA) is normalized to an endogenous reference (nuclear gene) and is relative to a calibrator (no drug control at day 7 or 14, depending on the setup of the experiment). This arithmetic formula is given by $2^{-\Delta\Delta Ct}$.

Example 12

Simultaneous Amplification of HCV RNA and Cellular Targets.

Huh7 cells harboring the HCV replicon can be cultivated in DMEM media (high glucose, no pyruvate) containing 10% fetal bovine serum, 1× non-essential Amino Acids, Pen-Strep-Glu (100 units/liter, 100 microgram/liter, and 2.92 mg/liter, respectively) and 500 to 1000 microgram/milliliter G418. Antiviral screening assays can be done in the same media without G418 as follows: in order to keep cells in logarithmic growth phase, seed cells in a 96-well plate at low density, for example 1000 cells per well. Add the test compound immediate after seeding the cells and incubate for a period of 3 to 7 days at 37° C. in an incubator. Media is then removed, and the cells are prepared for total nucleic acid extraction (including replicon RNA and host RNA). Replicon RNA can then be amplified in a Q-RT-PCR protocol, and quantified accordingly. The observed differences in quantification of replicon RNA is one way to express the antiviral potency of the test compound. A typical experiment demonstrates that in the negative control and in the non-active compounds-settings a comparable amount of replicon is produced. This can be concluded because the measured threshold-cycle for HCV RT-PCR in both setting is close to each other. In such experiments, one way to express the antiviral effectiveness of a compound is to subtract the threshold RT-PCR cycle of the test compound with the average threshold RT-PCR cycle of the negative control. This value is called DeltaCt (Ct). A Ct of 3.3 equals a 1-log reduction (equals ECO) in replicon production. Compounds that result in a reduction of HCV replicon RNA levels of greater than 2 Ct values (75% reduction of replicon RNA) are candidate compounds for antiviral therapy. However, this HCV Ct value does not include any specificity parameter for the replicon encoded viral RNA-dependent RNA polymerase. In a typical setting, a compound might reduce both the host RNA polymerase activity and the replicon-encoded polymerase activity. Therefore, quantification of rRNA (or any other host RNA polymerase I product) or beta-actin mRNA (or any other host RNA polymerase II) and comparison with RNA levels of the no-drug control is a relative measurement of the effect of the test compound on host RNA polymerases.

With the availability of both the HCV ΔCt data and the rRNA ΔCt, a specificity parameter can be introduced. This parameter is obtained by subtracting both ΔCt values from each other. This results in ΔΔCt values; a value above 0 means that there is more inhibitory effect on the replicon encoded polymerase, a ΔΔCt value below 0 means that the host rRNA levels are more affected than the replicon levels. As an illustration of this technology, the antiviral activity of tested compounds, expressed as ΔΔCt values, is given in FIG. 5. As a general rule, ΔΔCt values above 2 are considered as significantly different from the no-drug treatment control, and hence, is an interested compound for further evaluation. However, compounds with a ΔΔCt value of less than 2, but showing limited molecular cytotoxicty data (rRNA ΔCT between 0 and 2) are also possible active candidate compounds for further evaluation In another typical setting, a compound might reduce the host RNA polymerase activity, but not the host DNA polymerase activity. Therefore, quantification of rDNA or beta-actin DNA (or any other host DNA fragment) and comparison with DNA levels of the no-drug control is a relative measurement of the inhibitory effect of the test compound on cellular DNA polymerases. With the availability of both the HCV ΔCt data and the rDNA ΔCt, a specificity parameter can be introduced. This parameter is obtained by subtracting both ΔCt values from each other. This results in ΔΔCt values; a value above 0 means that there is more inhibitory effect on the replicon encoded polymerase, a ΔΔCt value below 0 means that the host rDNA levels are more affected than the replicon levels. As a general rule, ΔΔCt values above 2 are considered as significantly different from the no-drug treatment control, and hence, is an interested compound for further evaluation. However, compounds with a ΔΔCt value of less than 2, but with limited molecular cytotoxicty (rDNA ΔCT between 0 and 2) are also possible active candidate compounds for further evaluation Quantitative real-time PCR antiviral screening can be combined with calibration for a nuclear RNA targets (in RT-PCR) in the following settings: anti-HCV compound screening can be combined with rRNA calibration, or -actin mRNA calibration, or any other nuclear or mitochondrial gene calibration. Anti-HIV compound screening can be combined with rRNA calibration, -actin mRNA calibration or any other nuclear or mitochondrial gene calibration. Anti-HBV compound screening can be combined with rRNA calibration, -actin mRNA calibration, or any other nuclear or mitochondrial gene calibration. Anti-RSV compound screening can be combined with rRNA calibration, -actin mRNA calibration, or any other nuclear or mitochondrial gene calibration. Anti-BVDV compound screening can be combined with rRNA calibration, -actin mRNA calibration or any other nuclear or mitochondrial gene calibration. Anti-lentivirus compound screening can be combined with rRNA calibration, -actin mRNA calibration or any other nuclear or mitochondrial gene calibration. Anti-flaviviridae (Flavivirus, Hepacivirus, Pestivirus) compound screening can be combined with rRNA calibration, -actin mRNA calibration or any other nuclear or mitochondrial gene calibration. Anti-hepadnavirus compound screening can be combined with rRNA calibration, -actin mRNA calibration or any other nuclear or mitochondrial gene calibration. Anti-Picornavirus compound screening can be combined with rRNA calibration, -actin mRNA calibration or any other nuclear or mitochondrial gene calibration. Anti-Herpetoviridae (HSV, HCMV, EBV) compound screening can be combined with rRNA calibration, -actin mRNA calibration or any other nuclear or mitochondrial gene calibration.

Quantitative real-time PCR antiviral screening can be combined with calibration for a nuclear DNA target (in PCR) in the following conditions. anti-HCV compound screening can be combined with rDNA calibration, or -actin DNA calibration, or any other nuclear or mitochondrial gene calibration. Anti-HIV compound screening can be combined with rDNA calibration, -actin DNA calibration or any other nuclear or mitochondrial gene calibration. Anti-HBV compound screening can be combined with rDNA calibration, -actin DNA calibration or any other nuclear or mitochondrial gene calibration. Anti-RSV compound screening can be combined with rDNA calibration, -actin DNA calibration or any other nuclear or mitochondrial gene calibration. Anti-BVDV compound screening can be combined with rDNA calibration, -actin DNA calibration, or any other nuclear or mitochondrial gene calibration. Anti-lentivirus compound screening can be combined with rDNA calibration, -actin DNA calibration or any other nuclear or mitochondrial gene calibration. Anti-flaviviridae (Flavivirus, Hepacivirus, Pestivirus) compound screening can be combined with rDNA calibration, -actin DNA calibration or any other nuclear or mitochondrial gene calibration. Anti-hepadnavirus compound screening can be combined with rDNA calibration, -actin DNA calibration or any other nuclear or mitochondrial gene calibration. Anti-Picornavirus compound screening can be combined with rDNA calibration, -actin DNA calibration or any other nuclear or mitochondrial gene calibration.

Anti-Herpetoviridae (HSV, HCMV, EBV) compound screening can be combined with rDNA calibration, -actin DNA calibration or any other nuclear or mitochondrial gene calibration.

Example 13

Toxicity Assays

HepG2, VERO ($5 \times 10^3$ cells per well), CEM ($2.5 \times 10^3$ per well), and PBMC ($5 \times 10^4$ per well) were seeded in 96-well plates at in the presence of increasing concentrations of the test compound and incubated in a 37° C., 5% $CO_2$ incubator. After a three day-incubation, or 4 for CEM, or 5 days for PBMC, cell viability and mitochondrial activity were measured in a colorimetric assay using the MTS- or MTT dye (Promega, Wis.).

Example 14

Figure 3:
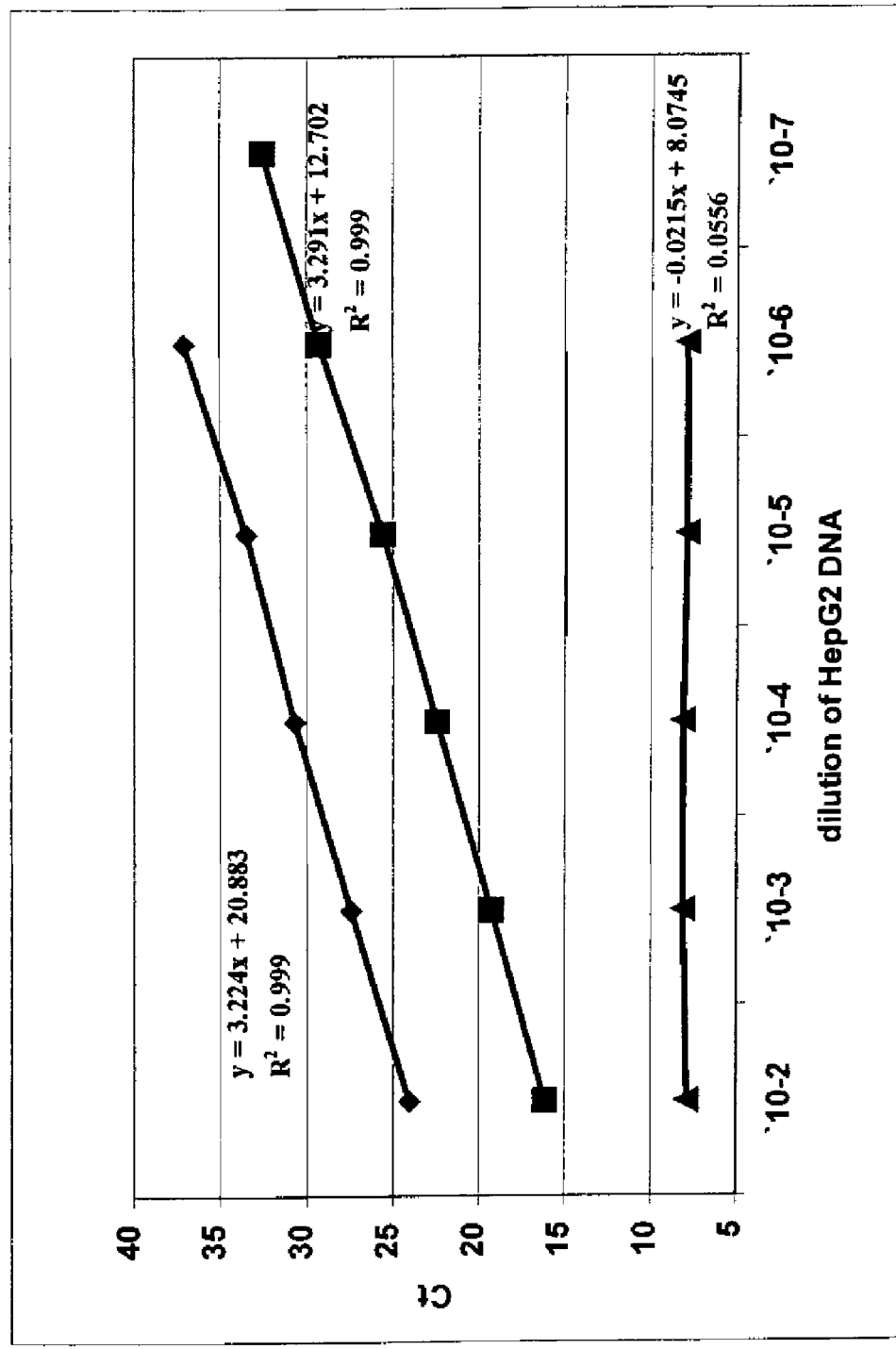
FIG. 3 are illustrations of the effect of antiviral compounds on viral load and RT activity in culture supernatant. The ◆ line indicates data from a traditional RT assay, while the ■ line represents data obtained from using HIV-1 RT-PCR.

Antiviral RT-PCR Versus RT Assay

β-L and β-D analogues of 2',3'-didehydro-2',3'-dideoxy-2'-fluoro-4'-thio-cytidine ["d4-2'-F-(4S-pentenyl)-C"] were compared with a selection of antivirals that are currently FDA-approved, or in clinical trial such as AZT, 3TC, d4T, and (−)-FTC against a two HIV-1 viral strains a sensitive strain, xxBRU, and a 3TC-resistant viral strain with the 184V mutation. Human PBMC were PHA stimulated for 2 days, HIV-1 infected, and kept in culture for 5 days in presence of test compounds at different concentrations. Subsequently, culture supernatant was clarified, and tested for reverse transcription activity by two separate methods. The first method is the standard endogenous viral RT assay with read-out in log counts per minute/mL (CPM/mL) by incorporating tritium-labeled TTP; the second is the RT-PCR method disclosed herein, a quantification method of HIV-1 viral load using real-time PCR quantification assay with read-out in log copies/mL. FIG. 3 shows the result for some of the tested compound on both viral strains. Although the two methodologies are measuring for different items (viral RNA versus active RT enzyme) results were not-significantly different from each other (FIG. 3, Table 1). The median 50% ($EC_{50}$) and 90% ($EC_{90}$) effective antiviral concentrations were in concordance for the two methodologies used.

Wild type xxBRU virus production in this system was very high, with a total of up to $3 \times 10^8$ copies/mL in the untreated samples. Upon addition of antiviral compounds to the culture media, a dose-related decrease in virus production was observed. Maximal effect of suppression of viral

TABLE 1

| | xxBRU | | | | 184V | | | |
|---|---|---|---|---|---|---|---|---|
| | RT assay | | real-time RT-PCR | | RT assay | | real-time RT-PCR | |
| | $EC_{50}$ | $EC_{90}$ | $EC_{50}$ | $EC_{90}$ | $EC_{50}$ | $EC_{90}$ | $EC_{50}$ | $EC_{90}$ |
| AZT | 0.0034 | 0.034 | 0.0039 | 0.036 | 0.013 | 0.12 | ND | ND |
| 3TC | 0.018 | 0.077 | 0.03 | 0.12 | >100 | >100 | ND | ND |
| d4T | 0.0034 | 0.13 | 0.0027 | 0.12 | 0.032 | 0.19 | 0.00078 | 0.19 |
| (−) FTC | 0.011 | 0.05 | 0.0059 | 0.088 | 65.1 | 160 | 0.34 | >100 |
| β-L-d4-2'F-(4-S-pentenyl)-C | 1.61 | 11.6 | 0.4 | 2.68 | >100 | >100 | 0.091 | 34.9 |
| β-D-d4-2'F-(4-S-pentenyl)-C | 5.98 | 23.2 | 2.68 | 18.1 | >100 | >100 | 11.8 | >100 |

ND: not done

Example 15

MTS/MTT Toxicity and Real-time PCR Mitochondrial DNA Polymerase Toxicity

Mitochondrial toxicity (γ-DNA polymerase inhibition) was evaluated by real-time PCR, using the comparative cycle threshold (Ct) method. β-Actin served as an endogenous reference. All compounds were tested in routine MTT or MTS toxicity assays (material and methods). In order to find out whether these compounds should have any inhibitory effect on the mitochondrial DNA polymerase γ, a real time PCR technology for mitochondrial DNA polymerase toxicity was designed. In a first step, standard curves using 1-log diluted total HepG2 DNA were created, and showed linearity over at least 4 logs (only 4-logs were tested for these targets). FIG. 4 demonstrates that efficiencies of target and reference amplification are approximately equal, because the value of the slope of input amount versus ΔCt (Ct β-actin minus Ct mitochondrial, wherein Ct is the PCR cycle threshold where a sample becomes detectable) is less than 0.1.

Furthermore, total DNA was isolated from HepG2 cells cultured in presence of the antiviral compound. The mitochondrial gene and the β-actin gene were then amplified. There are at least two methods to obtain accurate quantity measurements, one method is using standard curves, the other method is known as the comparative cycle threshold method (User Bulletin # 2; Applied Biosystems, CA). Since both targets (mitochondrial and β-actin) are amplified with almost identical efficiencies using the described primer-probe sets, either method can be used to measure the mitochondrial toxicities induced by antiviral agents. In our experiments, the comparative Ct method was used. This method uses arithmetic formulas in which the amount of target (mitochondrial DNA) is normalized to an endogenous reference (β-actin gene) and is relative to a calibrator (no drug control at day 7). This arithmetic formula is given by $2^{-\Delta\Delta Ct}$.

Figure 5:
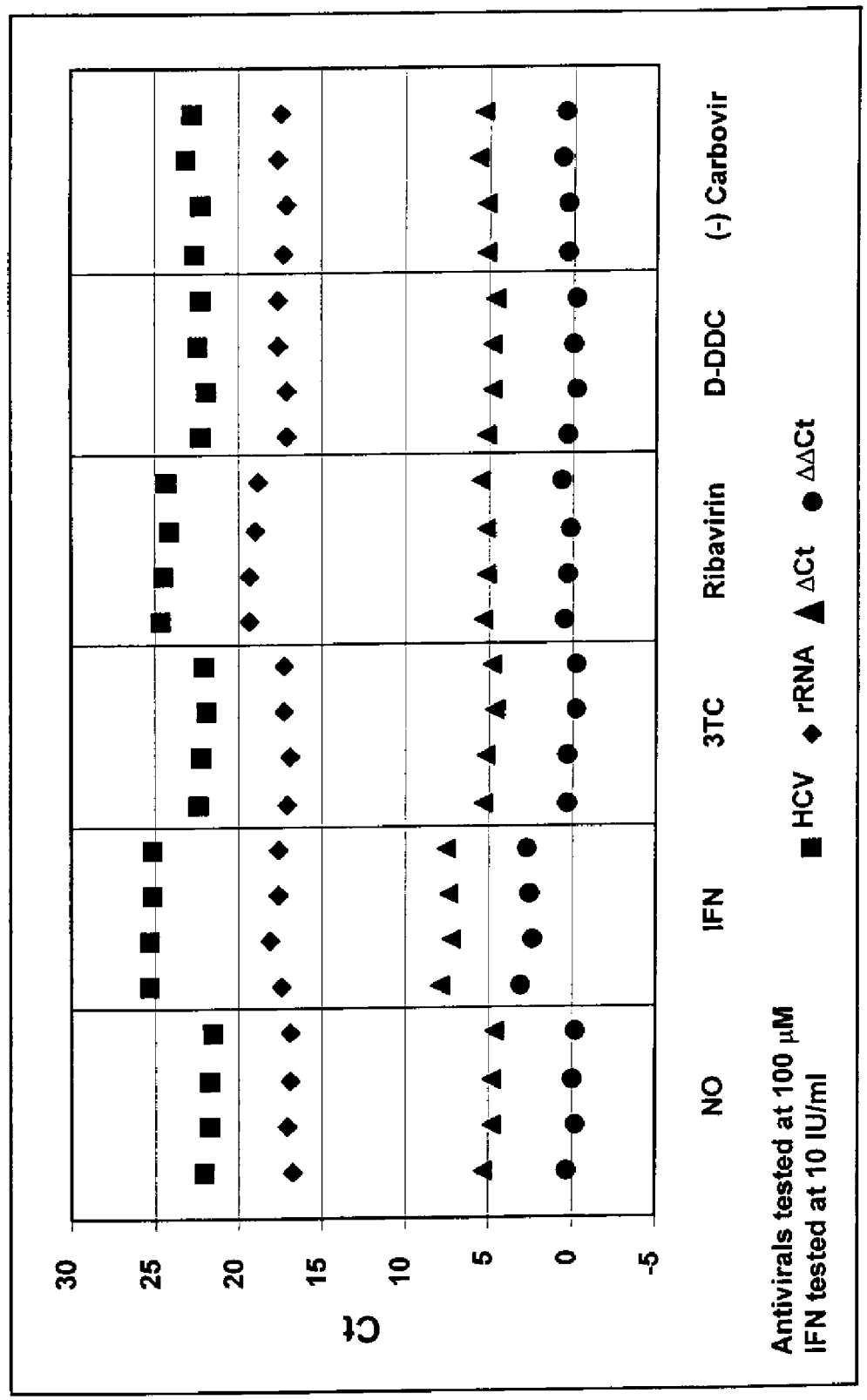
FIG. 5 are illustration of the effect of antiviral compounds on mitochondrial DNA polymerase γ. $2^{-\Delta\Delta CT}$ is the arithmetic formula used to express the differences in mitochondrial DNA after calibration (no drug) and normalization (β-actin). Concentrations are in μM.
Figure 6:
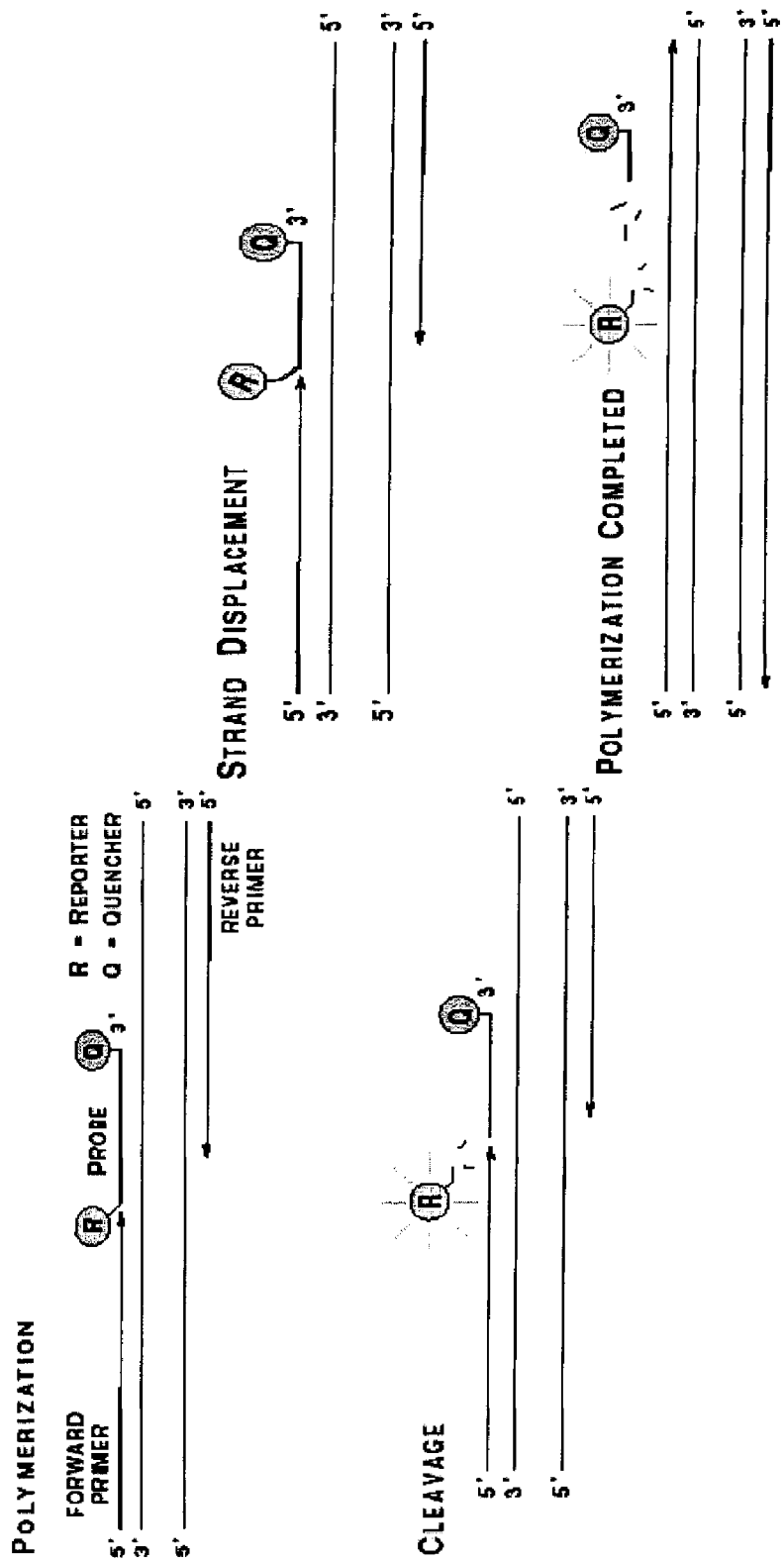
FIG. 6 is an illustration of the quantitative detection of viral nucleic acids by real-time PCR. A fluorogenic probe is shown during the extension phase of PCR. If the target sequence is present, the probe anneals downstream from one of the primer sites and is cleaved by the 5' nuclease activity of Taq DNA polymerase as this primer is extended. This cleavage of the probe separates the reporter dye from quencher dye, increasing the reporter dye signal. Cleavage removes the probe from the target strand, allowing primer extension to continue to the end of the template strand. Thus, inclusion of the probe does not inhibit the overall PCR process. Additional reporter dye molecules are cleaved from their respective probes with each cycle, effecting an increase in fluorescence intensity proportional to the amount of amplicon produced.
Figure 7:
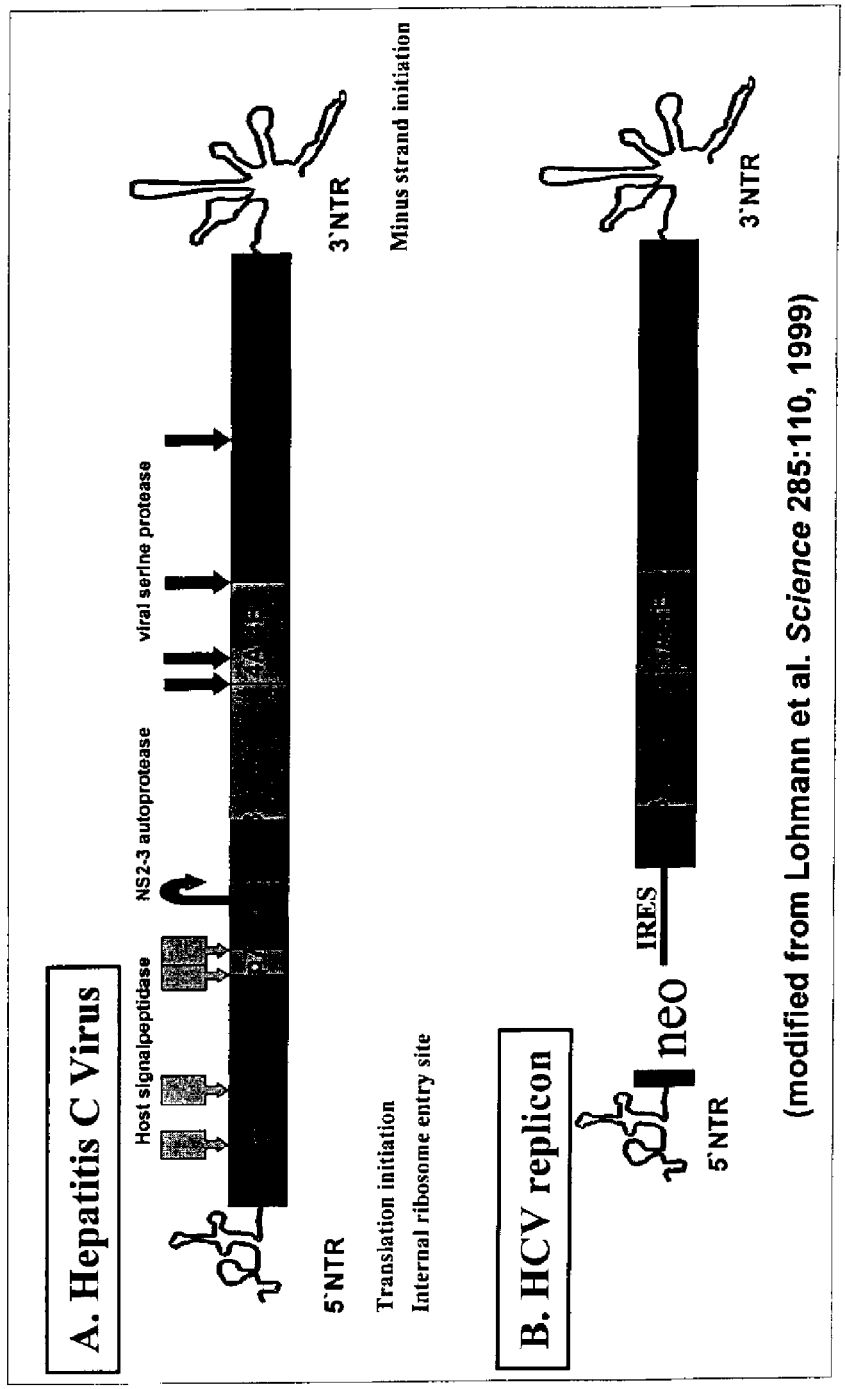
FIG. 7 is an illustration of the organization of the HCV genome as compared to the Hepatitis C Virus replicon, indicating the location of cleavage sites within the polyprotein and the nontranslated regions (NTRs). The open reading frame (ORF) is flanked on the 5' end by an NTR that functions as an internal ribosome entry site (IRES) and at the 3' end by a highly conserved sequence essential for genome replication.
Figure 8:
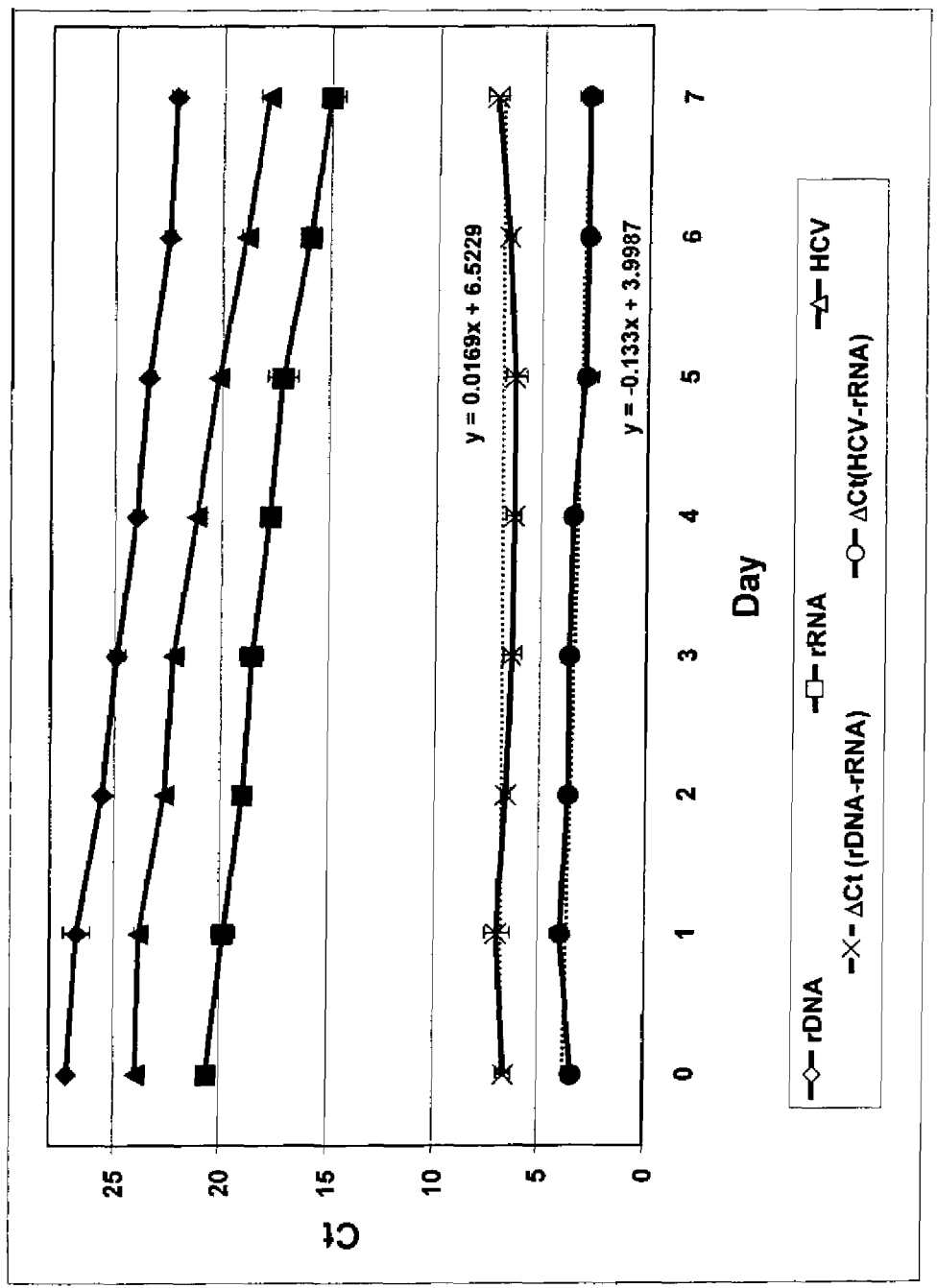
FIG. 8 is a graph of the changes in the amounts of cellular and viral nucleic acids over a seven day incubation period in Huh7/HCV Replicon cells.
Figure 9:
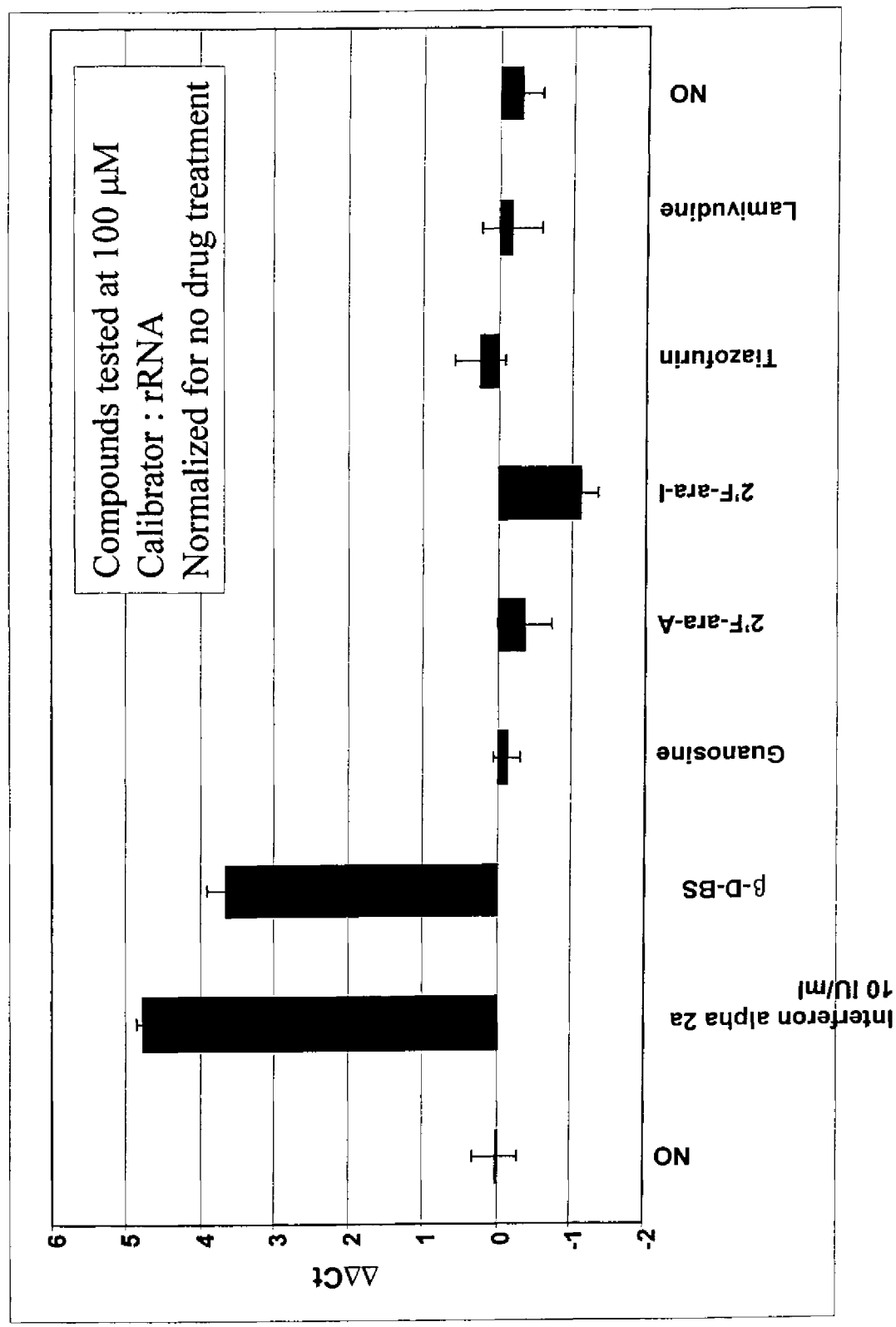
FIG. 9 is a bar graph of the effect of test compounds on HCV RNA levels in the Huh7 HCV replicon system.

The relative mitochondrial DNA polymerase γ toxicity of two antiviral compounds (−)-FTC and D-DDC were compared alongside. FIG. 5 demonstrates the results obtained for each antiviral agent. It is clear from this figure that (−)-FTC does not induce any significant mitochondrial DNA reduction as compared to the no-drug control. Instead, important differences were observed for D-DDC at 1 and 10 μM concentration. D-DDC demonstrated dose-dependent reduction in mitochondrial DNA synthesis as compared to the no-drug control. The β-L and β-D analogues of 2',3'-didehydro-2',3'-dideoxy-2'-fluoro-4'-thio-cytidine ["d4-2'-F-(4S-pentenyl)-C"] both showed no toxicity after a 7-day incubation with up to 10 μM of the compounds using this approach. Similarly, in an MTS-dye assay (Promega), no cytotoxicity was observed for these compounds in human PBMC, Vero and CEM cells when evaluated up to 100 μM; its $CC_{50}$ values were higher than 100 μM on all cell-types tested (HepG2, VERO, PBMC, and CEM).

Example 16

Cell culture assays were used to determine the anti-Flaviviridae activity of unmodified or modified ribonucleosides.

(a) RNA Isolation and Quantitative RT-PCR Analysis

An effective process to quantify the viral load in a host, termed real-time polymerase chain reaction ("RT-PCR") is provided. The process involves using a quenched fluorescent probe molecule that can be hybridized to viral DNA or RNA. Therefore, upon exonucleolytic degradation, a detectable fluorescent signal can be monitored. Therefore, the RT-PCR amplified DNA or RNA is detected in real time by monitoring the presence of fluorescence signals.

As one illustration of this method, in the case of BVDV in MDBK cells, in a first step, viral RNA is isolated from 140 μL of the cell culture supernatant by means of a commercially available column (Viral RNA extraction kit, QiaGen, CA). The viral RNA is then eluted from the column to yield a total volume of 60 μL, and subsequently amplified with a quantitative RT-PCR protocol using a suitable primer for the BVDV NADL strain. A quenched fluorescent probe molecule is hybridized to the BVDV DNA, which then undergoes exonucleolytic degradation resulting in a detectable fluorescent signal. Therefore, the RT-PCR amplified DNA was detected in real time by monitoring the presence of fluorescence signals. The TaqMan probe molecule (5'-6-FAM-AAATCCTC-CTAACAAGCGGGTTCCAGG-TAMRA 3' (SEQ ID NO: 25 and primers (sense: 5'-AGCCTTCAGTTTCTTGCT-GATGT-3' SEQ ID NO: 26; and antisense: 5'-TGTTGC-GAAAGCACCAACAG-3' SEQ ID NO: 27)) were designed with the aid of the Primer Express software (PE-Applied Biosystems) to be complementary to the BVDV NADL NS5B region. A total of 10 μL of RNA was analyzed in a 50 μL RT-PCR mixture. Reagents and conditions used in quantitative PCR were purchased from PE-Applied Biosystems. The standard curve that was created using the undiluted inoculum virus ranged from 6000 plaque forming units (PFU to 0.6 PFU per RT-PCR mixture. A linear range of over 4-logs was routinely obtained.

A comparable approach can be taken to measure the amount of other Flaviviridae (more importantly HCV, YFV, Dengue, West Nile Virus and others) in a clinical sample or in a tissue culture sample. For example, the combination of HCV RNA purification with real-time RT-PCR using the following primers (5'-TTCCGCAGACCACTATGG-3' SEQ ID NO: 8) and 5'-AGCCATGGCGTTAGTATGAGTGT-3' (SEQ ID NO: 28)) and probe (5'-6-FAM-CCTCCAGGAC-CCCCCCTCCC-TAMRA-3' (SEQ ID NO: 29)) resulted in a 7-log linear range of viral load detection.

(b) Cell/Viral Materials

One of the best characterized members of the Pestivirus genus is BVDV. BVDV and HCV share at least three common features, which are the following: (1) they the both undergo IRES-mediated translation; (2) NS4A cofactor is required by their NS3 serine protease; and (3) they undergo similar polyprotein processing within the non-structural region, especially at the NS5A and NS5B junction site.

The BVDV replication system was used for the discovery of anti-Flaviviridae compounds. The compounds described herein are active against Pestiviruses, Hepaciviruses and/or Flaviviruses.

Maldin-Darby bovine kidney (MDBK) cells were grown and maintained in a modified eagle medium (DMEM/F12; GibcoBRL), supplemented with 10% heat inactivated horse serum at 37° C. in a humidified, 5% $CO_2$, incubator.

Bovine viral diarrhea virus (BVDV), strain NADL, causes a cytopathogenic effect (CPE) after infection of these cells.

(c) Antiviral Assay

MDBK-cells, grown in DMEM/F12-10% horse serum (HS), were isolated in standard techniques using trypsin-EDTA. Cells were seeded in a 96-well plate at $5 \times 10^4$ cells/well, with test compound (20 micromolar (μM) concentration) to give a total volume of 100 microliters (μL). After one hour, the media was removed and the cells were infected at a multiplicity of infection (MOI) of 0.02 or 0.002 in a total volume of 50 μL for 45 minutes. Thereafter, the virus was removed and the cells were washed twice with 100 μL of assay media. Finally, the infected cells were incubated in a total volume of 100 μL containing the test compound at 10, 40 or 100 μM concentration. After 22 hours, the cell supernatant was collected by removing the cellular debris by low-speed centrifugation, and subsequently tested for the presence of virus in a quantitative manner.

(d) Cytotoxicity Testing of Candidate Anti-Flaviviridae Compounds

The cytotoxicity testing as performed here is a standard technique. Briefly, cells are seeded in 96-well plates at various concentrations (dependent on cell type, duration of assay), typically at $5 \times 10^3$ cells per well, in the presence of increasing concentrations of the test compound (0, 1, 3, 10, 33, and 100 μM). After a three day-incubation, cell viability and mitochondrial activity are measured by adding the MTS-dye (Promega), followed by a 3 hours incubation. Afterwards the plates containing the dye are read at 490 nm. Such methodologies are well described and available from the manufacturer (Promega).

Example 17

The BVDV RT-PCR Quantification Standard Curve

The standard BVDV virus stock contained $2 \times 10^6$ PFU/mL, as determined by routine plaque assay (Mendez, E. et al. *J. Virol.* 1998, 72, 4737). Viral RNA was extracted from 140 μL of this inoculum material and eluted from a column using 60 μL of an elution buffer. This purified RNA material then was diluted stepwise from $10^{-1}$ to $10^{-5}$. Using the real-time RT-PCR amplification technique, 10 μL of each dilution was tested. The results of this dilution series are plotted in FIG. 1, relating PFU to concentration of standard. From this experiment, it is clear that this technology allows for reliable quantification over 4-logs of virus (from 6000 to 0.6 PFU/input in amplification mix). The lower limit of detection in this experiment is 0.6 PFU or −0.22 log PFU. Therefore, the real-time RT-PCR quantification values of test samples below this detection limit were considered non-reliable.

Example 18

The BVDV Replication Cycle in MDBK Cells

In order to measure the BVDV production in MDBK cells and to determine the optimal harvesting time over a certain period of time, cells were seeded at $5 \times 10^4$ cells/well and infected either with MOI=0.02 or MOI=0.002. After infection, the inoculum was removed and the cells were washed twice with culture medium. At different time points, the cell supernatant was harvested; and, the amount of virus was measured and compared to the original inoculum and the cell wash. At least 2 wash-steps were needed to remove the inoculum virus, as shown in FIG. 2. The amount of virus produced 22 hours after infection approximately equals the amount of virus used to inoculate the cells. Based on these results, the time required for one replication cycle of BVDV in MDBK cells was 22 hours. Note that the detection level set in these experiments was based on the lower limit of detection as determined by the standard curve.

Example 19

Evaluation of Candidate Antiviral Compounds Using RT-PCR

MDBK cells were seeded at $5 \times 10^4$ cells/well, infected with BVDV with a multiplicity of infection (MOI) equal to 0.02 and grown for 22 hours in the presence of a test compound. Cells that were not treated with a test compound were considered a negative control, while ribavirin served as a positive control. Viral RNA was extracted and analyzed by real time RT-PCR. A typical experiment, shown in FIG. 3, demonstrates that the negative control and the majority of the treated cells produced comparable amounts of virus (between 1.5 and 2 log PFU/input), effectively showing the test compounds as non-active. However, the cells treated with the positive control, ribavirin (RIB) or with 5-hydroxyuridine (I-a-45) show an almost complete absence of viral RNA. RIB and I-a-45 reduce viral production by approximately 2 log PFU, or 99%, in the 22 hour reproduction period. The exact potency of these compounds cannot be deduced from this kind of experiment, since the detection limit in this experiment is set at −0.22 log PFU and only one cycle of viral replication occurs under the stated experimental conditions.

Potencies, or the effect concentration of compounds that inhibits virus production by 50% or 90% ($EC_{50}$ or $EC_{90}$ values, respectively), of anti-BVDV compounds were determined in a similar set of experiments, but over a broad range of test compound concentrations (0, 1, 3, 10, 33, 100 μM). The $EC_{90}$ value refers to the concentration necessary to obtain a 1-log reduction in viral production within a 22 hour period.

The invention has been described with reference to various specific and preferred embodiments and techniques. However, it should be understood that many variations and modifications will be obvious to those skilled in the art from the foregoing detailed description of the invention and may be made while remaining within the spirit and scope of the invention.

We claim:

1. A kit for assessing mitochondrial toxicity of a compound, comprising
a mixture of oligonucleotides comprising
at least one first primer set that provides a first detectable signal on the occurrence of amplification of mitochondrial nucleic acid; and
at least one second primer set that provides a second detectable signal on the occurrence of amplification of host nuclear nucleic acid;
wherein the second primer set comprises the primers of SEQ ID No. 1 and SEQ ID No. 2.

2. The kit according to claim 1 further comprising a probe of SEQ ID No. 3 comprising a reporter molecule and a quencher molecule.

3. The kit according to claim 2, wherein the reporter molecule is FAM and the quencher molecule is TAMRA.

4. The kit according to claim 1, wherein the first primer set comprises the primers of SEQ ID No. 19 and SEQ ID No. 20.

5. The kit according to claim 4 further comprising a probe of SEQ ID No. 21 comprising a reporter molecule and a quencher molecule.

6. The kit according to claim 5, wherein the reporter molecule is TET and the quencher molecule is TAMRA.

7. A kit for assessing mitochondrial toxicity of a compound, comprising
a mixture of oligonucleotides comprising
at least one first primer set that provides a first detectable signal on the occurrence of amplification of mitochondrial nucleic acid; and
at least one second primer set that provides a second detectable signal on the occurrence of amplification of host nuclear nucleic acid;
wherein the first primer set comprises the primers of SEQ ID No. 19 and SEQ ID No. 20.

8. The kit according to claim 7, wherein the second primer set comprises the primers of SEQ ID No. 1 and SEQ ID No. 2.

9. The kit according to claim 8 further comprising a probe of SEQ ID No. 3 comprising a reporter molecule and a quencher molecule.

10. The kit according to claim 9, wherein the reporter molecule is FAM and the quencher molecule is TAMRA.

11. The kit according to claim 7, wherein the first primer set comprises the primers of SEQ ID No. 19 and SEQ ID No. 20.

12. The kit according to claim 11 further comprising a probe of SEQ ID No. 21 comprising a reporter molecule and a quencher molecule.

13. The kit according to claim 12, wherein the reporter molecule is TET and the quencher molecule is TAMRA.

* * * * *